US012570715B2

(12) United States Patent
Hirano et al.

(10) Patent No.: US 12,570,715 B2
(45) Date of Patent: Mar. 10, 2026

(54) T CELL RECEPTORS AND METHODS OF USE THEREOF

(71) Applicant: University Health Network, Toronto (CA)

(72) Inventors: Naoto Hirano, Toronto (CA); Kenji Sugata, Toronto (CA); Kayoko Saso, Toronto (CA)

(73) Assignee: University Health Network, Toronto (CA)

( * ) Notice: Subject to any disclaimer, the term of this patent is extended or adjusted under 35 U.S.C. 154(b) by 953 days.

(21) Appl. No.: 17/631,825

(22) PCT Filed: Jul. 29, 2020

(86) PCT No.: PCT/IB2020/057172
§ 371 (c)(1),
(2) Date: Jan. 31, 2022

(87) PCT Pub. No.: WO2021/019472
PCT Pub. Date: Feb. 4, 2021

(65) Prior Publication Data
US 2022/0281942 A1 Sep. 8, 2022

Related U.S. Application Data

(60) Provisional application No. 62/880,504, filed on Jul. 30, 2019.

(51) Int. Cl.

| | |
|---|---|
| *C07K 14/725* | (2006.01) |
| *A61K 35/17* | (2025.01) |
| *A61K 40/11* | (2025.01) |
| *A61K 40/32* | (2025.01) |
| *A61K 40/42* | (2025.01) |
| *A61P 35/00* | (2006.01) |
| *A61P 35/04* | (2006.01) |
| *C07K 16/30* | (2006.01) |
| *C12N 5/0783* | (2010.01) |
| *C12N 15/113* | (2010.01) |
| *C12N 15/63* | (2006.01) |
| *C12N 15/86* | (2006.01) |

(52) U.S. Cl.
CPC .......... *C07K 14/7051* (2013.01); *A61K 40/11* (2025.01); *A61K 40/32* (2025.01); *A61K 40/4239* (2025.01); *A61P 35/00* (2018.01); *A61P 35/04* (2018.01); *C07K 16/30* (2013.01); *C12N 5/0636* (2013.01); *A61K 35/17* (2013.01); *C07K 2317/565* (2013.01); *C07K 2319/03* (2013.01); *C12N 15/1138* (2013.01); *C12N 15/63* (2013.01); *C12N 15/86* (2013.01); *C12N 2510/00* (2013.01); *C12N 2740/13043* (2013.01); *C12N 2800/00* (2013.01)

(58) Field of Classification Search
CPC ................ C07K 14/7051; C07K 16/30; C07K 2317/565; C07K 2317/622; C07K 2319/03; A61K 40/11; A61K 40/32; A61K 40/4239; A61K 35/17; A61P 35/04; C12N 5/0636; C12N 15/1138; C12N 15/63; C12N 15/86; C12N 2510/00
See application file for complete search history.

(56) References Cited

U.S. PATENT DOCUMENTS

| | | |
|---|---|---|
| 9,181,527 B2 | 11/2015 | Sentman |
| 2010/0273213 A1 | 10/2010 | Mineno et al. |
| 2013/0287748 A1 | 10/2013 | June et al. |
| 2018/0010095 A1 | 1/2018 | Laugel et al. |
| 2019/0119635 A1 | 4/2019 | Robbins et al. |
| 2022/0275046 A1 | 9/2022 | Hirano et al. |
| 2022/0275047 A1 | 9/2022 | Hirano et al. |
| 2022/0281942 A1 | 9/2022 | Hirano et al. |

FOREIGN PATENT DOCUMENTS

| | | |
|---|---|---|
| CA | 2994829 A1 | 2/2017 |
| CA | 3003728 A1 | 5/2017 |
| CA | 3076337 A1 | 3/2019 |

(Continued)

OTHER PUBLICATIONS

Okamoto S, et al. Improved expression and reactivity of transduced tumor-specific TCRs in human lymphocytes by specific silencing of endogenous TCR. Cancer Res. Dec. 1, 2009;69(23):9003-11. doi: 10.1158/0008-5472.CAN-09-1450. Epub Nov. 10, 2009. PMID: 19903853. (Year: 2009).*

(Continued)

*Primary Examiner* — Janet L Andres
*Assistant Examiner* — Carol Ann Chase
(74) *Attorney, Agent, or Firm* — Sterne, Kessler, Goldstein & Fox P.L.L.C.

(57) ABSTRACT

The present disclosure is directed recombinant T cell receptors capable of binding a CCND1 epitope and nucleic acid molecules encoding the same. In some aspects, the nucleic acid molecules further comprise a second nucleotide sequence, wherein the second nucleotide sequence or the polypeptide encoded by the second nucleotide sequence inhibits the expression of an endogenous TCR. Other aspects of the disclosure are directed to vectors comprising the nucleic acid molecule and cells comprising the recombinant TCR, the nucleic acid molecule, or the vector. Still other aspects of the disclosure are directed to methods of using the same. In some aspects, the methods comprise treating a cancer in a subject in need thereof.

19 Claims, 6 Drawing Sheets

Specification includes a Sequence Listing.

(56)                    References Cited

FOREIGN PATENT DOCUMENTS

| CN | 109312331 A | 2/2019 |
| JP | 2016526883 A | 11/2018 |
| WO | WO-2014201021 A2 | 12/2014 |
| WO | WO-2017185169 A1 | 11/2017 |
| WO | WO-2018197492 A1 | 11/2018 |
| WO | WO-2019034703 A2 | 2/2019 |

OTHER PUBLICATIONS

Musgrove EA, Caldon CE, Barraclough J, Stone A, Sutherland RL. Cyclin D as a therapeutic target in cancer. Nat Rev Cancer. Jul. 7, 2011;11(8):558-72. doi: 10.1038/nrc3090. PMID: 21734724. (Year: 2011).*

Anczurowski, M., et al., "Mechanisms underlying the lack of endogenous processing and CLIP-mediated binding of the invariant chain by HLA-DP84Gly," Sci. Rep. 8:4804, Springer, Germany (Mar. 2018).

Butler, M.O., et al., "Ex vivo expansion of human CD8+ T cells using autologous CD4+ T cell help," PloS One 7:e30229, PLOS, United States (Jan. 2012).

Huang, S., and Kamihira, M., "Development of hybrid viral vectors for gene therapy," Biotechnol. Adv. 31(2):208-23, Elsevier, Netherlands (Oct. 2012).

International Search Report and Written Opinion for International Application PCT/IB2020/057172, Canadian Intellectual Property Office, Canada, mailed on Oct. 16, 2020, 11 pages.

Yamashita, Y., et al., "HLA-DP84Gly constitutively presents endogenous peptides generated by the class I antigen processing pathway," Nat. Commun. 8:15244, Springer, Germany (May 2017).

Chen, B., et al., "Cell cycle inhibition by an anti-cyclin D1 antibody chemically modified for intracellular delivery," *Cancer Letters*, 244(1):71-75, Elsevier, Netherlands (Nov. 2006).

* cited by examiner

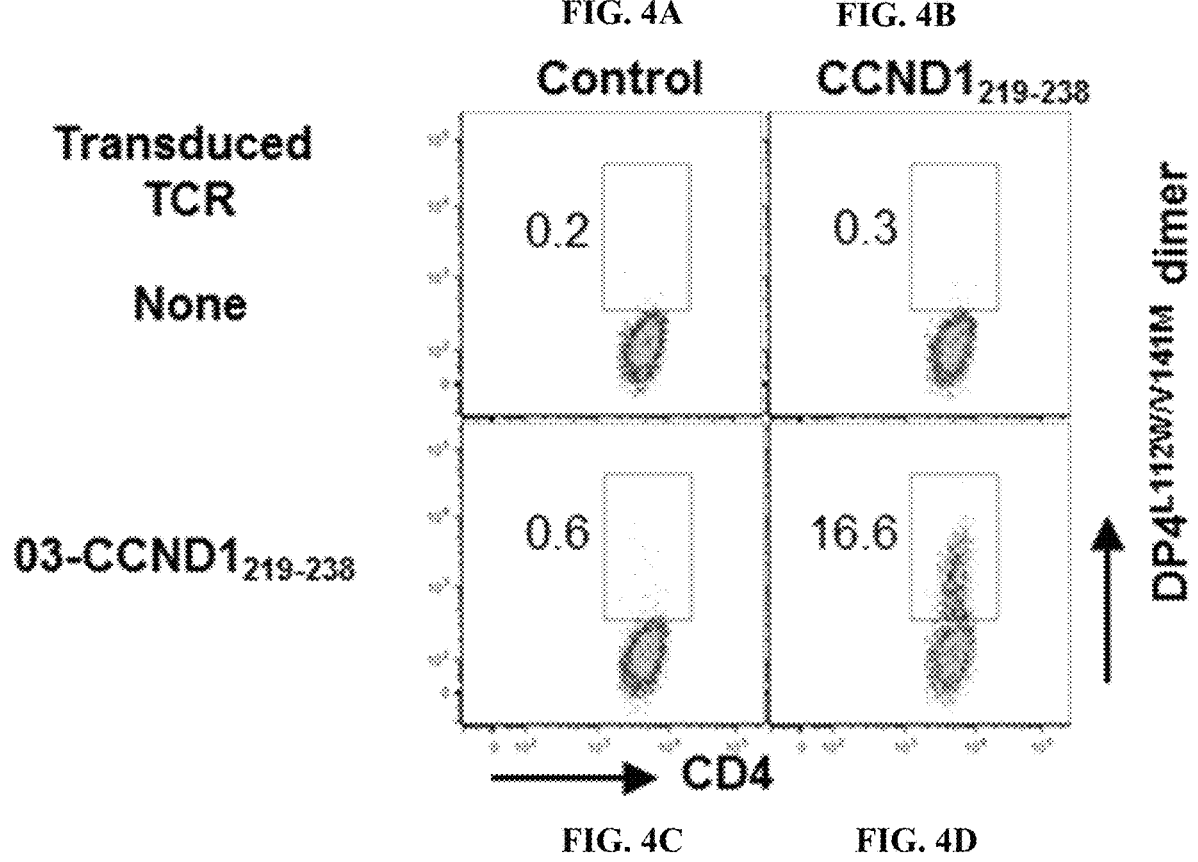
FIG. 4A · FIG. 4B · FIG. 4C · FIG. 4D

T CELL RECEPTORS AND METHODS OF USE THEREOF

CROSS REFERENCE TO RELATED APPLICATIONS

This PCT application claims the priority benefit of U.S. Provisional Application No. 62/880,504, filed Jul. 30, 2019, which is incorporated herein by reference in its entirety.

REFERENCE TO SEQUENCE LISTING SUBMITTED ELECTRONICALLY VIA EFS-WEB

The content of the electronically submitted sequence listing (Name: 4285-013PC01_SL_ST25.txt, Size: 22,576 bytes; and Date of Creation: Jul. 28, 2020) is incorporated herein by reference in its entirety.

FIELD OF THE DISCLOSURE

The present disclosure provides recombinant T cell receptors ("TCRs") that specifically bind human G1/S-specific cyclin-D1 (CCND1) and uses thereof.

BACKGROUND OF THE DISCLOSURE

Immunotherapy has emerged as a critical tool in the battle against a variety of diseases, including cancer. T cell therapies are at the forefront of immunotherapeutic development, and adoptive transfer of antitumor T cells has been shown to induce clinical responses in cancer patients. Though many T cell therapies target mutated tumor antigens, the vast majority of neoantigens are not shared and are unique to each patient.

Potential non-mutated antigens outnumber mutated antigens by multiple orders of magnitude. The elucidation of T cell epitopes derived from shared antigens may facilitate the robust development of efficacious and safe adoptive T cell therapies that are readily available to a larger cohort of cancer patients. However, the sheer number of non-mutated antigens and the high polymorphism of HLA genes may have hampered comprehensive analyses of the specificity of antitumor T cell responses toward non-mutated antigens.

SUMMARY OF THE DISCLOSURE

Certain aspects of the present disclosure are directed to a nucleic acid molecule comprising (i) a first nucleotide sequence encoding a recombinant T cell receptor (TCR) or an antigen binding portion thereof that specifically binds human G1/S-specific cyclin-D1 (CCND1) ("anti-CCND1 TCR"); and (ii) a second nucleotide sequence, wherein the second nucleotide sequence or the polypeptide encoded by the second nucleotide sequence inhibits the expression of an endogenous TCR, wherein the anti-CCND1 TCR cross competes for binding to human CCND1 with a reference TCR, which comprises an alpha chain and a beta chain, and wherein the alpha chain comprises an amino acid sequence as set forth in SEQ ID NO: 1 and the beta chain comprises an amino acid sequence as set forth in SEQ ID NO: 2.

Certain aspects of the present disclosure are directed to a nucleic acid molecule comprising (i) a first nucleotide sequence encoding a recombinant T cell receptor (TCR) or an antigen binding portion thereof that specifically binds human CCND1 ("anti-CCND1 TCR"); and (ii) a second nucleotide sequence, wherein the second nucleotide sequence or the polypeptide encoded by the second nucleotide sequence inhibits the expression of an endogenous TCR, wherein the anti-CCND1 TCR binds the same epitope or an overlapping epitope of human CCND1 as a reference TCR, which comprises an alpha chain and a beta chain, wherein the alpha chain comprises an amino acid sequence as set forth in SEQ ID NO: 1 and the beta chain comprises an amino acid sequence as set forth in SEQ ID NO: 2.

In some aspects, the anti-CCND1 TCR binds to an epitope of CCND1 consisting of an amino acid sequence as set forth in SEQ ID NO: 13. In some aspects, the epitope is complexed with an HLA class II molecule. In some aspects, the HLA class II molecule is an HLA-DP, HLA-DQ, or HLA-DR allele, or any combination thereof. In some aspects, the HLA class II molecule is an HLA-DP allele. In some aspects, the HLA class II molecule is an HLA-DP4 allele.

In some aspects, the anti-CCND1 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the alpha chain CDR3 comprises an amino acid sequence as set forth in SEQ ID NO: 7.

In some aspects, the beta chain CDR3 of the anti-CCND1 TCR comprises an amino acid sequence as set forth in SEQ ID NO: 10.

In some aspects, the anti-CCND1 TCR comprises an alpha chain and a beta chain, wherein the alpha chain comprises a variable region comprising an alpha chain CDR1, an alpha chain CDR2, and an alpha chain CDR3; and wherein the beta chain comprises variable domain comprising a beta chain CDR1, a beta chain CDR2, and a beta chain CDR3; wherein the beta chain CDR3 of the anti-CCND1 TCR comprises an amino acid sequence as set forth in SEQ ID NO: 10.

In some aspects, the alpha chain CDR3 of the anti-CCND1 TCR comprises an amino acid sequence as set forth in SEQ ID NO: 7. In some aspects, the alpha chain CDR1 of the anti-CCND1 TCR comprises an amino acid sequence as set forth in SEQ ID NO: 5. In some aspects, the beta chain CDR1 of the anti-CCND1 TCR comprises an amino acid sequence as set forth in SEQ ID NO: 8. In some aspects, the alpha chain CDR2 of the anti-CCND1 TCR comprises an amino acid sequence as set forth in SEQ ID NO: 6. In some aspects, the beta chain CDR2 of the anti-CCND1 TCR comprises an amino acid sequence as set forth in SEQ ID NO: 9.

In some aspects, the alpha chain variable domain of the anti-CCND1 TCR comprises an amino acid sequence of a variable domain present in the amino acid sequence set forth SEQ ID NO: 1. In some aspects, the beta chain variable domain of the anti-CCND1 TCR comprises an amino acid sequence of a variable domain present in the amino acid sequence set forth SEQ ID NO: 2.

In some aspects, the alpha chain of the anti-CCND1 TCR further comprises a constant region, wherein the constant region is different from endogenous constant region of the alpha chain. In some aspects, the alpha chain of the anti-CCND1 TCR further comprises a constant region, wherein the alpha chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 1. In some aspects, the alpha chain constant region comprises an amino acid sequence comprising at least 1, at least 2, at least 3, at least 4, or at least 5 amino acid substitutions relative to a constant region present in the amino acid sequence set forth SEQ ID NO: 1.

In some aspects, the beta chain of the anti-CCND1 TCR further comprises a constant region, wherein the constant region is different from endogenous constant regions of the beta chain. In some aspects, the beta chain of the anti-CCND1 TCR further comprises a constant region, wherein the beta chain constant region comprises an amino acid sequence having at least about 85%, at least about 90%, at least about 95%, at least about 96%, at least about 97%, at least about 98%, or at least about 99% sequence identity to a constant region present in the amino acid sequence set forth SEQ ID NO: 2. In some aspects, the beta chain constant region comprises an amino acid sequence comprising at least 1, at least 2, at least 3, at least 4, or at least 5 amino acid substitutions relative to a constant region present in the amino acid sequence set forth SEQ ID NO: 2.

In some aspects, the alpha chain of the anti-CCND1 TCR comprises an amino acid sequence as set forth in SEQ ID NO: 1. In some aspects, the beta chain of the anti-CCND1 TCR comprises an amino acid sequence as set forth in SEQ ID NO: 2.

In some aspects, the second nucleotide sequence is one or more siRNAs that reduce the expression of endogenous TCRs. In some aspects, the one or more siRNAs are complementary to a target sequence within a nucleotide sequence encoding a constant region of the endogenous TCRs. In some aspects, the one or more siRNAs comprise one or more nucleotide sequences selected from the group consisting of SEQ ID NOs: 53-56.

In some aspects, the anti-CCND1 TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

In some aspects, the alpha chain comprises a signal peptide, the beta chain comprises a signal peptide, or both the alpha chain and the beta chain comprise a single peptide. In some aspects, the signal peptide comprises an amino acid sequence selected from the amino acid sequences set forth in SEQ ID NOs: 20-22 and any combination thereof.

Certain aspects of the present disclosure are directed to a vector comprising a nucleic acid molecule disclosed herein. In some aspects, the vector is a viral vector, a mammalian vector, or bacterial vector. In some aspects, the vector is a retroviral vector. In some aspects, the vector is selected from the group consisting of an adenoviral vector, a lentivirus, a Sendai virus vector, a baculoviral vector, an Epstein Barr viral vector, a papovaviral vector, a vaccinia viral vector, a herpes simplex viral vector, a hybrid vector, and an adeno associated virus (AAV) vector. In some aspects, the vector is a lentivirus.

Certain aspects of the present disclosure are directed to a T cell receptor (TCR) or an antigen binding portion thereof comprising the alpha chain variable domain of an anti-CCND1 TCR disclosed herein and the beta chain variable domain of an anti-CCND1 TCR disclosed herein.

Certain aspects of the present disclosure are directed to a recombinant T cell receptor (TCR) or an antigen binding portion thereof that specifically binds human CCND1 ("an anti-CCND1 TCR"), which cross competes for binding to human CCND1 with a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-CCND1 TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to a constant region present in the amino acid sequence set forth in SEQ ID NO: 1 or the beta chain constant region comprises an amino acid sequence having a least 1, at least 2, at least 3, at least 4, or at least 5 amino acid substitutions relative to a constant region present in the amino acid sequence of SEQ ID NO: 2.

Certain aspects of the present disclosure are directed to a recombinant T cell receptor (TCR) or an antigen binding portion thereof that specifically binds human CCND1 ("an anti-CCND1 TCR"), which binds the same epitope or an overlapping epitope of human CCND1 as a reference TCR; wherein the reference TCR comprises an alpha chain and a beta chain, and wherein the alpha chain comprises an amino acid sequence as set forth in SEQ ID NO: 1 and the beta chain comprises an amino acid sequence as set forth in SEQ ID NO: 2; and wherein the anti-CCND1 TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to a constant region present in the amino acid sequence set forth in SEQ ID NO: 1 or the beta chain constant region comprises an amino acid sequence having a least 1, at least 2, at least 3, at least 4, or at least 5 amino acid substitutions relative to a constant region present in the amino acid sequence set forth in SEQ ID NO: 2.

In some aspects, the anti-CCND1 TCR binds to an epitope of CCND1 consisting of an amino acid sequence as set forth in SEQ ID NO: 13. In some aspects, the epitope is complexed with an HLA class II molecule. In some aspects, the HLA class H molecule is an HLA-DP, HLA-DQ, or HLA-DR allele, or any combination thereof. In some aspects, the HLA class II molecule is an HLA-DP allele. In some aspects, the HLA class II molecule is selected from an HLA-DP4 allele.

In some aspects, the alpha chain of the anti-CCND1 TCR comprises a variable domain comprising an alpha chain CDR1, an alpha chain CDR2, and an alpha chain CDR3; and wherein the beta chain of the anti-CCND1 TCR comprises variable domain comprising a beta chain CDR1, a beta chain CDR2, and a beta chain CDR3; wherein the alpha chain CDR3 of the anti-CCND1 comprises an amino acid sequence as set forth in SEQ ID NO: 7. In some aspects, the beta chain CDR3 of the anti-CCND1 TCR comprises an amino acid sequence as set forth in SEQ ID NO: 10.

In some aspects, the alpha chain of the anti-CCND1 TCR comprises a variable domain comprising an alpha chain CDR1, an alpha chain CDR2, and an alpha chain CDR3; wherein the beta chain of the anti-CCND1 TCR comprises a variable domain comprising a beta chain CDR1, a beta chain CDR2, and a beta chain CDR3; and wherein the beta chain CDR3 of the anti-CCND1 TCR comprises an amino acid sequence as set forth in SEQ ID NO: 10. In some aspects, the alpha chain CDR3 of the anti-CCND1 TCR comprises an amino acid sequence as set forth in SEQ ID NO: 7.

5

In some aspects, the alpha chain CDR1 of the anti-CCND1 TCR comprises an amino acid sequence as set forth in SEQ ID NO: 5, In some aspects, the beta chain CDR1 of the anti-CCND1 TCR comprises an amino acid sequence as set forth in SEQ ID NO: 8. In some aspects, the alpha chain CDR2 of the anti-CCND1 TCR comprises an amino acid sequence as set forth in SEQ ID NO: 6. In some aspects, the beta chain CDR2 of the anti-CCND1 TCR comprises an amino acid sequence as set forth in SEQ ID NO: 9.

In some aspects, the alpha chain variable domain of the anti-CCND1 TCR comprises an amino acid sequence of a variable domain present in the amino acid sequence set forth in SEQ ID NO: 1. In some aspects, the beta chain variable domain of the anti-CCND1 TCR comprises an amino acid sequence of a variable domain present in the amino acid sequence set forth in SEQ ID NO: 2.

In some aspects, the alpha chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 1.

In some aspects, the beta chain constant region comprises an amino acid sequence having at least about 85%, at least about 90%, at least about 95%, at least about 96%, at least about 97%, at least about 98%, or at least about 99% sequence identity to the amino acid sequence of a constant region present in the amino acid sequence set forth in SEQ ID NO: 2.

In some aspects, the alpha chain of the anti-CCND1 TCR comprises an amino acid sequence as set forth in SEQ ID NO: 1. In some aspects, the beta chain of the anti-CCND1 TCR comprises an amino acid sequence as set forth in SEQ ID NO: 2.

In some aspects, the alpha chain comprises a signal peptide, the beta chain comprises a signal peptide, or both the alpha chain and the beta chain comprise a single peptide. In some aspects, the signal peptide comprises an amino acid sequence selected from the amino acid sequences set forth in SEQ ID NOs: 20-22 and any combination thereof.

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein.

In some aspects, the first antigen-binding domain comprises a single chain variable fragment ("scFv"). In some aspects, the second antigen-binding domain binds specifically to a protein expressed on the surface of a T cell. In some aspects, the second antigen-binding domain binds specifically to CD3. In some aspects, the second antigen-binding domain comprises an scFv. In some aspects, the first antigen-binding domain and the second antigen-binding domain are linked or associated by a covalent bond. In some aspects, the first antigen-binding domain and the second antigen-binding domain are linked by a peptide bond.

Certain aspects of the present disclosure are directed to a cell comprising a nucleic acid molecule disclosed herein, a vector disclosed herein, a TCR disclosed herein, a recombinant TCR disclosed herein, or a bispecific TCR disclosed herein. In some aspects, the cell further expresses CD3.

In some aspects, the cell is selected from the group consisting of a T cell, a natural killer (NK) cell, an natural killer T (NKT) cell, or an ILC cell.

Certain aspects of the present disclosure are directed to a method of treating a cancer in a subject in need thereof, comprising administering to the subject a cell disclosed herein. In some aspects, the cancer is selected from the group consisting of melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers.

In some aspects, the cancer is relapsed or refractory. In some aspects, the cancer is locally advanced. In some aspects, the cancer is advanced. In some aspects, the cancer is metastatic.

In some aspects, the cells are obtained from the subject. In some aspects, the cells are obtained from a donor other than the subject.

In some aspects, the subject is preconditioned prior to the administering of the cells. In some aspects, the preconditioning comprises administering to the subject a chemotherapy, a cytokine, a protein, a small molecule, or any combination thereof. In some aspects, the preconditioning comprises administering an interleukin. In some aspects, the preconditioning comprises administering IL-2, IL-4, IL-7, IL-9, IL-15, IL-21, or any combination thereof. In some aspects, the preconditioning comprises administering a preconditioning agent selected from the group consisting of cyclophosphamide, fludarabine, vitamin C, an AKT inhibitor, ATRA, Rapamycin, or any combination thereof. In some aspects, the preconditioning comprises administering cyclophosphamide, fludarabine, or both.

Certain aspects of the present disclosure are directed to a method of engineering an antigen-targeting cell, comprising transducing a cell collected from a subject in need of a T cell therapy with a nucleic acid molecule disclosed herein or a vector disclosed herein. In some aspects, the antigen-targeting cell further expresses CD4. In some aspects, the cell is a T cell or a natural killer (NK) cell.

Certain aspects of the present disclosure are directed to an HLA class II molecule complexed to a peptide, wherein the HLA class II molecule comprises an alpha chain and a beta chain; and wherein the peptide consists of an amino acid sequence as set forth in SEQ ID NO: 13. In some aspects, the HLA class II molecule is an HLA-DP, HLA-DQ, or HLA-DR allele, or any combination thereof. In some aspects, the HLA class II molecule is an HLA-DP allele. In some aspects, the HLA class II molecule is an HLA-DQ allele. In some aspects, the HLA class II molecule is an HLA-DR allele.

In some aspects, the HLA class II molecule is a monomer. In some aspects, the HLA class II molecule is a dimer. In some aspects, the HLA class II molecule is a trimer. In some aspects, the HLA class II molecule is a tetramer. T In some aspects, the HLA class II molecule is a pentamer.

Certain aspects of the present disclosure are directed to an antigen presenting cell (APC), comprising an HLA class II molecule disclosed herein. In some aspects, the HLA class II molecule is expressed on the surface of the APC.

Certain aspects of the present disclosure are directed to a method of enriching a target population of T cells obtained from a human subject, comprising contacting the T cells with an HLA class H molecule disclosed herein or an APC disclosed herein, wherein following the contacting, the enriched population of T cells comprises a higher number of T cells capable of binding the HLA class H molecule relative to the number of T cells capable of binding the HLA class II molecule prior to the contacting.

Certain aspects of the present disclosure are directed to a method of enriching a target population of T cells obtained from a human subject, comprising contacting the T cells in vitro with a peptide, wherein the peptide consists of an amino acid sequence as set forth in SEQ ID NO: 13, wherein following the contacting, the enriched population of T cells comprises a higher number of T cells capable of targeting a tumor cell relative to the number of T cells capable of targeting a tumor cell prior to the contacting. In some aspects, the T cells obtained from the human subject are tumor infiltrating lymphocytes (TIL).

Certain aspects of the present disclosure are directed to a method of treating a tumor in a subject in need thereof, comprising administering to the subject an enriched T cells disclosed herein.

Certain aspects of the present disclosure are directed to a method of enhancing cytotoxic T cell-mediated targeting of cancer cells in a subject afflicted with a cancer, comprising administering to the subject a peptide having an amino acid sequence as set forth in SEQ ID NO: 13.

Certain aspects of the present disclosure are directed to a cancer vaccine comprising a peptide having an amino acid sequence as set forth in SEQ ID NO: 13.

Certain aspects of the present disclosure are directed to a method of selecting a T cell capable of targeting a tumor cell, comprising contacting a population of isolated T cells in vitro with a peptide, wherein the peptide consists of an amino acid sequence as set forth in SEQ ID NO: 13.

In some aspects, the T cell is a tumor infiltrating lymphocytes (TIL).

03-CCND1$_{219-238}$ were cloned from $DP4^{L112W/V141M}$ dimer-positive cells, reconstituted in TCR-defective Jurkat 76/CD4 cells, and stained by the respective $DP4^{L112W/V141M}$ dimers.

Figure 3:
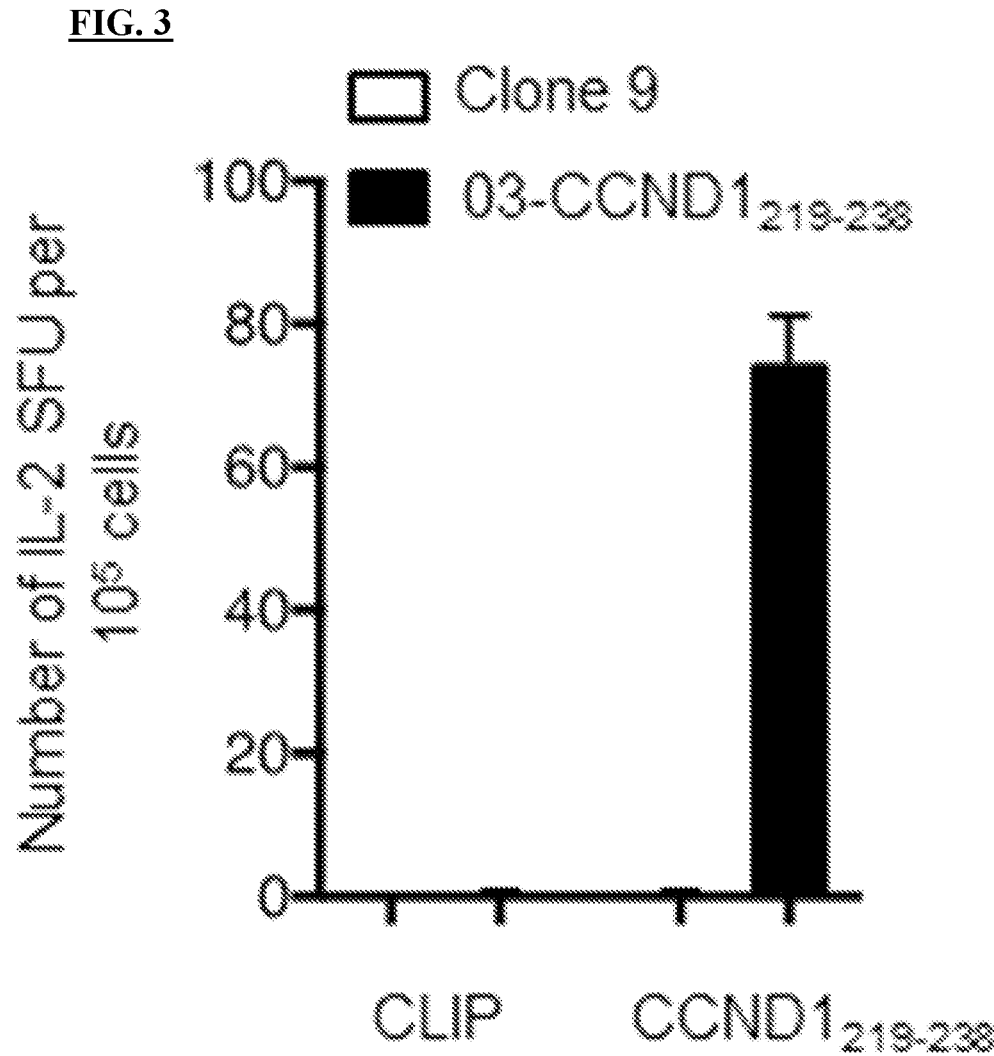

FIG. 3 is a bar graph illustrating the results of IL-2 EPISPOT assays of 03-CCND1$_{219-238}$ stimulated by aAPCs pulsed with CCND1$_{219-238}$ peptides in IL-2 ELISPOT assays. DP4/WT1 (clone 9) TCR was used as a negative control. At least 2 independent experiments were performed. Bars and error bars represent the mean±SD of results in triplicate experiments.

Figure 4E:
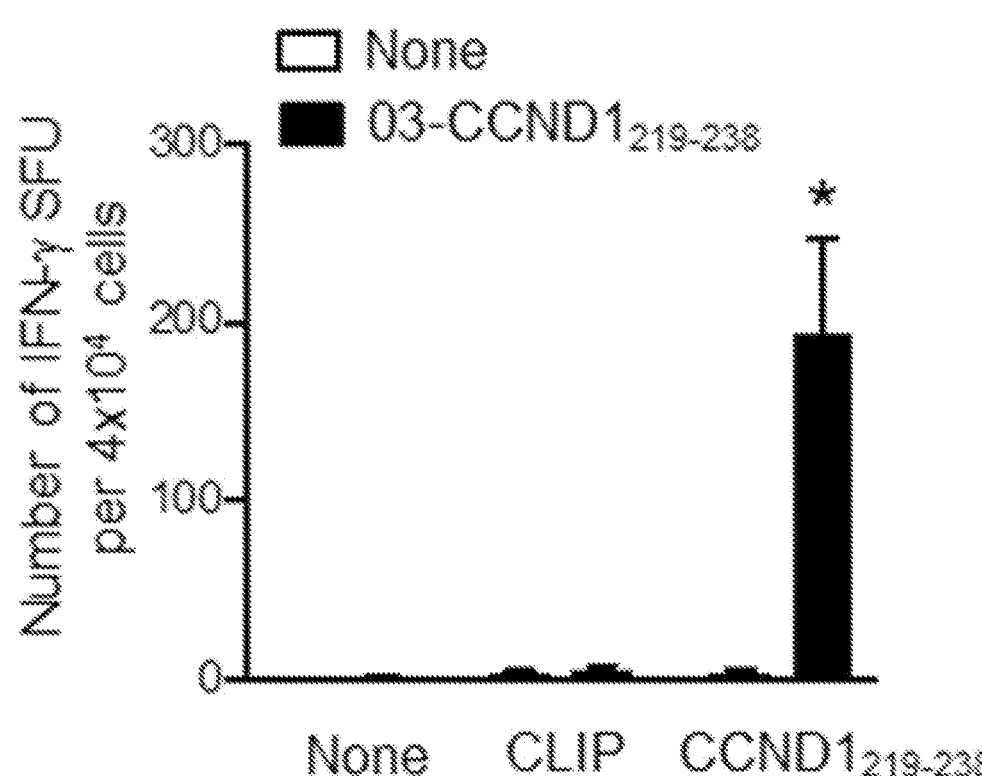

FIGS. 4A-4E are graphical representations of data showing that DP4-restricted CCND1$_{219-238}$ TCRs isolated from $DP4^{L112W/V141M}$ dimer-positive cells and reconstituted in human primary CD4$^+$ T cells were functional in a DP4-restricted and antigen-specific manner. 03-CCND1$_{219-238}$ were retrovirally transduced into human primary CD4$^+$ T cells and stained with the respective $DP4^{L112W/V141M}$ dimers. *P<0.05 by Student's t-test. Bars and error bars represent the mean±SD of results in triplicate experiments (FIG. 4E).

Figure 5A:
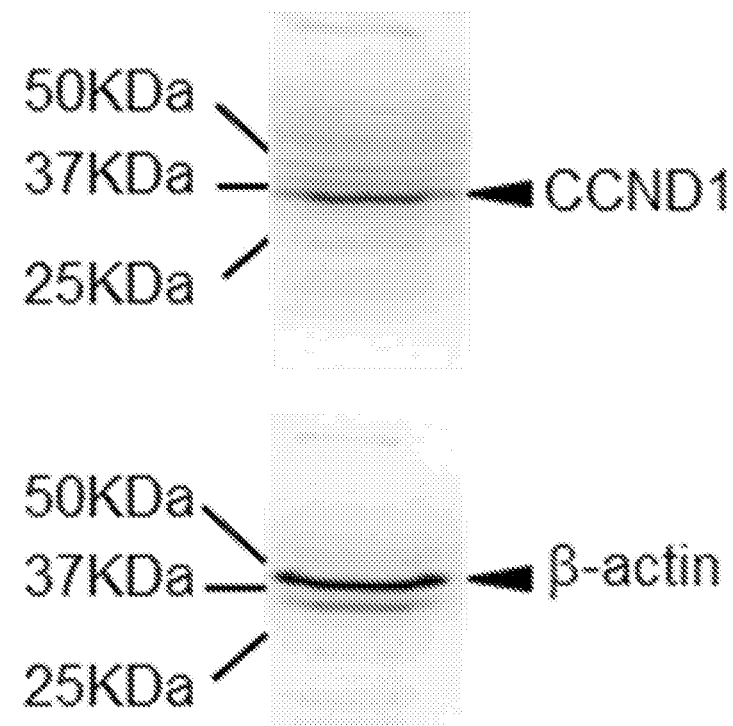
Figure 5B:
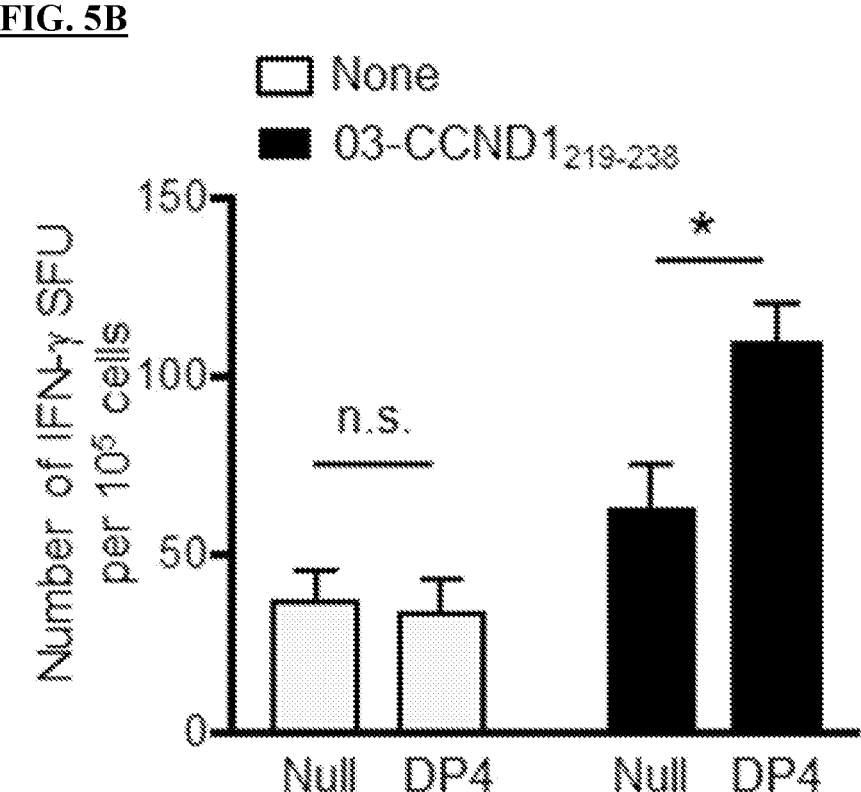

FIGS. 5A-5B present data showing that DP4-restricted CCND1$_{219}$-238 TCRs cloned from melanoma patients recognized peptides endogenously processed and presented by K562-based aAPCs. FIG. 5A is an image of a Western blot analysis showing CCND1 endogenously expressed in K562-derived aAPC cells. FIG. 5B is a bar graph showing the results of IFN-γ ELISPOT assays of human primary T cells retrovirally transduced with 03-CCND1$_{219-238}$ and stimulated with peptide-unpulsed HLA-null or DP4-aAPCs. *, P<0.05 by Student's t-test. Bars and error bars represent the mean±SD of results in triplicate experiments.

DETAILED DESCRIPTION OF THE DISCLOSURE

The present disclosure is directed to TCRs or antigen binding portions thereof that specifically bind to an epitope on CCND1, nucleic acid molecules that encode the same, and cells that comprise the TCR or the nucleic acid molecule. Some aspects of the present disclosure are directed to methods of treating a cancer in a subject in need thereof. Other aspects of the present disclosure are directed to HLA class II molecules complexed to a peptide comprising the epitope of CCND1.

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "T cell receptor" (TCR), as used herein, refers to a heteromeric cell-surface receptor capable of specifically interacting with a target antigen. As used herein, "TCR" includes but is not limited to naturally occurring and non-naturally occurring TCRs; full-length TCRs and antigen binding portions thereof; chimeric TCRs; TCR fusion constructs; and synthetic TCRs. In human, TCRs are expressed on the surface of T cells, and they are responsible for T cell recognition and targeting of antigen presenting cells. Antigen presenting cells (APCs) display fragments of foreign proteins (antigens) complexed with the major histocompatibility complex (MHC; also referred to herein as complexed with an HLA molecule, e.g., an HLA class II molecule). A TCR recognizes and binds to the peptide:HLA complex and recruits CD8 (for MHC Class I molecules) or CD4 (for MHC class II molecules), activating the TCR. The activated TCR initiates downstream signaling and an immune response, including the destruction of the EPC.

In general, a TCR can comprise two chains, an alpha chain and a beta chain (or less commonly a gamma chain and a delta chain), interconnected by disulfide bonds. Each chain comprises a variable domain (alpha chain variable domain and beta chain variable domain) and a constant region (alpha chain constant region and beta chain constant region). The variable domain is located distal to the cell membrane, and the variable domain interacts with an antigen. The constant region is located proximal to the cell membrane. A TCR can further comprises a transmembrane region and a short cytoplastnic tail. As used herein, the term "constant region" encompasses the transmembrane region and the cytoplasmic tail, when present, as well as the traditional "constant region."

The variable domains can be further subdivided into regions of hypervariability, termed complementarity determining regions (CDRs), interspersed with regions that are more conserved, termed framework regions (FR). Each alpha chain variable domain and beta chain variable domain comprises three CDRs and four FRs: FR1, CDR1, FR2, CDR2, FR3, CDR3, FR4. Each variable domain contains a binding domain that interacts with an antigen. Though all three CDRs on each chain are involved in antigen binding, CDR3 is believed to be the primary antigen binding region, while CDR1 and CDR2 are believed to primarily recognize the HLA molecule.

Where not expressly stated, and unless the context indicates otherwise, the term "TCR" also includes an antigen-binding fragment or an antigen-binding portion of any TCR disclosed herein, and includes a monovalent and a divalent fragment or portion, and a single chain TCR. The term "TCR" is not limited to naturally occurring TCRs bound to the surface of a T cell. As used herein, the term "TCR" further refers to a TCR described herein that is expressed on the surface of a cell other than a T cell (e.g., a cell that naturally expresses or that is modified to express CD4, as described herein), or a TCR described herein that is free from a cell membrane (e.g., an isolated TCR or a soluble TCR).

An "antigen binding molecule," "portion of a TCR," or "TCR fragment" refers to any portion of an TCR less than the whole. An antigen binding molecule can include the antigenic CDRs.

An "antigen" refers to any molecule, e.g., a peptide, that provokes an immune response or is capable of being bound by a TCR. An "epitope," as used herein, refers to a portion of a polypeptide that provokes an immune response or is capable of being bound by a TCR. The immune response may involve either antibody production, or the activation of specific immunologically-competent cells, or both. A person of skill in the art would readily understand that any macromolecule, including virtually all proteins or peptides, can serve as an antigen. An antigen and/or an epitope can be endogenously expressed, i.e. expressed by genomic DNA, or can be recombinantly expressed. An antigen and/or an epitope can be specific to a certain tissue, such as a cancer cell, or it can be broadly expressed. In addition, fragments of larger molecules can act as antigens. In one aspect, antigens are tumor antigens. An epitope can be present in a longer polypeptide (e.g., in a protein), or an epitope can be present as a fragment of a longer polypeptide. In some aspects, an epitope is complexed with a major histocompatibility complex (MHC; also referred to herein as complexed with an HLA molecule, e.g., an HLA class 1 molecule).

"CCND1," "G1/S-specific cyclin-D1," "B-cell lymphoma 1 protein," "BCL-1," or "PRAD1," as used herein, refers to a human regulatory component of the cyclin D1-CDK4 (DC) complex that phosphorylates and inhibits members of the retinoblastoma (RB) protein family including RB1 and regulates the cell-cycle during G1/S transition, Phosphorylation of RB1 allows dissociation of the transcription factor E2F from the RB/E2F complex and the subsequent transcription of E2F target genes which are responsible for the progression through the G1 phase. CCND1 is also involved in hypophosphorylation of RB1 in early G1 phase. Cyclin D-CDK4 complexes are major integrators of various mitogenenic and antimitogenic signals. CCND1 is also a substrate for SMAD3, phosphorylating SMAD3 in a cell-cycle-dependent manner and repressing its transcriptional activity. CCND1 is also a component of the ternary complex, cyclin D1/CDK4/CDKN1B, required for nuclear translocation and activity of the cyclin D-CDK4 complex, and CCND1 exhibits transcriptional corepressor activity with INSM1 on the NEUROD1 and INS promoters in a cell cycle-independent manner. Mutations, amplification, and overexpression of CCND1, which alter cell cycle progression, are observed frequently in a variety of tumors and may contribute to tumorigenesis.

As used herein, CCND1 refers to not only the full-length canonical sequence, but also variants and fragments thereof. The amino acid sequence of CCND1 (SEQ ID NO: 16) is provided in Table 1 (UniProtKB-P24385).

alpha chain and a beta chain. In general, naturally occurring alpha chains and beta chains each comprise a transmembrane domain, which anchors the alpha/beta chain to the cell surface, and an extracellular domain, which carries the antigen and interacts with a TCR and/or CD4 expressed on a T cell.

Both the MEW Class II alpha and beta chains are encoded by the HLA gene complex. The HLA complex is located within the 6p21.3 region on the short arm of human chromosome 6 and contains more than 220 genes of diverse function. The HLA gene complex is highly variant, with over 20,000 HLA alleles and related alleles, including over 250 AMC class II alpha chain alleles and 5,000 MHC class II beta chain alleles, known in the art, encoding thousands of MHC class II proteins (see, e.g., hla.alleles.org, last visited May 20, 2019, which is incorporated by reference herein in its entirety). For example one such HLA-DP allele, DP4 is the most frequently found allele in many ethnic groups.

Three loci in the HLA complex encode MEW Class II proteins: HLA-DP, HLA-DQ, and HLA-DR. HLA-DO and HLA-DM encode proteins that associate with the MHC class II molecule and support its configuration and function.

When the MHC class II molecule is complexed with an antigen peptide, the 10-30 amino acid long antigen peptide binds the peptide-binding groove and is presented extracellularly to CD4+ cells. Both the alpha- and beta-chains fold into two separate domains; alpha-1 and alpha-2 for the alpha polypeptide, and beta-1 and beta-2 for the beta polypeptide. The open-ended peptide-binding groove which holds the presented antigen is found between the alpha-1 and beta-1 domains. Upon interaction with a CD4+ T cell, the MHC class II complex interacts with a T cell receptor (TCR) expressed on the surface of the T cell. In addition, the beta chain of the MHC class II molecule weakly interacts ($K_D > 2$ mM) with CD4 expressed on the surface of the T cell. The

TABLE 1

| CCND1 Amino Acid Sequence | |
|---|---|
| SEQ ID NO: | CCND1 Amino Acid Sequence |
| 16 | MEHQLLCCEVETIRRAYPDANLLNDRVLRAMLKAEETCAPSVSYFKCVQKEVLPSMRKIV<br>ATWMLEVCEEQKCEEEVFPLAMNYLDRFLSLEPVKKSRLQLLGATCMFVASKMKETIPLT<br>AEKLCIYTDNSIRPEELLQMELLLVNKLKWNLAAMTPHDFIEHFLSKMPEAEENKQIIRK<br>HAQTFVALCATDVKFISNPPSMVAAGSVVAAVQGLNLRSPNNFLSYYRLTREMSRVIKCD<br>PDCLRACQEQIEALLESSLRQAQQNMDPKAAEEEEEEEEEVDLACTPTDVRDVDI |

The term "HLA," as used herein, refers to the human leukocyte antigen. HLA genes encode the major histocompatibility complex (MHC) proteins in humans. MHC proteins are expressed on the surface of cells, and are involved in activation of the immune response. HLA class II genes encode MHC class II proteins which are expressed on the surface of professional antigen presenting cells (APCs). Non-limiting examples of professional APCs include monocytes, macrophages, dendritic cells (DCs), and B lymphocytes. Some endothelial and epithelial cells can also express MHC class II molecules after inflammatory signals are activated. Humans lacking functional MHC class II molecules are extremely susceptible to an array of infectious diseases and typically die at a young age.

As used herein, an "HLA class II molecule" or "MHC class II molecule" refers to a protein product of a wild-type or variant HLA class II gene encoding an MEW class II molecule. Accordingly, "HLA class II molecule" and "MHC class II molecule" are used interchangeably herein. A typical MHC Class II molecule comprises two protein chains: an canonical CD4 amino acid sequence (UniProt-P01730) is provided in Table 2 (SEQ ID NO: 17).

TABLE 2

| Human CD4 Amino Acid Sequence |
|---|
| MNRGVPFRHLLLVLQLALLPAATQGKEVVLGKKGDTVELTCTASQKKS<br>IQFHWKNSNQIKILGNQGSFLTKGPSELNDRADSRPELWDQGNFPLII<br>KNLKIEDSDTYICEVEDQKEEVQLLVFQLTANSDTHLLQGQSLTLTLE<br>SPPGSSPSVQCRSPRGKNIQGGKTLSVSQLELQDSGTWTCTVLQNQKK<br>VEFKIDIVVLAFQKASSIVYKKEGEQVEFSFPLAFTVEKLTGSGELWW<br>QAERASSSKSWITEDLKNKEVSVKRVTQDPKLQMGEKLPLHLTLPQAL<br>PQYAGSGNLTLALEAKTQKLHQEVNLVVMRATQLQKNLTCEVWGPTSP<br>KLMLSLKLENKEAKVSKREKAVWVLNPEAGMWQCLLSDSGQVLLESNI<br>KVLPTWSTPVQPMALIVLGGVAGLLLFIGLGIFFCVPQRHRRRQAERM<br>SQIKRLLSEKKTCQCPHRFQKTCSPI (SEQ ID NO: 17) |

The term "autologous" refers to any material derived from the same individual to which it is later to be re-introduced. For example, an autologous T cell therapy comprises administering to a subject a T cell that was isolated from the same subject. The term "allogeneic" refers to any material derived from one individual which is then introduced to another individual of the same species. For example, an allogeneic T cell transplantation comprises administering to a subject a T cell that was obtained from a donor other than the subject.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some aspects, the methods of the present invention can be used to reduce the minor size of a tumor derived from, for example, bone cancer, renal cancer, prostate cancer, breast cancer, colon cancer, lung cancer, cutaneous or intraocular malignant melanoma, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. The particular cancer can be responsive to chemo- or radiation therapy or the cancer can be refractory.

A refractory cancer refers to a cancer that is not amendable to surgical intervention, and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" or "progressive disease," which can be abbreviated as PD, as used herein, refers to a worsening of one or more symptom associated with a particular disease. For example, disease progression for a subject afflicted with a cancer can include an increase in the number or size of one or more malignant lesions, tumor metastasis, and death.

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARE or CCL17).

Other examples of analytes and cytokines of the present invention include, but are not limited to chemokine (C-C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). T-cell receptors (TCR) differentiate T cells from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). A B cell makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some aspects, the cell that is modified is a lymphocyte, e.g., a T cell or a modified cell that expresses CD4, which can either be obtained from a patient or a donor. The cell can be modified to express an exogenous construct, such as, e.g., a T cell receptor (TCR) disclosed herein, which is incorporated into the cell's genome. In some aspects, the cell is modified to express CD4.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation.

Cells used in an immunotherapy described herein can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety. An immunotherapy can also comprise administering a modified cell to a subject, wherein the modified cell expresses CD4 and a TCR disclosed herein. In some aspects, the modified cell is not a T cell.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD4 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class II molecule loaded with a peptide, an anti-CD4 antibody, a superagonist anti-CD2 antibody, a superagonist anti-CD28 antibody, and a superagonist anti-CD3 antibody.

The terms "conditioning" and "pre-conditioning" are used interchangeably herein and indicate preparing a patient in need of a T cell therapy for a suitable condition. Conditioning as used herein includes, but is not limited to, reducing the number of endogenous lymphocytes, removing a cytokine sink, increasing a serum level of one or more homeostatic cytokines or pro-inflammatory factors, enhancing an effector function of T cells administered after the conditioning, enhancing antigen presenting cell activation and/or availability, or any combination thereof prior to a T cell therapy. In one aspect, "conditioning" comprises increasing a serum level of one or more cytokines, e.g., interleukin 7 (IL-7), interleukin 15 (IL-15), interleukin 10 (IL-10), interleukin 5 (IL-5), gamma-induced protein 10 (IP-10), interleukin 8 (IL-8), monocyte chemotactic protein 1 (MCP-1), placental growth factor (PLGF), C-reactive protein (CRP), soluble intercellular adhesion molecule 1 (sICAM-1), soluble vascular adhesion molecule 1 (sVCAM-1), or any combination thereof. In another aspect, "conditioning" comprises increasing a serum level of IL-7, IL-15, IP-10, MCP-1, PLGF, CRP, or any combination thereof.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one aspect, "treatment" or "treating" includes a partial remission. In another aspect, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

II. Compositions of the Disclosure

The present disclosure is directed to T Cell Receptors (TCRs) or antigen binding portions thereof that specifically bind to an epitope on CCND1, nucleic acid molecules that encode the same, and cells that comprise the TCR or the nucleic acid molecule. Some aspects of the present disclosure are directed to methods of treating a cancer in a subject in need thereof, comprising administering to the subject a cell comprising the TCRs described herein. Other aspects of the present disclosure are directed to an epitope of CCND1 that the TCRs bind to and HLA class II molecules complexed to a peptide comprising the epitope of CCND1.

The T-cell receptor, or TCR, is a molecule found on the surface of T cells, or T lymphocytes, that is responsible for recognizing fragments of antigen as peptides bound to major histocompatibility complex (MHC) molecules. The binding between TCR and antigen peptides is of relatively low affinity and is degenerate: that is, many TCRs recognize the same antigen peptide and many antigen peptides are recognized by the same TCR.

The TCR is composed of two different protein chains (that is, it is a heterodimer). In 95% of human T cells, the TCR consists of an alpha ($\alpha$) chain and a beta ($\beta$) chain (encoded by TRA and TRB, respectively), whereas in 5% of human T cells, the TCR consists of gamma and delta ($\gamma/\delta$) chains (encoded by TRG and TRD, respectively). This ratio changes during ontogeny and in diseased states (such as leukemia). It also differs between species. Orthologues of the 4 loci have been mapped in various species. Each locus can produce a variety of polypeptides with constant and variable regions.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors.

II.A. Nucleic Acid Molecules

Certain aspects of the present disclosure are directed to nucleic acid molecules comprising (i) a first nucleotide sequence encoding a recombinant TCR or an antigen binding portion thereof that specifically binds human CCND1 ("anti-CCND1 TCR"); and (ii) a second nucleotide sequence, wherein the second nucleotide sequence or the polypeptide encoded by the second nucleotide sequence inhibits the expression of an endogenous TCR. In some aspects, the second nucleotide sequence is a non-naturally occurring sequence. In other aspects, the second nucleotide sequence is synthetic. In yet other aspects, the second nucleotide sequence comprises a sequence that targets a nucleotide sequence encoding the endogenous TCR. In some aspects, the anti-CCND1 TCR cross competes for binding to human CCND1 with a reference TCR. In some aspects, the anti-CCND1 TCR binds the same epitope or an overlapping epitope of human CCND1 as a reference TCR.

In some aspects, the reference TCR comprises an alpha chain and a beta chain; wherein the alpha chain comprises a completmentarity determining region 1 (CDR1), a CDR2, and a CDR3; wherein the beta chain comprises a CDR1, a CDR2, and a CDR3; and wherein the reference TCR comprises the alpha chain CDR3 set forth in SEQ ID NO: 7 and the beta chain CDR3 set forth in SEQ ID NO: 10. In some aspects, the alpha chain CDR1, CDR2, and CDR3 sequences present in the an amino acid sequence set forth in SEQ ID NO: 1, and reference TCR comprises the beta chain CDR1, CDR2, and CDR3 sequences present in the amino acid sequence set forth in SEQ ID NO: 2. In some aspects, the reference TCR comprises an alpha chain and a beta chain, wherein the alpha chain comprises an amino acid sequence as set forth in SEQ ID NO: 1 and the beta chain comprises an amino acid sequence as set forth in SEQ ID NO: 2.

TABLE 3

Alpha Chain and Beta Chain TCR Sequences

| SEQ ID NO: | TCR Chain | Sequence |
|---|---|---|
| 1 | Alpha Chain (amino acid) | KDQVFQPSTVASSEGAVVEIFCNHSVSNAYNFFWYLHFPGCAPRLLVKGSKPSQQGRYN MTYERFSSSLLILQVREADAAVYYCAVCTLYMFNKFYFGSGTKLNVKPNIQNPDPAVYQ LRDSKSSDKSVCLFTDFDSQTNVSQSKDSDVYITDKTVLDMRSMDFKSNSAVAWSNKSD FACANAFNNSIIPEDTFFPSPESSCDVKLVEKSFETDTMLNFQNLSVIGFRILLLKVAG FNLLMTLRLWSS |
| 18 | Alpha Chain (nucleotide) | AAGGACCAAGTGTTTCAGCCTTCCACAGTGGCATCTTCAGAGGGAGCTGTGGTGGAAAT CTTCTGTAATCACTCTGTGTCCAATGCTTACAACTTCTTCTGGTACCTTCACTTCCCGG GATGTGCACCAAGACTCCTTGTTAAAGGCTCAAAGCCTTCTCAGCAGGGACGATACAAC ATGACCTATGAACGGTTCTCTTCATCGCTGCTCATCCTCCAGGTGCGGGAGGCAGATGC TGCTGTTTACTACTGTGCTGTCTGCACCTTATACAACTTCAACAAATTTTACTTTGGAT CTGGGACCAAACTCAATGTAAAACCAAATATCCAGAACCCTGACCCTGCCGTGTACCAG CTGAGAGACTCTAAATCCAGTGACAAGTCTGTCTGCCTATTCACCGATTTTGATTCTCA AACAAATGTGTCACAAAGTAAGGATTCTGATGTGTATATCACAGACAAAACTGTGCTAG ACATGAGGTCTATGGACTTCAAGAGCAACAGTGCTGTGGCCTGGAGCAACAAATCTGAC TTTGCATGTGCAAACGCCTTCAACAACAGCATTATTCCAGAAGACACCTTCTTCCCCAG CCCAGAAAGTTCCTGTGATGTCAAGCTGGTCGAGAAAAGCTTTGAAACAGATACGAACC TAAACTTTCAAAACCTGTCAGTGATTGGGTTCCGAATCCTCCTCCTGAAAGTGGCCGGG TTTAATCTGCTCATGACGCTGCGGCTGTGGTCCAGC |
| 21 | Alpha Chain Signal Peptide (amino acid) | MALQSTLGAVWLGLLLNSLWKVAES |
| 23 | Alpha Cahin Signal Peptide (nucleotide) | ATGGCTTTGCAGAGCACTCTGGGGGCGGTGTGGCTAGGGCTTCTCCTCAACTCTCTCTG GAAGGTTGCAGAAAGC |
| 2 | Beta Chain (amino acid) | GVTQTPKFQVLKTGQSMTLQCAQDMNHEYMSWYRQDPGMGLRLIHYSVGAGITDQGEVP NGYNVSRSTTEDFPLRLLSAAPSQTSVYFCASLTDNNEQFFGPGTRLTVLEDLKNVFPP EVAVFEPSEAEISHTQKATLVCLATGFYPDHVELSWWVNGKEVHSGVSTDPQPLKEQPA LNDSRYCLSSRLRVSATFWQNPRNHFRCQVQFYGLSENDEWTQDRAKPVTQIVSAEAWG RADCGFTSESYQQGVLSATILYEILLGKATLYAVLVSALVLMAMVKRKDSRG |
| 19 | Beta Chain (nucelotide) | GGTGTCACTCAGACCCCAAAATTCCAGGTCCTGAAGACAGGACAGAGCATGACACTGCA GTGTGCCCAGGATATGAACCATGAATACATGTCCTGGTATCGACAAGACCCAGGCATGG GGCTGAGGCTGATTCATTACTCAGTTGGTGCTGGTATCACTGACCAAGGAGAAGTCCCC AATGGCTACAATGTCTCCAGATCAACCACAGAGGATTTCCCGCTCAGGCTGCTGTCGGC TGCTCCCTCCCAGACATCTGTGTACTTCTGTGCCAGCCTGACAGATAACAATGAGCAGT TCTTCGGGCCAGGGACACGGCTCACCGTGCTAGAGGACCTGAAGAACGTGTTCCCCCCA GAGGTGGCCGTGTTCGAGCCTTCTGAGGCCGAGATCAGCCACACCCAGAAAGCCACCCT CGTGTGTCTGGCCACCGGCTTCTACCCCGACCATGTGGAACTGTCTTGGTGGGTCAACG GCAAAGAGGTGCACAGCGGAGTGTCCACCGACCCCCAGCCTCTGAAAGAACAGCCCGCC CTGAACGACAGCCGGTACTGCCTGAGCAGCAGACTGAGAGTGTCCGCCACCTTCTGGCA GAACCCCCGGAACCACTTCAGATGCCAGGTGCAGTTCTACGGCCTGAGCGAGAACGACG AGTGGACCCAGGACAGAGCCAAGCCCGTGACCCAGATCGTGTCTGCCGAAGCCTGGGGC AGAGCCGATTGCGGCTTTACCAGCGAGAGCTACCAGCAGGGCGTGCTGAGCGCCACCAT CCTGTACGAGATTCTGCTGGGCAAGGCCACCCTGTACGCTGTGCTGGTGTCAGCCCTGG TGCTGATGGCCATGGTCAAGCGGAAGGACAGCAGAGGC |
| 22 | Beta Chain Signal Peptide (amino acid) | MSIGLLCCAALSLLWAGPVNA |
| 24 | Beta Chain Signal Peptide (nucleotide) | ATGAGCATCGGCCTCCTGTGCTGTGCAGCCTTGTCTCTCCTGTGGGCAGGTCCAGTGAA TGCT |
| 20 | Fibroin-L Derived Signal Peptide | MMRRPIVLVLLFATSALA |

II.A.1. TCR Encoded by the First Nucleotide Sequence

The present disclosure is directed to a TCR encoded by the first nucleotide sequence described herein. In some aspects, the anti-CCND1 TCR encoded by the first nucleotide sequence comprises an alpha chain and a beta chain, wherein the alpha chain comprises a variable domain comprising an alpha chain CDR1, an alpha chain CDR2, and an alpha chain CDR3; and wherein the beta chain comprises variable domain comprising a beta chain CDR1, a beta chain CDR2, and a beta chain CDR3. In some aspects, the anti-CCND1 TCR comprises an alpha chain CDR3 comprising an amino acid sequence as set forth in SEQ ID NO: 7 (CAVCTLYNFNKFYF). In some aspects, the anti-CCND1 TCR comprises a beta chain CDR3 comprising an amino acid sequence as set forth in SEQ ID NO: 10 (CASLTDNNEQFF). In some aspects, the non-CDR regions in the alpha chain and/or the beta chain are further modified, e.g., substitution or mutation of one amino acid, two amino acids, three amino acids, four amino acids, five amino acids, or six amino acids, thereby the alpha chain and/or the beta chain are not naturally occurring. In some aspects, the substitutions or mutations can improve the TCRs described herein in various ways, e.g., binding affinity, binding specificity, stability, viscosity, or any combination thereof In some aspects, the anti-CCND1 TCR encoded by the first nucleotide sequence comprises an alpha chain CDR1, wherein the alpha chain CDR1 of the anti-CCND1 TCR comprises an amino acid sequence as set forth in SEQ ID NO: 5 (VSNAYN) In some aspects, the anti-CCND1 TCR encoded by the first nucleotide sequence comprises a beta chain CDR1, wherein the beta chain CDR1 of the anti-CCND1 TCR comprises an amino acid sequence as set forth in SEQ ID NO: 8 (MNHEY).

In some aspects, the anti-CCND1 TCR encoded by the first nucleotide sequence comprises an alpha chain CDR2, wherein the alpha chain CDR2 of the anti-CCND1 TCR comprises an amino acid sequence as set forth in SEQ ID NO: 6 (GSKP). In some aspects, the anti-CCND1 TCR encoded by the first nucleotide sequence comprises a beta chain CDR2, wherein the beta chain CDR2 of the anti-CCND1 TCR comprises an amino acid sequence as set forth in SEQ ID NO: 9 (SVGAGI).

In some aspects, the anti-CCND1 TCR encoded by the first nucleotide sequence comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some aspects, the anti-CCND1 TCR encoded by the first nucleotide sequence comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-CCND1 TCR comprises an alpha chain CDR3 comprising an amino acid sequence as set forth in SEQ ID NO: 7. In some aspects, the anti-CCND1 TCR encoded by the first nucleotide sequence comprises an alpha chain variable domain present in the alpha chain amino acid sequence set forth in SEQ ID NO: 1.

In some aspects, the anti-CCND1 TCR encoded by the first nucleotide sequence comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some aspects, the anti-CCND1 TCR encoded by the first nucleotide sequence comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-CCND1 TCR comprises a beta chain CDR3 comprising an amino acid sequence as set forth in SEQ ID NO: 10. In some aspects, the anti-CCND1 TCR encoded by the first nucleotide sequence comprises a beta chain variable domain present in the amino acid sequence set forth in SEQ ID NO: 2.

In some aspects, the anti-CCND1 TCR encoded by the first nucleotide further comprises an alpha chain constant region, a beta chain constant region, or both an alpha chain constant region and a beta chain constant region. In some aspects, the anti-CCND1 TCR encoded by the first nucleotide sequence comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some aspects, the anti-CCND1 TCR encoded by the first nucleotide sequence comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-CCND1 TCR comprises an alpha chain CDR3 comprising an amino acid sequence as set forth in SEQ ID NO: 7. In some aspects, the anti-CCND1 TCR encoded by the first nucleotide sequence comprises an alpha chain constant region present in the alpha chain amino acid sequence set forth in SEQ ID NO: 1. In some aspects, the anti-CCND1 TCR encoded by the first nucleotide further comprises an alpha constant region that is different from endogenous, e.g., naturally occurring, constant regions of the alpha chain. In some aspects, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some aspects, the anti-CCND1 TCR encoded by the first nucleotide sequence comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some aspects, the anti-CCND1 TCR encoded by the first nucleotide sequence comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-CCND1 TCR comprises a beta chain CDR3 comprising an amino acid sequence as set forth in SEQ ID NO: 10. In some aspects, the anti-CCND1 TCR encoded by the first nucleotide sequence comprises a beta chain constant region present in the amino acid sequence set forth in SEQ ID NO: 2. In some aspects, the anti-CCND1 TCR encoded by the first nucleotide further comprises a beta constant region that is different from endogenous, e.g., naturally occurring, constant regions of the beta chain. In some aspects, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain aspects, the anti-CCND1 TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some aspects, the anti-CCND1 TCR encoded by the first nucleotide sequence comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-CCND1 TCR comprises an alpha chain CDR3 comprising an amino acid sequence as set forth in SEQ ID NO: 7. In some aspects, the anti-CCND1 TCR encoded by the first nucleotide sequence comprises an alpha chain comprising the amino acid sequence set forth in SEQ ID NO: 1.

In certain aspects, the anti-CCND1 TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some aspects, the anti-CCND1 TCR encoded by the first nucleotide sequence comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-CCND1 TCR comprises a beta chain CDR3 comprising an amino acid sequence as set forth in SEQ ID NO: 10. In some aspects, the anti-CCND1 TCR encoded by the first nucleotide sequence comprises a beta chain comprising the amino acid sequence set forth in SEQ ID NO: 2.

In some aspects, the anti-CCND1 TCR encoded by the first nucleotide sequence comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

In some aspects, the alpha chain of the anti-CCND1 TCR encoded by the first nucleotide sequence further comprises a signal peptide. Any signal peptide can be used in the anti-CCDN1 TCR alpha chains disclosed herein. In some aspects the signal peptide is a naturally occurring TCR alpha chain signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 21. In some aspects, the signal peptide is a heterologous signal peptide, e.g., a signal peptide derived from a protein other than a TCR alpha chain. In some aspects, the signal peptide is a synthetic signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 20 or 22. In some aspects, the alpha chain of CCND1 TCR encoded by the first nucleotide sequence does not comprise a signal peptide.

In some aspects, the signal peptide of the alpha chain is encoded by a nucleic acid sequence having at least about 50%, at least about 55%, at least about 60%, at least about 65%, at least about 70%, at least about 75%, at least about 80%, at least about 85%, at least about 90%, at least about 95%, at least about 96%, at least about 97% at least about 98%, at least about 99%, or about 100% sequence identity with the nucleic acid sequence set forth in SEQ ID NO: 23 or 24.

In some aspects, the beta chain of the anti-CCND1 TCR encoded by the first nucleotide sequence further comprises a signal peptide. Any signal peptide can be used in the anti-CCDN1 TCR beta chains disclosed herein. In some aspects the signal peptide is a naturally occurring TCR beta chain signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 22. In some aspects, the signal peptide is a heterologous signal peptide, e.g., a signal peptide derived from a protein other than a TCR beta chain. In some aspects, the signal peptide is a synthetic signal peptide. In some aspects, the signal peptide comprises an amino acid sequence having at least about 80%, at least about 85%, at least about 90%, at least about 95%, at least about 96%, at least about 97% at least about 98%, at least about 99%, or about 100% sequence identity with the amino acid sequence set forth in SEQ ID NO: 20 or 21. In some aspects, the beta chain of CCND1 TCR encoded by the first nucleotide sequence does not comprise a signal peptide.

In some aspects, the signal peptide of the beta chain is encoded by a nucleic acid sequence having at least about 50%, at least about 55%, at least about 60%, at least about 65%, at least about 70%, at least about 75%, at least about 80%, at least about 85%, at least about 90%, at least about 95%, at least about 96%, at least about 97% at least about 98%, at least about 99%, or about 100% sequence identity with the nucleic acid sequence set forth in SEQ ID NO: 23 or 24.

In some aspects, each of the alpha chain and the beta chain of the anti-CCND1 TCR encoded by the first nucleotide sequence further comprises a signal peptide. In some aspects, the signal peptide of the alpha chain is the same as the signal peptide of the beta chain. In some aspects, the signal peptide of the alpha chain is different from the signal peptide of the beta chain.

II.A.2. Epitopes

In some aspects, the anti-CCND1 TCR encoded by the first nucleotide sequence binds the same epitope as a reference TCR. In some aspects, the anti-CCND1 TCR binds to an epitope of CCND1 comprising the amino acid sequence set forth in SEQ ID NO: 13 (SPNNFLSYYRLTRFLSR-VIK). In some aspects, the anti-CCND1 TCR binds to an epitope of CCND1 consisting of an amino acid sequence as set forth in SEQ ID NO: 13. In some aspects, the epitope consists of amino acid residues 219-238 of CCND1 (SEQ ID NO: 16), e.g., "CCND1$_{219-238}$."

In certain aspects, the epitope is part of a larger polypeptide, e.g., a peptide that comprises the epitope sequence and (i) one or more additional amino acids N-terminal to the epitope sequence and/or (ii) one or more additional amino acids C-terminal to the epitope sequence. In some aspects, the polypeptide comprising the epitope is at least about 10 amino acids, at least about 11 amino acids, at least about 12 amino acids, at least about 13 amino acids, at least about 14 amino acids, at least about 15 amino acids, at least about 16 amino acids, at least about 17 amino acids, at least about 18 amino acids, at least about 19 amino acids, at least about 20 amino acids, at least about 25 amino acids, at least about 30 amino acids, at least about 35 amino acids, at least about 40 amino acids, at least about 45 amino acids, or at least about 50 amino acids in length. In certain aspects, the polypeptide comprising the epitope is at least about 5 to at least about 10, at least about 5 to at least about 15, at least about 5 to at least about 20, at least about 10 to at least about 15, at least about 10 to at least about 20, at least about 10 to at least about 25, at least about 10 to at least about 30, at least about 10 to at least about 35, at least about 10 to at least about 40, at least about 10 to at least about 45, at least about 10 to at least about 50, at least about 15 to at least about 20, at least about 15 to at least about 25, at least about 15 to at least about 30, at least about 15 to at least about 35, at least about 15 to at least about 40, at least about 15 to at least about 45, or at least about 15 to at least about 50 amino acids in length.

In certain aspects, the polypeptide comprising the epitope comprises the epitope and at least about 1, at least about 2, at least about 3, at least about 4, at least about 5, at least about 6, at least about 7, at least about 8, at least about 9, at least about 10, at least about 11, at least about 12, at least about 13, at least about 14, at least about 15 additional amino acids N-terminal to the epitope. In certain aspects, the polypeptide comprising the epitope comprises the epitope and at least about 1, at least about 2, at least about 3, at least about 4, at least about 5, at least about 6, at least about 7, at least about 8, at least about 9, at least about 10, at least about 11, at least about 12, at least about 13, at least about 14, at least about 15 additional amino acids C-terminal to the epitope.

In certain aspects, the epitope is complexed with an HLA class II molecule. The human leukocyte antigen (HLA) system (the major histocompatibility complex [MHC] in humans) is an important part of the immune system and is controlled by genes located on chromosome 6. It encodes cell surface molecules specialized to present antigenic peptides to the T-cell receptor (TCR) on T cells. (See also Overview of the Immune System.) MHC molecules that present antigen (Ag) are divided into 2 main classes: Class I MHC molecules and Class II MHC molecules.

Class II MHC molecules are present as transmembrane glycoproteins on the surface of professional antigen presenting cells (APCs). Intact class II molecules consist of an alpha chain and a beta chain. The gene encoding the alpha chain of MHC II class molecules is composed of 5 exons, and the gene encoding the beta chain is composed of 6 exons. Exon 1 encodes the leader peptide, exons 2 and 3 encode the two extracellular domains, and exons 4 and 5 contribute to the transmembrane domain and cytoplasmic tail for each of the alpha and beta subunits. Three loci in the HLA complex encode MHC class II proteins: HLA-DR, HLA-DQ, and HLA-DP. T cells that express CD4 molecules react with class II MHC molecules. These lymphocytes often have a cytotoxic function and activate a response to eliminate self-cells infected with intracellular pathogens or to destroy extracellular parasites. Because only professional antigen presenting cells (APCs) express class II MHC molecules, only these cells present antigen for CD4 T cells (CD4 binds to the nonpolymorphic part of the alpha-2 and beta-2 domains of the alpha and beta chains of an MHC class II molecule respectively).

In some aspects, the HLA class II alpha and beta chains are selected from an HLA-DR, HLA-DP, and HLA-DQ allele. In certain aspects, the HLA class II alpha chain is an HLA-DR alpha chain. In some aspects the HLA class II beta chain is an HLA-DR beta chain. In certain aspects, the HLA class II alpha chain is an HLA-DP alpha chain. In some aspects the HLA class II beta chain is an HLA-DP beta chain. In certain aspects, the HLA class II alpha chain is an HLA-DQ alpha chain. In some aspects the HLA class II beta chain is an HLA-DQ beta chain.

Many HLA-DR, HLA-DP, and HLA-DQ alleles are known in the art, and any of the known alleles can be used in the present disclosure. An updated list of HLA alleles is available at hla.alleles.org/ (last visited on Jun. 18, 2019), which is incorporated by reference herein in its entirety.

II.A.3 The Second Nucleotide Sequence

The second nucleotide sequence of the nucleic acid molecule disclosed herein can be any sequence or can encode for any polypeptide that is capable of inhibiting the expression of an endogenous TCR. In some aspects, the second nucleotide sequence is one or more siRNAs. In some aspects, the one or more siRNAs are complementary to a target sequence within a nucleotide sequence encoding a constant region of an endogenous TCR. In certain aspects, the one or more siRNAs are complementary to a target sequence within a nucleotide sequence encoding a constant region of wild-type, human TCR. In some aspects, the one or more siRNAs are complementary to a target sequence within a nucleotide sequence encoding a constant region of the alpha chain of wild-type TCR. In some aspects, the one or more siRNAs are complementary to a target sequence within a nucleotide sequence encoding a constant region of the beta chain of wild-type TCR. In some aspects, the one or more siRNAs comprise (i) one or more siRNA's that are complementary to a target sequence within a nucleotide sequence encoding a constant region of the alpha chain of wild-type TCR and (ii) one or more siRNA's that are complementary to a target sequence within a nucleotide sequence encoding a constant region of the beta chain of wild-type TCR.

In some aspects, the one or more siRNAs comprise a nucleotide sequence selected from the group consisting of SEQ ID NOs: 25-28 (Table 4). In some aspects, the second nucleotide sequence of the nucleic acid molecule encodes one or more siRNAs, wherein the one or more siRNAs are complementary to a target sequence within a nucleotide sequence encoding a constant region of the alpha chain of wild-type TCR, and wherein the one or more siRNAs comprise the nucleic acid sequences set forth in SEQ ID NOs: 25 and 26.

TABLE 4 siRNA Sequences

| SEQ ID NO: | siRNA | Sequence (Nucleotides 1-19 are ribonucleotides; nucleotides 20-21 are deoxyribonucleotides) |
|---|---|---|
| 25 | siRNA-TCRa-1 | GUAAGGAUUCUGAUGUGUATT |
| 26 | siRNA-TCRa-2 | UACACAUCAGAAUCCUUACTT |

TABLE 4-continued

| | siRNA Sequences | |
| --- | --- | --- |
| SEQ ID NO: | siRNA | Sequence (Nucleotides 1-19 are ribonucleotides; nucleotides 20-21 are deoxyribonucleotides) |
| 27 | siRNA-TCRb-1 | CCACCAUCCUCUAUGAGAUTT |
| 28 | siRNA-TCRb-2 | AUCUCAUAGAGGAUGGUGGTT |

In some aspects, the second nucleotide sequence of the nucleic acid molecule encodes one or more siRNAs, wherein the one or more siRNAs are complementary to a target sequence within a nucleotide sequence encoding a constant region of the beta chain of wild-type TCR, and wherein the one or more siRNAs comprise the nucleic acid sequences set forth in SEQ ID NOs: 27 and 28. In some aspects, the second nucleotide sequence of the nucleic acid molecule encodes one or more siRNAs, wherein the one or more siRNAs comprise (i) one or more siRNAs that are complementary to a target sequence within a nucleotide sequence encoding a constant region of the alpha chain of wild-type TCR, wherein the one or more siRNAs comprise the nucleic acid sequences set forth in SEQ ID NOs: 25 and 26; and (ii) one or more siRNAs that are complementary to a target sequence within a nucleotide sequence encoding a constant region of the beta chain of wild-type TCR, wherein the one or more siRNAs comprise the nucleic acid sequences set forth in SEQ ID NOs: 27 and 28.

In some aspects, the second nucleotide sequence of the nucleic acid molecule comprises SEQ ID NOs: 25-28. In some aspects, the second nucleotide sequence comprises SEQ ID NOs: 25-28, wherein one or more of SEQ ID NOs: 25-28 is separated by one or more nucleic acids that do not encode an siRNA. In certain aspects, the one or more siRNAs are selected from the siRNAs disclosed in U.S. Publication No. 2010/0273213 A1, which is incorporated by reference herein in its entirety.

In some aspects, the second nucleotide sequence of the nucleic acid molecule encodes a protein, wherein the protein is capable of inhibiting the expression of an endogenous, e.g., wild-type, TCR. In some aspects, the second nucleotide sequence encodes Cas9.

II.A.3 Vectors

Certain aspects of the present disclosure are directed to vectors comprising a nucleic acid molecule disclosed herein. In some aspects, the vector is a viral vector. In some aspects, the vector is a viral particle or a virus. In some aspects, the vector is a mammalian vector. In some aspects, the vector is a bacterial vector.

In certain aspects, the vector is a retroviral vector. In some aspects, the vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular aspects, the vector is an AAV vector. In some aspects, the vector is a lentivirus. In particular aspects, the vector is an AAV vector. In some aspects, the vector is a Sendai virus. In some aspects, the vector is a hybrid vector. Examples of hybrid vectors that can be used in the present disclosure can be found in Huang and Kamihira, *Biotechnol. Adv.* 31(2): 208-23 (2103), which is incorporated by reference herein in its entirety.

II.B. Recombinant T Cell Receptors (TCRs)

Certain aspects of the present disclosure are directed to recombinant T cell receptors (TCRs) or an antigen binding portion thereof that specifically bind human CCND1 ("an anti-CCND1 TCR"). In some aspects, the anti-CCND1 TCR is encoded by the a nucleic acid molecule disclosed herein.

In some aspects, the anti-CCND1 TCR cross competes for binding to human CCND1 with a reference TCR. In some aspects, the anti-CCND1 TCR binds the same epitope or an overlapping epitope of human CCND1 as a reference TCR. In some aspects, the reference TCR comprises an alpha chain and a beta chain, and the alpha chain comprises of the reference TCR comprises an amino acid sequence as set forth in SEQ ID NO: 1. In some aspects, the beta chain of the reference TCR comprises an amino acid sequence as set forth in SEQ ID NO: 2.

In some aspects, the anti-CCND1 TCR comprises an alpha chain and a beta chain, wherein the alpha chain comprises a constant region, and wherein the beta chain comprises a constant region; wherein the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1. In some aspects, the anti-CCND1 TCR comprises an alpha chain and a beta chain, wherein the alpha chain comprises a constant region, and wherein the beta chain comprises a constant region; wherein the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some aspects, the anti-CCND1 TCR comprises an alpha chain and a beta chain, wherein the alpha chain comprises a constant region, and wherein the beta chain comprises a constant region; wherein (i) the alpha chain constant region comprises an amino acid sequence having a least 1, at least 2, at least 3, at least 4, or at least 5 amino acid substitutions relative to the constant region of an alpha chain comprising the amino acid sequence set forth in SEQ ID NO: 1; and (ii) the beta chain constant region comprises an amino acid sequence having a least 1, at least 2, at least 3, at least 4, or at least 5 amino acid substitutions relative to the constant region of a beta chain comprising the amino acid sequence set forth in SEQ ID NO: 2.

In some aspects, the alpha chain of the anti-CCND1 TCR comprises a variable domain comprising an alpha chain CDR1, an alpha chain CDR2, and an alpha chain CDR3; and the beta chain of the anti-CCND1 TCR comprises a variable domain comprising a beta chain CDR1, a beta chain CDR2, and a beta chain CDR3. In some aspects, the anti-CCND1 TCR comprises an alpha chain CDR3 comprising an amino acid sequence as set forth in SEQ ID NO: 7. In some aspects, the anti-CCND1 TCR comprises a beta chain CDR3 comprising an amino acid sequence as set forth in SEQ ID NO: 10.

In some aspects, the alpha chain CDR1 of the anti-CCND1 TCR comprises an amino acid sequence as set forth in SEQ ID NO: 5. In some aspects, the beta chain CDR1 of the anti-CCND1 TCR comprises an amino acid sequence as set forth in SEQ ID NO: 8.

In some aspects, the alpha chain CDR2 of the anti-CCND1 TCR comprises an amino acid sequence as set forth in SEQ ID NO: 6. In some aspects, the beta chain CDR2 of the anti-CCND1 TCR comprises an amino acid sequence as set forth in SEQ ID NO: 9.

In some aspects, the anti-CCND1 TCR comprises an alpha chain variable domain having at least about 80%, at least about 85%, at least about 90%, at least about 95%, at least about 96%, at least about 97% at least about 98%, at least about 99%, or about 100% sequence identity with a variable domain of the alpha chain amino acid sequence set forth in SEQ ID NO: 1. In some aspects, the anti-CCND1 TCR comprises an alpha chain variable domain having at least about 80%, at least about 85%, at least about 90%, at least about 95%, at least about 96%, at least about 97% at least about 98%, or at least about 99% sequence identity with a variable domain of the alpha chain amino acid sequence set forth in SEQ ID NO: 1, wherein the anti-CCND1 TCR comprises an alpha chain CDR3 comprising an amino acid sequence as set forth in SEQ ID NO: 7. In some aspects, the anti-CCND1 TCR comprises an alpha chain variable domain present in the alpha chain amino acid sequence set forth in SEQ ID NO: 1.

In some aspects, the anti-CCND1 TCR comprises a beta chain variable domain having at least about 80%, at least about 85%, at least about 90%, at least about 95%, at least about 96%, at least about 97% at least about 98%, at least about 99%, or about 100% sequence identity with a variable domain of the beta chain amino acid sequence set forth in SEQ ID NO: 2. In some aspects, the anti-CCND1 TCR comprises a beta chain variable domain having at least about 80%, at least about 85%, at least about 90%, at least about 95%, at least about 96%, at least about 97% at least about 98%, or at least about 99% sequence identity with a variable domain of the beta chain amino acid sequence set forth in SEQ ID NO: 2, wherein the anti-CCND1 TCR comprises a beta chain CDR3 comprising an amino acid sequence as set forth in SEQ ID NO: 10. In some aspects, the anti-CCND1 TCR comprises a beta chain variable domain present in the beta chain amino acid sequence set forth in SEQ ID NO: 2.

In some aspects, the anti-CCND1 TCR encoded by the first nucleotide further comprises an alpha chain constant region, a beta chain constant region, or both an alpha chain constant region and a beta chain constant region. In some aspects, the anti-CCND1 TCR comprises an alpha chain constant region having at least about 80%, at least about 85%, at least about 90%, at least about 95%, at least about 96%, at least about 97% at least about 98%, at least about 99%, or about 100% sequence identity with a constant region of the alpha chain amino acid sequence set forth in SEQ ID NO: 1. In some aspects, the anti-CCND1 TCR comprises an alpha chain constant region having at least about 80%, at least about 85%, at least about 90%, at least about 95%, at least about 96%, at least about 97% at least about 98%, or at least about 99% sequence identity with a constant region of the alpha chain amino acid sequence set forth in SEQ ID NO: 1, wherein the anti-CCND1 TCR comprises an alpha chain CDR3 comprising an amino acid sequence as set forth in SEQ ID NO: 7. In some aspects, the anti-CCND1 TCR comprises an alpha chain constant region present in the alpha chain amino acid sequence set forth in SEQ ID NO: 1. In some aspects, the anti-CCND1 TCR encoded by the first nucleotide further comprises an alpha constant region that is different from endogenous, e.g., naturally occurring, constant regions of the alpha chain. In some aspects, the alpha chain constant region comprises an amino acid sequence comprising at least 1, at least 2, at least 3, at least 4, or at least 5 amino acid substitutions relative to the amino acid sequence of the constant region of the alpha chain amino acid sequence set forth in SEQ ID NO: 1.

In some aspects, the anti-CCND1 TCR comprises a beta chain constant region having at least about 80%, at least about 85%, at least about 90%, at least about 95%, at least about 96%, at least about 97% at least about 98%, at least about 99%, or about 100% sequence identity with a constant region of the beta chain amino acid sequence set forth in SEQ ID NO: 2. In some aspects, the anti-CCND1 TCR comprises a beta chain constant region having at least about 80%, at least about 85%, at least about 90%, at least about 95%, at least about 96%, at least about 97% at least about 98%, or at least about 99% sequence identity with a constant region of the beta chain amino acid sequence set forth in SEQ ID NO: 2, wherein the anti-CCND1 TCR comprises a beta chain CDR3 comprising an amino acid sequence as set forth in SEQ ID NO: 10. In some aspects, the anti-CCND1 TCR comprises a beta chain constant region present in the beta chain amino acid sequence set forth in SEQ ID NO: 2. In some aspects, the anti-CCND1 TCR encoded by the first nucleotide further comprises a beta constant region that is different from endogenous, e.g., naturally occurring, constant regions of the beta chain. In some aspects, the beta chain constant region comprises an amino acid sequence comprising at least 1, at least 2, at least 3, at least 4, or at least 5 amino acid substitutions relative to the amino acid sequence of the constant region of the beta chain amino acid sequence set forth in SEQ ID NO: 2.

In certain aspects, the anti-CCND1 TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1. In some aspects, the anti-CCND1 TCR comprises an alpha chain having at least about 80%, at least about 85%, at least about 90%, at least about 95%, at least about 96%, at least about 97% at least about 98%, at least about 99%, or about 100% sequence identity with the alpha chain amino acid sequence set forth in SEQ ID NO: 1, wherein the anti-CCND1 TCR comprises an alpha chain CDR3 comprising an amino acid sequence as set forth in SEQ ID NO: 7. In some aspects, the anti-CCND1 TCR comprises an alpha chain comprising the amino acid sequence set forth in SEQ ID NO: 1.

In certain aspects, the anti-CCND1 TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2. In some aspects, the anti-CCND1 TCR comprises a beta chain having at least about 80%, at least about 85%, at least about 90%, at least about 95%, at least about 96%, at least about 97% at least about 98%, at least about 99%, or about 100% sequence identity with the beta chain amino acid sequence set forth in SEQ ID NO: 2, wherein the anti-CCND1 TCR comprises a beta chain CDR3 comprising an amino acid sequence as set forth in SEQ ID NO: 10. In some aspects, the anti-CCND1 TCR comprises a beta chain comprising the amino acid sequence set forth in SEQ ID NO: 2.

In some aspects, the anti-CCND1 TCR comprises an alpha chain constant region, a beta chain constant region, or both; and wherein the alpha chain constant region, the beta chain constant region, or both comprises an amino acid sequence having at least 1, at least 2, at least 3, at least 4, or at least 5 substitutions within the target sequence relative to the corresponding amino acid sequence of an endogenous TCR.

II.B.2. Epitopes

In some aspects, the anti-CCND1 TCR binds the same epitope as a reference TCR. In some aspects, the anti- CCND1 TCR binds to an epitope of CCND1 comprising the amino acid sequence set forth in SEQ ID NO: 13. In some aspects, the anti-CCND1 TCR binds to an epitope of CCND1 consisting of an amino acid sequence as set forth in SEQ ID NO: 13. In some aspects, the epitope consists of amino acid residues 219-238 of CCND1 (SEQ ID NO: 16), e.g., "CCND1$_{219-238}$."

In certain aspects, the epitope is complexed with an HLA class II molecule. In some aspects, the HLA class II molecule comprises an alpha chain and a beta chain. In some aspects, the alpha chain is selected from an HLA-DR alpha chain, an HLA-DP alpha chain, and an HLA-DQ alpha chain. In some aspects, the beta chain is selected from an HLA-DR beta chain, an HLA-DP beta chain, and an HLA-DQ beta chain. In certain aspects, the HLA class II molecule comprises an HLA-DR alpha chain and an HLA-DR beta chain. In certain aspects, the HLA class II molecule comprises an HLA-DP alpha chain and an HLA-DP beta chain. In certain aspects, the HLA class II molecule comprises an HLA-DQ alpha chain and an HLA-DQ beta chain.

Many HLA-DR, HLA-DP, and HLA-DQ alleles are known in the art, and any of the known alleles can be used in the present disclosure. An updated list of HLA alleles is available at hla.alleles.org/ (last visited on Feb. 27, 2019), which is incorporated by reference herein in its entirety.

II.B.3. Bispecific T Cell Receptors (TCRs)

Certain aspects of the present disclosure are directed to a bispecific TCR comprising a first antigen-binding domain and a second antigen-binding domain, wherein the first antigen-binding domain comprises a TCR or an antigen-binding portion thereof disclosed herein. In some aspects, the first antigen-binding domain comprises a single chain variable fragment ("scFv").

In some aspects, the second antigen-binding domain binds specifically to a protein expressed on the surface of a T cell. Any protein expressed on the surface of a T cell can be targeted by the bispecific antibody disclosed herein. In certain aspects, the protein expressed on the surface of a T cell is not expressed by other cells. In some aspects, the protein expressed on the surface of a T cell is expressed on the surface of one or more other human immune cells. In some aspects, the protein expressed on the surface of a T cell is expressed on the surface of one or more other human immune cells, but it is not expressed on the surface of a human non-immune cell. In some aspects, the second antigen-binding domain binds specifically to a protein expressed on the surface of a T cell selected from CD3, CD4, CD2, CD5, CD6, CD8, CD11a (LFA-1α), CD43, CD45, and CD53. In certain aspects, the second antigen-binding domain binds specifically to CD3. In certain aspects, the second antigen-binding domain binds specifically to CD4. In some aspects, the second antigen-binding domain comprises an scFv.

In some aspects, the first antigen-binding domain and the second antigen-binding domain are linked or associated by a covalent bond. In some aspects, the first antigen-binding domain and the second antigen-binding domain are linked by a peptide bond.

II.C. Cells Expressing TCRs

Certain aspects of the present disclosure are directed to cells comprising a nucleic acid molecule disclosed herein, a vector disclosed herein, a recombinant TCR disclosed herein, a bispecific TCR disclosed herein, or any combination thereof. Any cell can be used in the present disclosure.

In certain aspects, the cell expresses CD4. CD4 expression can be naturally occurring, e.g., the CD4 is expressed from a nucleic acid sequence that is endogenously expressed by the cell. For example, T cells, monocytes, macrophages, dendritic cells, and natural killer (NK) cells naturally express CD4. Thus, in some aspects, the cell is a T cell, a monocyte, a macrophage, a dendritic cell, or a natural killer cell. In certain aspects, the cell is a T cell selected from a natural killer T (NKT) cell and an innate lymphoid cell (ILC). In some aspects, the cell is a monocyte. In some aspects, the cell is a macrophage. In some aspects, the cell is a dendritic cell.

In some aspects, the T cell is isolated from a human subject. In some aspects, the human subject is the same subject that will ultimately receive the T cell therapy. In other aspects, the subject is a donor subject, wherein the donor subject is not the same subject that will receive the T cell therapy.

In some aspects, the cell is a cell that does not naturally express CD4, wherein the cell has been modified to express CD4. In some aspects, the cell comprises a transgene encoding CD4, wherein the transgene is expressed by the cell. In some aspects, the cell comprises a transgene encoding a protein that activates expression of endogenous CD4 by the cell. In some aspects, the cell comprises a transgene encoding a protein or siRNA that inhibits an inhibitor of CD4 expression in the cell. In some aspects, the transgene is incorporated into the genome of the cell. In some aspects, the transgene is not incorporated into the genome of the cell.

In some aspects, the cell that is modified to express CD4 is isolated from a human subject. In some aspects, the human subject is the same subject that will ultimately receive the cell therapy. In other aspects, the subject is a donor subject, wherein the donor subject is not the same subject that will receive the cell therapy.

II.D. HLA Class II Molecules

Certain aspects of the present disclosure are directed to a HLA class II molecule complexed to a peptide, wherein the peptide comprises the amino acid sequence set forth in SEQ ID NO: 13. In some aspects, the peptide consists of the amino acid sequence set forth in SEQ ID NO: 13.

In some aspects, the HLA Class II molecule is an HLA-DR, HLA-DP, or an HLA-DQ allele. In some aspects, the HLA class II molecule is any HLA allele disclosed at hla.alleles.org/ (last visited on Feb. 27, 2019)

In some aspects, the HLA Class II molecule comprises an alpha chain and a beta chain. In some aspects, the sequence of the alpha chain is selected from any of the HLA alpha chain protein sequences available at hla.alleles.org (last visited Feb. 27, 2019).

II.D.1. HLA-DP Class II Molecules

In some aspects, the alpha chain is an HLA-DP alpha chain. Any HLA-DP alpha chain allele known in the art can be used in the compositions and methods disclosed herein. In some aspects, the alpha chain is selected from an HLA-DPA1*01, HLA-DPA1*02, HLA-DPA1*03, and HLA-DPA1*04 allele. In certain aspects, the DP alpha chain comprises an HLA-DPA1*01 allele. In certain aspects, the DP alpha chain comprises an HLA-DPA1*02 allele. In certain aspects, the DP alpha chain comprises an HLA-DPA1*03 allele. In certain aspects, the DP alpha chain comprises an HLA-DPA1*04 allele.

In certain aspects, the DP alpha chain is selected from DPA1*01:03:01:01, DPA1*01:03:01:02, DPA1*01:03:01:03, DPA1*01:03:01:04, DPA1*01:03:01:05, DPA1*01:03:01:06, DPA1*01:03:01:07, DPA1*01:03:01:08, DPA1*01:03:01:09, DPA1*01:03:01:10, DPA1*01:03:01:11, DPA1*01:03:01:12, DPA1*01:03:01:13, DPA1*01:03:01:14, DPA1*01:03:01:15, DPA1*01:03:01:16, DPA1*01:03:01:17, DPA1*01:03:01:18Q, DPA1*01:03:01:19, DPA1*01:03:01:20, DPA1*01:03:01:21, DPA1*01:03:01:22, DPA1*01:03:01:23, DPA1*01:03:02, DPA1*01:03:03, DPA1*01:03:04, DPA1*01:03:05, DPA1*01:03:06, DPA1*01:03:07, DPA1*01:03:08, DPA1*01:03:09, DPA1*01:04, DPA1*01:05, DPA1*01:06:01, DPA1*01:06:02, DPA1*01:07, DPA1*01:08, DPA1*01:09, DPA1*01:10, DPA1*01:11, DPA1*01:12, DPA1*01:13, DPA1*01:14, DPA1*01:15, DPA1*01:16, DPA1*01:17, DPA1*01:18, DPA1*01:19, DPA1*02:01:01:01, DPA1*02:01:01:02, DPA1*02:01:01:03, DPA1*02:01:01:04, DPA1*02:01:01:05, DPA1*02:01:01:06, DPA1*02:01:01:07, DPA1*02:01:01:08, DPA1*02:01:01:09, DPA1*02:01:01:10, DPA1*02:01:01:11, DPA1*02:01:02:01, DPA1*02:01:02:02, DPA1*02:01:03, DPA1*02:01:04, DPA1*02:01:05, DPA1*02:01:06, DPA1*02:01:07, DPA1*02:01:08:01, DPA1*02:01:08:02, DPA1*02:02:02:01, DPA1*02:02:02:02, DPA1*02:02:02:03, DPA1*02:02:02:04, DPA1*02:02:02:05, DPA1*02:02:03, DPA1*02:02:04, DPA1*02:02:05, DPA1*02:02:06, DPA1*02:03, DPA1*02:04, DPA1*02:05, DPA1*02:06, DPA1*02:07:01:01, DPA1*02:07:01:02, DPA1*02:07:01:03, DPA1*02:08, DPA1*02:09, DPA1*02:10, DPA1*02:11, DPA1*02:12, DPA1*02:13N, DPA1*02:14, DPA1*02:15, DPA1*02:16, DPA1*03:01:01:01, DPA1*03:01:01:02, DPA1*03:01:01:03, DPA1*03:01:01:04, DPA1*03:01:01:05, DPA1*03:01:02, DPA1*03:02, DPA1*03:03, DPA1*03:04, DPA1*04:01:01:01, DPA1*04:01:01:02, DPA1*04:01:01:03, DPA1*04:02, or any combination thereof.

In some aspects, the beta chain is an HLA-DP beta chain. Any HLA-DP beta chain allele known in the art can be used in the compositions and methods disclosed herein. In certain aspects, the DP beta chain comprises an allele selected from an DPB1*01, DPB1*02, DPB1*03, DPB1*04, DPB1*05, DPB1*06, DPB1*08, DPB1*09, DPB1*10, DPB1*100, DPB1*101, DPB1*102, DPB1*103, DPB1*104, DPB1*105, DPB1*106, DPB1*107, DPB1*108, DPB1*109, DPB1*11, DPB1*110, DPB1*111, DPB1*112, DPB1*113, DPB1*114, DPB1*115, DPB1*116, DPB1*117, DPB1*118, DPB1*119, DPB1*120, DPB1*121, DPB1*122, DPB1*123, DPB1*124, DPB1*125, DPB1*126, DPB1*127, DPB1*128, DPB1*129, DPB1*13, DPB1*130, DPB1*131, DPB1*132, DPB1*133, DPB1*134, DPB1*135, DPB1*136, DPB1*137, DPB1*138, DPB1*139, DPB1*14, DPB1*140, DPB1*141, DPB1*142, DPB1*143, DPB1*144, DPB1*145, DPB1*146, DPB1*147, DPB1*148, DPB1*149, DPB1*15, DPB1*150, DPB1*151, DPB1*152, DPB1*153, DPB1*154, DPB1*155, DPB1*156, DPB1*157, DPB1*158, DPB1*159, DPB1*16, DPB1*160, DPB1*161, DPB1*162, DPB1*163, DPB1*164, DPB1*165, DPB1*166, DPB1*167, DPB1*168, DPB1*169, DPB1*17, DPB1*170, DPB1*171, DPB1*172, DPB1*173, DPB1*174, DPB1*175, DPB1*176, DPB1*177, DPB1*178, DPB1*179, DPB1*18, DPB1*180, DPB1*181, DPB1*182, DPB1*183, DPB1*184, DPB1*185, DPB1*186, DPB1*187, DPB1*188, DPB1*189, DPB1*19, DPB1*190, DPB1*191, DPB1*192, DPB1*193, DPB1*194, DPB1*195, DPB1*196, DPB1*197, DPB1*198, DPB1*199, DPB1*20, DPB1*200, DPB1*201, DPB1*202, DPB1*203, DPB1*204, DPB1*205, DPB1*206, DPB1*207, DPB1*208, DPB1*209, DPB1*21, DPB1*210, DPB1*211, DPB1*212, DPB1*213, DPB1*214, DPB1*215, DPB1*216, DPB1*217, DPB1*218, DPB1*219, DPB1*22, DPB1*220, DPB1*221, DPB1*222, DPB1*223, DPB1*224, DPB1*225, DPB1*226, DPB1*227, DPB1*228, DPB1*229, DPB1*23, DPB1*230, DPB1*231, DPB1*232, DPB1*233, DPB1*234, DPB1*235, DPB1*236, DPB1*237, DPB1*238, DPB1*239, DPB1*24, DPB1*240, DPB1*241, DPB1*242, DPB1*243, DPB1*244, DPB1*245, DPB1*246, DPB1*247, DPB1*248, DPB1*249, DPB1*25, DPB1*250, DPB1*251, DPB1*252, DPB1*253, DPB1*254, DPB1*255, DPB1*256, DPB1*257, DPB1*258, DPB1*259, DPB1*26, DPB1*260, DPB1*261, DPB1*262, DPB1*263, DPB1*264, DPB1*265, DPB1*266, DPB1*267, DPB1*268, DPB1*269, DPB1*27, DPB1*270, DPB1*271, DPB1*272, DPB1*273, DPB1*274, DPB1*275, DPB1*276, DPB1*277, DPB1*278, DPB1*279, DPB1*28, DPB1*280, DPB1*281, DPB1*282, DPB1*283, DPB1*284, DPB1*285, DPB1*286, DPB1*287, DPB1*288, DPB1*289, DPB1*29, DPB1*290, DPB1*291, DPB1*292, DPB1*293, DPB1*294, DPB1*295, DPB1*296, DPB1*297, DPB1*298, DPB1*299, DPB1*30, DPB1*300, DPB1*301, DPB1*302, DPB1*303, DPB1*304, DPB1*305, DPB1*306, DPB1*307, DPB1*308, DPB1*309, DPB1*31, DPB1*310, DPB1*311, DPB1*312, DPB1*313, DPB1*314, DPB1*315, DPB1*316, DPB1*317, DPB1*318, DPB1*319, DPB1*32, DPB1*320, DPB1*321, DPB1*322, DPB1*323, DPB1*324, DPB1*325, DPB1*326, DPB1*327, DPB1*328, DPB1*329, DPB1*33, DPB1*330, DPB1*331, DPB1*332, DPB1*333, DPB1*334, DPB1*335, DPB1*336, DPB1*337, DPB1*338, DPB1*339, DPB1*34, DPB1*340, DPB1*341, DPB1*342, DPB1*343, DPB1*344, DPB1*345, DPB1*346, DPB1*347, DPB1*348, DPB1*349, DPB1*35, DPB1*350, DPB1*351, DPB1*352, DPB1*353, DPB1*354, DPB1*355, DPB1*356, DPB1*357, DPB1*358, DPB1*359, DPB1*36, DPB1*360, DPB1*361, DPB1*362, DPB1*363, DPB1*364, DPB1*365, DPB1*366, DPB1*367, DPB1*368, DPB1*369, DPB1*37, DPB1*370, DPB1*371, DPB1*372, DPB1*373, DPB1*374, DPB1*375, DPB1*376, DPB1*377, DPB1*378, DPB1*379, DPB1*38, DPB1*380, DPB1*381, DPB1*382, DPB1*383, DPB1*384, DPB1*385, DPB1*386, DPB1*387, DPB1*388, DPB1*389, DPB1*39, DPB1*390, DPB1*391, DPB1*392, DPB1*393, DPB1*394, DPB1*395, DPB1*396, DPB1*397, DPB1*398, DPB1*399, DPB1*40, DPB1*400, DPB1*401, DPB1*402, DPB1*403, DPB1*404, DPB1*405, DPB1*406, DPB1*407, DPB1*408, DPB1*409, DPB1*41, DPB1*410, DPB1*411, DPB1*412, DPB1*413, DPB1*414, DPB1*415, DPB1*416, DPB1*417, DPB1*418, DPB1*419, DPB1*420, DPB1*421, DPB1*422, DPB1*423, DPB1*424, DPB1*425, DPB1*426, DPB1*427, DPB1*428, DPB1*429, DPB1*430, DPB1*431, DPB1*432, DPB1*433, DPB1*434, DPB1*435, DPB1*436, DPB1*437, DPB1*438, DPB1*439, DPB1*44, DPB1*440, DPB1*441, DPB1*442, DPB1*443, DPB1*444, DPB1*445, DPB1*446, DPB1*447, DPB1*448, DPB1*449, DPB1*45, DPB1*450, DPB1*451, DPB1*452, DPB1*453, DPB1*454, DPB1*455, DPB1*456, DPB1*457, DPB1*458, DPB1*459, DPB1*46, DPB1*460, DPB1*461, DPB1*462, DPB1*463, DPB1*464, DPB1*465, DPB1*466, DPB1*467, DPB1*468, DPB1*469, DPB1*47, DPB1*470, DPB1*471, DPB1*472, DPB1*473, DPB1*474, DPB1*475, DPB1*476, DPB1*477, DPB1*478, DPB1*479, DPB1*48, DPB1*480, DPB1*481, DPB1*482, DPB1*483, DPB1*484, DPB1*485, DPB1*486, DPB1*487, DPB1*488, DPB1*489, DPB1*49, DPB1*490, DPB1*491, DPB1*492, DPB1*493, DPB1*494, DPB1*495, DPB1*496, DPB1*497, DPB1*498, DPB1*499, DPB1*50, DPB1*500, DPB1*501, DPB1*502, DPB1*503, DPB1*504, DPB1*505, DPB1*506, DPB1*507, DPB1*508, DPB1*509, DPB1*51, DPB1*510, DPB1*511, DPB1*512, DPB1*513, DPB1*514, DPB1*515, DPB1*516, DPB1*517, DPB1*518, DPB1*519, DPB1*52, DPB1*520, DPB1*521, DPB1*522, DPB1*523, DPB1*524, DPB1*525, DPB1*526, DPB1*527, DPB1*528, DPB1*529, DPB1*53, DPB1*530, DPB1*531, DPB1*532, DPB1*533, DPB1*534, DPB1*535, DPB1*536, DPB1*537, DPB1*538, DPB1*539, DPB1*54, DPB1*540, DPB1*541, DPB1*542, DPB1*543, DPB1*544, DPB1*545, DPB1*546, DPB1*547, DPB1*548, DPB1*549, DPB1*55, DPB1*550, DPB1*551, DPB1*552, DPB1*553, DPB1*554, DPB1*555, DPB1*556, DPB1*557, DPB1*558, DPB1*559, DPB1*56, DPB1*560, DPB1*561, DPB1*562, DPB1*563, DPB1*564, DPB1*565, DPB1*566, DPB1*567, DPB1*568, DPB1*569, DPB1*57, DPB1*570, DPB1*571, DPB1*572, DPB1*573, DPB1*574, DPB1*575, DPB1*576, DPB1*577, DPB1*578, DPB1*579, DPB1*58, DPB1*580, DPB1*581, DPB1*582, DPB1*583, DPB1*584, DPB*585, DPB1*586, DPB1*587, DPB1*588, DPB1*589, DPB1*59, DPB1*590, DPB1*591, DPB1*592, DPB1*593, DPB1*594, DPB1*595, DPB1*596, DPB1*597, DPB1*598, DPB1*599, DPB1*60, DPB1*600, DPB1*601, DPB1*602, DPB1*603, DPB1*604, DPB1*605, DPB1*606, DPB1*607, DPB1*608, DPB1*609, DPB1*61, DPB1*610, DPB1*611, DPB1*612, DPB1*613, DPB1*614, DPB1*615, DPB1*616, DPB1*617, DPB1*618, DPB1*619, DPB1*62, DPB1*620, DPB1*621, DPB1*622, DPB1*623, DPB1*624, DPB1*625, DPB1*626, DPB1*627, DPB1*628, DPB1*629, DPB1*63, DPB1*630, DPB1*631, DPB1*632, DPB1*633, DPB1*634, DPB1*635, DPB1*636, DPB1*637, DPB1*638, DPB1*639, DPB1*64, DPB1*640, DPB1*641, DPB1*642, DPB1*643, DPB1*644, DPB1*645, DPB1*646, DPB1*647, DPB1*648, DPB1*649, DPB1*65, DPB1*650, DPB1*651, DPB1*652, DPB1*653, DPB1*654, DPB1*655, DPB1*656, DPB1*657, DPB1*658, DPB1*659, DPB1*66, DPB1*660, DPB1*661, DPB1*662, DPB1*663, DPB1*664, DPB1*665, DPB1*666, DPB1*667, DPB1*668, DPB1*669, DPB1*67, DPB1*670, DPB1*671, DPB1*672, DPB1*673, DPB1*674, DPB1*675, DPB1*676, DPB1*677, DPB1*678, DPB1*679, DPB1*68, DPB1*680, DPB1*681, DPB1*682, DPB1*683, DPB1*684, DPB1*685, DPB1*686, DPB1*687, DPB1*688, DPB1*689, DPB1*69, DPB1*690, DPB1*691, DPB1*692, DPB1*693, DPB1*694, DPB1*695, DPB1*696, DPB1*697, DPB1*698, DPB1*699, DPB1*70, DPB1*700, DPB1*701, DPB1*702, DPB1*703, DPB1*704, DPB1*705, DPB1*706, DPB1*707, DPB1*708, DPB1*709, DPB1*71, DPB1*710, DPB1*711, DPB1*712, DPB1*713, DPB1*714, DPB1*715, DPB1*716, DPB1*717, DPB1*718, DPB1*719, DPB1*72, DPB1*720, DPB1*721, DPB1*722, DPB1*723, DPB1*724, DPB1*725, DPB1*726, DPB1*727, DPB1*728, DPB1*729, DPB1*73, DPB1*730, DPB1*731, DPB1*732, DPB1*733, DPB1*734, DPB1*735, DPB1*736, DPB1*737, DPB1*738, DPB1*739, DPB1*74, DPB1*740, DPB1*741, DPB1*742, DPB1*743, DPB1*744, DPB1*745, DPB1*746, DPB1*747, DPB1*748, DPB1*749, DPB1*75, DPB1*750, DPB1*751, DPB1*752, DPB1*753, DPB1*754, DPB1*755, DPB1*756, DPB1*757, DPB1*758, DPB1*759, DPB1*76, DPB1*760, DPB1*761, DPB1*762, DPB1*763, DPB1*764, DPB1*765, DPB1*766, DPB1*767, DPB1*768, DPB1*769, DPB1*77, DPB1*770, DPB1*771, DPB1*772, DPB1*773, DPB1*774, DPB1*775, DPB1*776, DPB1*777, DPB1*778, DPB1*779, DPB1*78, DPB1*780, DPB1*781, DPB1*782, DPB1*783, DPB1*784, DPB1*785, DPB1*786, DPB1*787, DPB1*788, DPB1*789, DPB1*79, DPB1*790, DPB1*791, DPB1*792, DPB1*794, DPB1*795, DPB1*796, DPB1*797, DPB1*798, DPB1*799, DPB1*80, DPB1*800, DPB1*801, DPB1*802, DPB1*803, DPB1*804, DPB1*805, DPB1*806, DPB1*807, DPB1*808, DPB1*809, DPB1*81, DPB1*810, DPB1*811, DPB1*812, DPB1*813, DPB1*814, DPB1*815, DPB1*816, DPB1*817, DPB1*818, DPB1*819, DPB1*82, DPB1*820, DPB1*821, DPB1*822, DPB1*823, DPB1*824, DPB1*825, DPB1*826, DPB1*827, DPB1*828, DPB1*829, DPB1*83, DPB1*830, DPB1*831, DPB1*832, DPB1*833, DPB1*834, DPB1*835, DPB1*836, DPB1*837, DPB1*838, DPB1*839, DPB1*84, DPB1*840, DPB1*841, DPB1*842, DPB1*843, DPB1*844, DPB1*845, DPB1*846, DPB1*847, DPB1*848, DPB1*849, DPB1*85, DPB1*850, DPB1*851, DPB1*852, DPB1*853, DPB1*854, DPB1*855, DPB1*856, DPB1*857, DPB1*858, DPB1*859, DPB1*86, DPB1*860, DPB1*861, DPB1*862, DPB1*863, DPB1*864, DPB1*865, DPB1*866, DPB1*867, DPB1*868, DPB1*869, DPB1*87, DPB1*870, DPB1*871, DPB1*872, DPB1*873, DPB1*874, DPB1*875, DPB1*876, DPB1*877, DPB1*878, DPB1*879, DPB1*88, DPB1*880, DPB1*881, DPB1*882, DPB1*883, DPB1*884, DPB1*885, DPB1*886, DPB1*887, DPB1*888, DPB1*889, DPB1*89, DPB1*890, DPB1*891, DPB1*892, DPB1*893, DPB1*894, DPB1*895, DPB1*896, DPB1*897, DPB1*898, DPB1*899, DPB1*90, DPB1*900, DPB1*901, DPB1*902, DPB1*903, DPB1*904, DPB1*905, DPB1*906, DPB1*907, DPB1*908, DPB1*909, DPB1*91, DPB1*910, DPB1*911, DPB1*912, DPB1*913, DPB1*914, DPB1*915, DPB1*916, DPB1*917, DPB1*918, DPB1*919, DPB1*92, DPB1*920, DPB1*921, DPB1*922, DPB1*923, DPB1*924, DPB1*925, DPB1*926, DPB1*927, DPB1*928, DPB1*929, DPB1*93, DPB1*930, DPB1*931, DPB1*932, DPB1*933, DPB1*934, DPB1*935, DPB1*936, DPB1*937, DPB1*938, DPB1*939, DPB1*94, DPB1*940, DPB1*941, DPB1*942, DPB1*943, DPB1*944, DPB1*945, DPB1*946, DPB1*947, DPB1*948, DPB1*949, DPB1*95, DPB1*950, DPB1*951, DPB1*952, DPB1*953, DPB1*954, DPB1*955, DPB1*956, DPB1*957, DPB1*958, DPB1*959, DPB1*96, DPB1*960, DPB1*961, DPB1*962, DPB1*963, DPB1*964, DPB1*965, DPB1*97, DPB1*98, and DPB1*99. In some aspects, the DP beta chain comprises an HLA-DPB1*01, HLA-DPB1*02, HLA-DPB1*01, HLA-DPB1*03, HLA-DPB1*04, HLA-DPB1*05, HLA-DPB1*06, HLA-DPB1*08, HLA-DPB1*09 allele, and any combination thereof. In certain aspects, the DP beta chain comprises an HLA-DPB1*04 allele. In particular aspects, the DP beta chain comprises an HLA-DPB1*04:01 allele.

In some aspects, the DP beta chain comprises an allele selected from DPB1*01:01:01:01, DPB1*01:01:01:02, DPB1*01:01:01:03, DPB1*01:01:01:04, DPB1*01:01:01:05, DPB1*01:01:01:06, DPB1*01:01:01:07, DPB1*01:01:01:08, DPB1*01:01:01:09, DPB1*01:01:01:10, DPB1*01:01:02:01, DPB1*01:01:02:02, DPB1*01:01:03, DPB1*01:01:04, DPB1*01:01:05, DPB1*01:01:06, DPB1*02:01:02:01, DPB1*02:01:02:02, DPB1*02:01:02:03, DPB1*02:01:02:04, DPB1.*02:01:02:05, DPB1*02:01:02:06, DPB1*02:01:02:07, DPB1*02:01:02:08, DPB1*02:01:02:09, DPB1*02:01:02:1.0, DPB1*02:01:02:11, DPB1*02:01:

0212, DPB1*02:01:02:13, DPB1*02:01:02:14, DPB1*02:
01:02:15, DPB1*02:01:02:16, DPB1*02:01:02:17,
DPB1*02:01:02:18, DPB1*02:01:02:19, DPB1*02:01:02:
20, DPB1*02:01:02:21, DPB1*02:01:02:22, DPB1*02:01:
02:23, DPB1*02:01:02:24, DPB1*02:01:02:25, DPB1*02:
01:02:26, DPB1*02:01:02:27, DPB1*02:01:02:28,
DPB1*02:01:02:29, DPB1*02:01:02:30, DPB1*02:01:02:
31, DPB1*02:01:02:32, DPB1*02:01:02:33, DPB1*02:01:
02:34, DPB1*02:01:02:35, DPB1*02:01:02:36, DPB1*02:
01:02:37, DPB1*02:01:02:38, DPB1*02:01:02:39,
DPB1*02:01:02:40, DPB1.*02:01:02:41, DPB1*02:01:02:
42, DPB1*02:01:02:43, DPB1*02:01:03, DPB1*02:01:04,
DPB1*02:01:05, DPB1*02:01:06, DPB1.*02:01:07,
DPB1*02:01:08, DPB1*02:01:09, DPB1.*02:01:10,
DPB1*02:01:11, DPB1*02:01:12, DPB1*02:01:13,
DPB1*02:01:14, DPB1*02:01:15, DPB1*02:01:16,
DPB1*02:01:17, DPB1*02:01:18, DPB1*02:0119,
DPB1*02:01:20, DPB1*02:01:21, DPB1*02:01:22,
DPB1*02:01:23, DPB1*02:01:24, DPB1*02:01:25,
DPB1*02:01:26, DPB1*02:01:27, DPB1*2:01:28,
DPB1*02:01:29, DPB1*02:01:30, DPB1*02:01:31,
DPB1*02:01:32, DPB1*02:01:33, DPB1*02:01:34,
DPB1*02:01:35, DPB1*02:01:36, DPB1*02:01:37,
DPB1*02:01:38, DPB1*02:01:39, DPB1*02:01:40,
DPB1*02:01:41, DPB1*02:01:42, DPB1*02:01:43,
DPB1*02:02:01:01, DPB1*02:02:01:02, DPB1*02:02:01:
03, DPB1*02:02:01:04, DPB1*02:02:01:05, DPB1*02:02:
01:06, DPB1*02:02:01:07, DPB1*02:02:02, DPB1*02:02:
03, DPB1*03:01:01:01, DPB1*03:01:01:02, DPB1*03:01:
01:03, DPB1*03:01:01:04, DPB1*03:01:01:05, DPB1*03:
01:01:06, DPB1*03:01:01:07, DPB1*03:01:01:08,
DPB1.*03:01:01:09, DPB1*03:01:01:10, DPB1*03:01:01:
11, DPB1*03:01:02, DPB1*03:01:03, DPB1*03:01:04,
DPB1*03:01:05, DPB1*03:01:06, DPB1*03:01:07,
DPB1*03:01:08, DPB1*03:01:09, DPB1*03:01:10,
DPB1*03:01:11, DPB1*03:01:12, DPB1*04:01:01:01,
DPB1*04:01:01:02, DPB1*04:01:01:03, DPB1*04:01:01:
04, DPB1*04:01:01:05, DPB1*04:01:01:06, DPB1*04:01:
01:07, DPB1*04:01:01:08, DPB1*04:01:01:09, DPB1*04:
01:01:10, DPB1*04:01:01:11, DPB1*04:01:01:12,
DPB1*04:01:01:13, DPB1*04:01:01:14, DPB1*04:01:01:
15, DPB1*04:01:01:16, DPB1*04:01:01:17, DPB1*04:01:
01:18, DPB1*04:01:01:19, DPB1*04:01:01:20, DPB1*04:
01:01:21, DPB1*04:01:01:22, DPB1*04:01:01:23,
DPB1*04:01:01:24N, DPB1*04:01:01:25, DPB1*04:01:01:
26, DPB1*04:01:01:27, DPB1*04:01:01:28, DPB1*04:01:
01:29, DPB1*04:01:01:30, DPB1*04:01:01:31, DPB1*04:
01:01:32, DPB1*04:01:01:33, DPB1*04:01:01:34,
DPB1*04:01:02, DPB1*04:01:03, DPB1*04:01:04:01,
DPB1*04:01:04:02, DPB1*04:01:05, DPB1*04:01:06,
DPB1*04:01:07, DPB1*04:01:08, DPB1*04:01:09,
DPB1*04:01:10, DPB1*04:01:11, DPB1*04:01:12,
DPB1*04:01:13, DPB1*04:01:14, DPB1*04:01:15,
DPB1*04:01:16, DPB1*04:01:17, DPB1*04:01:18,
DPB1*04:01:19, DPB1*04:01:20, DPB1*04:01:21,
DPB1*04:01:22, DPB1*04:01:23, DPB1*04:01:24,
DPB1*04:01:25, DPB1*04:01:26, DPB1*04:01:27,
DPB1*04:01:28, DPB1*04:01:29, DPB1*04:01:30,
DPB1*04:01:31, DPB1*04:01:32, DPB1*04:01:33,
DPB1*04:01:34, DPB1*04:01:35, DPB1*04:01:36,
DPB1*04:01:37, DPB1*04:01:38, DPB1*04:01:39,
DPB1*04:01:40, DPB1*04:02:01:01, DPB1*04:02:01:02,
DPB1*04:02:01:03, DPB1*04:02:01:04, DPB1*04:02:01:
05, DPB1*04:02:01:06, DPB1*04:02:01:07, DPB1*04:02:
01:08, DPB1*04:02:01:09, DPB1*04:02:01:10, DPB1*04:
02:01:11, DPB1*04:02:01:12, DPB1*04:02:01:13,
DPB1*04:02:01:14, DPB1*04:02:02, DPB1*04:02:03,

DPB1*04:02:04, DPB1*04:02:05, DPB1*04:02:06,
DPB1*04:02:07, DPB1*04:02:08, DPB1*04:02:09,
DPB1*04:02:10, DPB1*04:02:11, DPB1*04:02:12,
DPB1*04:02:13, DPB1*04:02:14, DPB1*05:01:01:01,
DPB1*05:01:01:02, DPB1*05:01:01:03, DPB1*05:01:01:
04, DPB1*05:01:01:05, DPB1*05:01:01:06, DPB1*05:01:
01:07, DPB1*05:01:01:08, DPB1*05:01:01:09, DPB1*05:
01:01:10, DPB1*05:01:02, DPB1*05:01:03, DPB1*05:01:
04, DPB1*05:01:05, DPB1*05:01:06, DPB1*05:01:07,
DPB1*05:01:08, DPB1*05:01:09, DPB1*06:01:01:01,
DPB1*06:01:01:02, DPB1*06:01:01:03, DPB1*06:01:02,
DPB1*06:01:03, DPB1*06:01:04, DPB1*06:01:05,
DPB1*08:01, DPB1*09:01:01, DPB1*09:01:02, DPB1*09:
01:03, DPB1*09:01:04, DPB1*100:01, DPB1*101:01,
DPB1*102:01, DPB1*103:01, DPB1*104:01:01:01,
DPB1*104:01:01:02, DPB1*104:01:01:03, DPB1*104:01:
01:04, DPB1*104:01:01:05, DPB1*104:01:01:06,
DPB1*104:01:02, DPB1*105:01:01:01, DPB1*105:01:01:
02, DPB1*105:01:01:03, DPB1*105:01:01:04, DPB1*105:
01:01:05, DPB1*105:01:01:06, DPB1*105:01:01:07,
DPB1*105:01:01:08, DPB1*105:01:01:09, DPB1*105:01:
01:10, DPB1*106:01, DPB1*107:01, DPB1*108:01,
DPB1*109:01, DPB1*10:01:01:01, DPB1*10:01:01:02,
DPB1*10:01:02, DPB1*10:01:03, DPB1*10:01:04,
DPB1*110:01, DPB1*111:01, DPB1*112:01, DPB1*113:
01, DPB1*114:01, DPB1*115:01, DPB1*116:01,
DPB1*117:01, DPB1*118:01, DPB1*119:01, DPB1*11:01:
01:01, DPB1*11:01:01:02, DPB1*11:01:02, DPB1*11:01:
03, DPB1*11:01:04, DPB1*120:01N, DPB1*121:01,
DPB1*122:01, DPB1*123:01, DPB1*124:01:01:01,
DPB1*124:01:01:02, DPB1*124:01:02:01, DPB1*124:01:
02:02, DPB1*125:01, DPB1*126:01:01:01, DPB1*126:01:
01:02, DPB1*127:01, DPB1*128:01, DPB1*129:01,
DPB1*130:01, DPB1*131:01:01:01, DPB1*131:01:01:02,
DPB1*131:01:02, DPB1*131:01:03, DPB1*132:01,
DPB1*133:01, DPB1*134:01, DPB1*135:01, DPB1*136:
01, DPB1*137:01, DPB1*138:01, DPB1*139:01,
DPB1*13:01:01:01, DPB1*13:01:01:02, DPB1*13:01:01:
03, DPB1*13:01:01:04, DPB1*13:01:01:05, DPB1*13:01:
01:06, DPB1*13:01:01:07, DPB1*13:01:01:08, DPB1*13:
01:02, DPB1*13:01:03, DPB1*140:01, DPB1*141:01,
DPB1*142:01, DPB1*143:01, DPB1*144:01, DPB1*145:
01, DPB1*146:01, DPB1*147:01, DPB1*148:01,
DPB1*149:01, DPB1*14:01:01, DPB1*14:01:01:02,
DPB1*14:01:01:03, DPB1*14:01:02, DPB1*14:01:03,
DPB1*14:01:04, DPB1*14:01:05, DPB1*14:01:06,
DPB1*14:01:07, DPB1*14:01:08, DPB1*14:01:09,
DPB1*150:01, DPB1*151:01, DPB1*152:01, DPB1*153:
01, DPB1*154:01N, DPB1*155:01:01, DPB1*155:01:02,
DPB1*156:01, DPB1*157:01, DPB1*158:01, DPB1*159:
01N, DPB1*15:01:01:01, DPB1*15:01:01:02, DPB1*15:
01:01:03, DPB1*15:01:01:04, DPB1*15:01:02, DPB1*15:
01:03, DPB1*160:01, DPB1*161:01N, DPB1*162:01:01,
DPB1*162:01:02, DPB1*163:01, DPB1*164:01,
DPB1*165:01, DPB1*166:01, DPB1*167:01, DPB1*168:
01, DPB1*169:01, DPB1*16:01:01:01, DPB1*16:01:01:02,
DPB1*16:01:02, DPB1*16:01:03, DPB1*170:01,
DPB1*171:01, DPB1*172:01, DPB1*173:01, DPB1*174:
01, DPB1*175:01, DPB1*176:01, DPB1*177:01,
DPB1*178:01, DPB1*179:01, DPB1*17:01:01:01,
DPB1*17:01:01:02, DPB1*17:01:02, DPB1*17:01:03,
DPB1*180:01, DPB1*181:01, DPB1*182:01, DPB1*183:
01, DPB1*184:01, DPB1*185:01, DPB1*186:01,
DPB1*187:01, DPB1*188:01, DPB1*189:01, DPB1*18:
01:01:01, DPB1*18:01:01:02, DPB1*18:01:01:03,
DPB1*18:01:02, DPB1*18:01:03, DPB1*190:01,
DPB1*191:01, DPB1*192:01, DPB1*193:01, DPB1*194:

01, DPB1*195:01, DPB1*196:01, DPB1*197:01, DPB1*198:01, DPB1*199:01, DPB1*19:01:01:01, DPB1*19:01:01:02, DPB1*19:01:01:03, DPB1*200:01, DPB1*201:01, DPB1*202:01, DPB1*203:01:01, DPB1*203:01:02, DPB1*204:01, DPB1*205:01, DPB1*206:01, DPB1*207:01, DPB1*208:01, DPB1*209:01, DPB1*20:01:01:01, DPB1*20:01:01:02, DPB1*20:01:02, DPB1*20:01:03, DPB1*20:01:04, DPB1*210:01, DPB1*211:01, DPB1*212:01, DPB1*213:01:01, DPB1*213:01:02, DPB1*214:01, DPB1*215:01, DPB1*216:01N, DPB1*217:01, DPB1*218:01N, DPB1*219:01, DPB1*21:01, DPB1*220:01, DPB1*221:01, DPB1*222:01, DPB1*223:01, DPB1*224:01, DPB1*225:01, DPB1*226:01, DPB1*227:01:01, DPB1*227:01:02, DPB1*228:01, DPB1*229:01, DPB1*22:01:01:01, DPB1*22:01:01:02, DPB1*230:01, DPB1*231:01, DPB1*232:01, DPB1*233:01, DPB1*234:01, DPB1*235:01, DPB1*236:01:01, DPB1*236:01:02, DPB1*237:01, DPB1*238:01, DPB1*239:01, DPB1*23:01:01:01, DPB1*23:01:01:02, DPB1*23:01:02, DPB1*240:01, DPB1*241:01, DPB1*242:01, DPB1*243:01, DPB1*244:01, DPB1*245:01, DPB1*246:01, DPB1*247:01, DPB1*248:01, DPB1*249:01, DPB1*24:01, DPB1*250:01, DPB1*251:01, DPB1*252:01, DPB1*253:01, DPB1*254:01, DPB1*255:01, DPB1*256:01, DPB1*257:01, DPB1*258:01, DPB1*259:01, DPB1*25:01, DPB1*260:01, DPB1*261:01, DPB1*262:01, DPB1*263:01, DPB1*264:01, DPB1*265:01, DPB1*266:01, DPB1*267:01, DPB1*268:01, DPB1*269:01, DPB1*26:01:01, DPB1*26:01:02, DPB1*26:01:03, DPB1*270:01, DPB1*271:01, DPB1*272:01, DPB1*273:01, DPB1*274:01, DPB1*275:01, DPB1*276:01, DPB1*277:01, DPB1*278:01, DPB1*279:01:01, DPB1*279:01:02, DPB1*27:01, DPB1*280:01, DPB1*281:01, DPB1*282:01, DPB1*283:01, DPB1*284:01, DPB1*285:01, DPB1*286:01, DPB1*287:01, DPB1*288:01, DPB1*289:01, DPB1*28:01, DPB1*290:01, DPB1*291:01, DPB1*292:01, DPB1*293:01, DPB1*294:01, DPB1*295:01, DPB1*296:01, DPB1*297:01, DPB1*298:01, DPB1*299:01, DPB1*29:01, DPB1*300:01, DPB1*301:01, DPB1*302:01, DPB1*303:01, DPB1*304:01, DPB1*305:01, DPB1*306:01, DPB1*307:01, DPB1*308:01, DPB1*309:01, DPB1*30:01:01:01, DPB1*30:01:01:02, DPB1*310:01, DPB1*311:01, DPB1*312:01, DPB1*313:01, DPB1*314:01, DPB1*315:01, DPB1*316:01, DPB1*317:01, DPB1*318:01, DPB1*319:01, DPB1*31:01:01:01, DPB1*31:01:01:02, DPB1*320:01, DPB1*321:01, DPB1*322:01, DPB1*323:01, DPB1*324:01, DPB1*325:01, DPB1*326:01, DPB1*327:01, DPB1*328:01N, DPB1*329:01, DPB1*32:01, DPB1*330:01, DPB1*331:01, DPB1*332:01, DPB1*333:01, DPB1*334:01, DPB1*335:01, DPB1*336:01, DPB1*337:01, DPB1*338:01, DPB1*339:01, DPB1*33:01:01:01, DPB1*33:01:01:02, DPB1*33:01:01:03, DPB1*33:01:01:04, DPB1*33:01:01:05, DPB1*340:01, DPB1*341:01, DPB1*342:01, DPB1*343:01, DPB1*344:01, DPB1*345:01, DPB1*346:01, DPB1*347:01, DPB1*348:01:01, DPB1*348:01:02, DPB1*349:01, DPB1*34:01:01:01, DPB1*34:01:01:02, DPB1*34:01:02, DPB1*350:01, DPB1*351:01, DPB1*352:01:01, DPB1*352:01:02, DPB1*353:01, DPB1*354:01:01, DPB1*354:01:02, DPB1*355:01, DPB1*356:01, DPB1*357:01N, DPB1*358:01, DPB1*359:01, DPB1*35:01:01, DPB1*360:01, DPB1*361:01, DPB1*362:01, DPB1*363:01, DPB1*364:01, DPB1*365:01, DPB1*366:01, DPB1*367:01, DPB1*368:01, DPB1*369:01, DPB1*36:01, DPB1*370:01, DPB1*371:01, DPB1*372:01, DPB1*373:01, DPB1*374:01, DPB1*375:01, DPB1*376:

01, DPB1*377:01, DPB1*378:01, DPB1*379:01, DPB1*37:01, DPB1*380:01, DPB1*381:01, DPB1*382:01N, DPB1*383:01, DPB1*384:01, DPB1*385:01, DPB1*386:01, DPB1*387:01, DPB1*388:01, DPB1*389:01, DPB1*38:01, DPB1*390:01, DPB1*391:01, DPB1*392:01, DPB1*393:01, DPB1*394:01, DPB1*395:01, DPB1*396:01, DPB1*397:01, DPB1*398:01, DPB1*399:01, DPB1*39:01:01:01, DPB1*39:01:01:02, DPB1*39:01:01:03, DPB1*39:01:01:04, DPB1*39:01:02, DPB1*39:01:03, DPB1*400:01, DPB1*401:01N, DPB1*402:01, DPB1*403:01N, DPB1*404:01, DPB1*405:01, DPB1*406:01, DPB1*407:01, DPB1*408:01, DPB1*409:01, DPB1*40:01:01:01, DPB1*40:01:01:02, DPB1*40:01:01:03, DPB1*40:01:02, DPB1*410:01, DPB1*411:01, DPB1*412:01, DPB1*413:01, DPB1*414:01:01:01, DPB1*414:01:01:02, DPB1*415:01, DPB1*416:01:01:01, DPB1*416:01:01:02, DPB1*416:01:01:03, DPB1*416:01:02, DPB1*417:01:01, DPB1*417:01:02, DPB1*418:01, DPB1*419:01, DPB1*41:01:01:01 DPB1*41:01:01:02, DPB1*41:01:02, DPB1*420:01, DPB1*421:01, DPB1*422:01, DPB1*423:01:01, DPB1*423:01:02, DPB1*424:01, DPB1*425:01, DPB1*426:01, DPB1*427:01, DPB1*428:01, DPB1*429:01, DPB1*430:01, DPB1*431:01, DPB1*432:01, DPB1*433:01, DPB1*434:01, DPB1*435:01, DPB1*436:01, DPB1*437:01, DPB1*438:01, DPB1*439:01, DPB1*440:01, DPB1*441:01, DPB1*442:01, DPB1*443:01, DPB1*444:01, DPB1*445:01, DPB1*446:01, DPB1*447:01, DPB1*448:01, DPB1*449:01, DPB1*44:01, DPB1*450:01N, DPB1*451:01, DPB1*452:01, DPB1*453:01, DPB1*454:01, DPB1*455:01N, DPB1*456:01, DPB1*457:01, DPB1*458:01, DPB1*459:01, DPB1*45:01, DPB1*460:01, DPB1*461:01, DPB1*462:01, DPB1*463:01:01:01, DPB1*463:01:01:02, DPB1*463:01:01:03, DPB1*464:01, DPB1*465:01, DPB1*466:01, DPB1*467:01, DPB1*468:01, DPB1*469:01, DPB1*46:01:01, DPB1*46:01:02, DPB1*470:01, DPB1*471:01, DPB1*472:01, DPB1*473:01, DPB1*474:01, DPB1*475:01, DPB1*476:01, DPB1*477:01, DPB1*478:01, DPB1*479:01, DPB1*47:01:01:01, DPB1*47:01:01:02, DPB1*47:01:01:03, DPB1*480:01, DPB1*481:01, DPB1*482:01, DPB1*483:01, DPB1*484:01, DPB1*485:01, DPB1*486:01, DPB1*487:01, DPB1*488:01, DPB1*489:01, DPB1*48:01, DPB1*490:01, DPB1*491:01, DPB1*492:01, DPB1*493:01, DPB1*494:01, DPB1*495:01, DPB1*496:01, DPB1*497:01, DPB1*498:01, DPB1*499:01, DPB1*49:01:01:01, DPB1*49:01:01:02, DPB1*49:01:01:03, DPB1*500:01, DPB1*501:01, DPB1*502:01, DPB1*503:01, DPB1*504:01, DPB1*505:01, DPB1*506:01, DPB1*507:01N, DPB1*508:01, DPB1*509:01, DPB1*50:01, DPB1*510:01, DPB1*511:01, DPB1*512:01, DPB1*513:01, DPB1*514:01, DPB1*515:01, DPB1*516:01, DPB1*517:01, DPB1*518:01, DPB1*519:01, DPB1*51:01:01:01, DPB1*51:01:01:02, DPB1*520:01, DPB1*521:01, DPB1*522:01, DPB1*523:01:01, DPB1*523:01:02, DPB1*524:01, DPB1*525:01, DPB1*526:01, DPB1*527:01, DPB1*528:01, DPB1*529:01, DPB1*52:01, DPB1*530:01, DPB1*531:01, DPB1*532:01, DPB1*533:01, DPB1*534:01, DPB1*535:01, DPB1*536:01, DPB1*537:01, DPB1*538:01, DPB1*539:01, DPB1*53:01, DPB1*540:01, DPB1*541:01, DPB1*542:01, DPB1*543:01, DPB1*544:01, DPB1*545:01, DPB1*546:01, DPB1*547:01, DPB1*548:01, DPB1*549:01, DPB1*54:01, DPB1*550:01, DPB1*551:01N, DPB1*552:01, DPB1*553:01, DPB1*554:01, DPB1*555:01, DPB1*556:01, DPB1*557:01, DPB1*558:01, DPB1*559:01, DPB1*55:01:01:01, DPB1*55:01:01:02,

DPB1*55:01:01:03, DPB1*55:01:01:04, DPB1*55:01:01:05, DPB1*55:01:02, DPB1*560:01, DPB1*561:01, DPB1*562:01, DPB1*563:01, DPB1*564:01, DPB1*565:01, DPB1*566:01, DPB1*567:01, DPB1*568:01, DPB1*569:01, DPB1*56:01, DPB1*570:01N, DPB1*571:01, DPB1*572:01, DPB1*573:01, DPB1*574:01, DPB1*575:01, DPB1*576:01, DPB1*577:01, DPB1*578:01, DPB1*579:01, DPB1*57:01, DPB1*580:01, DPB1*581:01, DPB1*582:01, DPB1*583:01, DPB1*584:01:01:01, DPB1*584:01:01:02, DPB1*584:01:01:03, DPB1*584:01:02:01, DPB1*584:01:02:02, DPB1*585:01:01:01, DPB1*585:01:01:02, DPB1*586:01, DPB1*587:01, DPB1*588:01, DPB1*589:01, DPB1*58:01, DPB1*590:01, DPB1*591:01, DPB1*592:01, DPB1*593:01, DPB1*594:01, DPB1*595:01, DPB1*596:01, DPB1*597:01, DPB1*598:01N, DPB1*599:01, DPB1*59:01, DPB1*600:01, DPB1*601:01, DPB1*602:01, DPB1*603:01, DPB1*604:01, DPB1*605:01, DPB1*606:01, DPB1*607:01, DPB1*608:01, DPB1*609:01, DPB1*60:01, DPB1*610:01, DPB1*611:01, DPB1*612:01, DPB1*613:01, DPB1*614:01, DPB1*615:01, DPB1*616:01, DPB1*617:01, DPB1*618:01, DPB1*619:01, DPB1*61:01N, DPB1*620:01, DPB1*621:01, DPB1*622:01, DPB1*623:01, DPB1*624:01, DPB1*625:01, DPB1*626:01, DPB1*627:01, DPB1*628:01, DPB1*629:01, DPB1*62:01, DPB1*630:01, DPB1*631:01, DPB1*632:01, DPB1*633:01, DPB1*634:01, DPB1*635:01, DPB1*636:01, DPB1*637:01, DPB1*638:01, DPB1*639:01, DPB1*63:01, DPB1*640:01, DPB1*641:01, DPB1*642:01, DPB1*643:01, DPB1*644:01, DPB1*645:01, DPB1*646:01, DPB1*647:01, DPB1*648:01:01:01, DPB1*648:01:01:02, DPB1*649:01, DPB1*64:01N, DPB1*650:01, DPB1*651:01, DPB1*652:01, DPB1*653:01, DPB1*654:01, DPB1*655:01, DPB1*656:01, DPB1*657:01N, DPB1*658:01, DPB1*659:01, DPB1*65:01:01, DPB1*65:01:02, DPB1*660:01, DPB1*661:01N, DPB1*662:01, DPB1*663:01, DPB1*664:01, DPB1*665:01, DPB1*666:01, DPB1*667:01, DPB1*668:01:01:01, DPB1*668:01:01:02, DPB1*669:01, DPB1*66:01, DPB1*670:01, DPB1*671:01, DPB1*672:01, DPB1*673:01, DPB1*674:01, DPB1*675:01, DPB1*676:01, DPB1*677:01, DPB1*678:01, DPB1*679:01, DPB1*67:01, DPB1*680:01, DPB1*681:01, DPB1*682:01, DPB1*683:01, DPB1*684:01, DPB1*685:01, DPB1*686:01, DPB1*687:01, DPB1*688:01, DPB1*689:01, DPB1*68:01, DPB1*690:01, DPB1*691:01N, DPB1*692:01, DPB1*693:01N, DPB1*694:01, DPB1*695:01, DPB1*696:01N, DPB1*697:01Q, DPB1*698:01, DPB1*699:01, DPB1*69:01:01:01, DPB1*69:01:01:02, DPB1*700:01N, DPB1*701:01, DPB1*702:01, DPB1*703:01, DPB1*704:01, DPB1*705:01, DPB1*706:01, DPB1*707:01, DPB1*708:01, DPB1*709:01, DPB1*70:01, DPB1*710:01, DPB1*711:01, DPB1*712:01N, DPB1*713:01, DPB1*714:01, DPB1*715:01, DPB1*716:01, DPB1*717:01, DPB1*718:01, DPB1*719:01, DPB1*71:01:01, DPB1*71:01:02, DPB1*720:01, DPB1*721:01, DPB1*722:01, DPB1*723:01, DPB1*724:01N, DPB1*725:01, DPB1*726:01, DPB1*727:01, DPB1*728:01, DPB1*729:01, DPB1*72:01:01:01, DPB1*72:01:01:02, DPB1*72:01:01:03, DPB1*730:01, DPB1*731:01, DPB1*732:01N, DPB1*733:01, DPB1*734:01, DPB1*735:01, DPB1*736:01, DPB1*737:01, DPB1*738:01N, DPB1*739:01, DPB1*73:01, DPB1*740:01, DPB1*741:01, DPB1*742:01, DPB1*743:01N, DPB1*744:01, DPB1*745:01, DPB1*746:01, DPB1*747:01, DPB1*748:01N, DPB1*749:01, DPB1*74:01, DPB1*750:01, DPB1*751:01, DPB1*752:01, DPB1*753:01, DPB1*754:01N, DPB1*755:01, DPB1*756:01N, DPB1*757:01, DPB1*758:01, DPB1*759:01, DPB1*75:01, DPB1*760:01, DPB1*761:01, DPB1*762:01, DPB1*763:01, DPB1*764:01, DPB1*765:01, DPB1*766:01, DPB1*767:01, DPB1*768:01, DPB1*769:01, DPB1*76:01, DPB1*770:01, DPB1*771:01, DPB1*772:01, DPB1*773:01, DPB1*774:01, DPB1*775:01, DPB1*776:01, DPB1*777:01N, DPB1*778:01, DPB1*779:01, DPB1*77:01, DPB1*780:01, DPB1*781:01, DPB1*782:01, DPB1*783:01, DPB1*784:01, DPB1*785:01, DPB1*786:01:01N, DPB1*786:01:02N, DPB1*787:01, DPB1*788:01, DPB1*789:01, DPB1*78:01, DPB1*790:01, DPB1*791:01, DPB1*792:01N, DPB1*794:01N, DPB1*795:01, DPB1*796:01, DPB1*797:01, DPB1*798:01, DPB1*799:01, DPB1*79:01, DPB1*800:01N, DPB1*801:01, DPB1*802:01, DPB1*803:01, DPB1*804:01, DPB1*805:01, DPB1*806:01:01:01, DPB1*806:01:01:02, DPB1*807:01, DPB1*808:01, DPB1*809:01, DPB1*80:01, DPB1*810:01, DPB1*811:01, DPB1*812:01, DPB1*813:01, DPB1*814:01, DPB1*815:01, DPB1*816:01, DPB1*817:01, DPB1*818:01, DPB1*819:01, DPB1*81:01:01:01, DPB1*81:01:01:02, DPB1*81:01:02, DPB1*820:01, DPB1*821:01N, DPB1*822:01, DPB1*823:01, DPB1*824:01, DPB1*825:01, DPB1*826:01, DPB1*827:01, DPB1*828:01, DPB1*829:01, DPB1*82:01, DPB1*830:01, DPB1*831:01N, DPB1*832:01, DPB1*833:01, DPB1*834:01, DPB1*835:01, DPB1*836:01 DPB1*837:01, DPB1*838:01N, DPB1*839:01, DPB1*83:01, DPB1*840:01, DPB1*841:01, DPB1*842:01, DPB1*843:01, DPB1*844:01N, DPB1*845:01, DPB1*846:01, DPB1*847:01, DPB1*848:01, DPB1*849:01, DPB1*84:01, DPB1*850:01, DPB1*851:01, DPB1*852:01, DPB1*853:01, DPB1*854:01, DPB1*855:01, DPB1*856:01, DPB1*857:01, DPB1*858:01, DPB1*859:01, DPB1*85:01:01:01, DPB1*85:01:01:02, DPB1*85:01:02, DPB1*860:01, DPB1*861:01, DPB1*862:01N, DPB1*863:01, DPB1*864:01, DPB1*865:01N, DPB1*866:01N, DPB1*867:01N, DPB1*868:01N, DPB1*869:01N, DPB1*86:01, DPB1*870:01N, DPB1*871:01N, DPB1*872:01N, DPB1*873:01N, DPB1*874:01N, DPB1*875:01N, DPB1*876:01N, DPB1*877:01N, DPB1*878:01N, DPB1*879:01:01:01, DPB1*879:01:01:02, DPB1*879:01:01:03, DPB1*87:01, DPB1*880:01, DPB1*881:01, DPB1*882:01, DPB1*883:01, DPB1*884:01, DPB1*885:01, DPB1*886:01, DPB1*887:01 DPB1*888:01, DPB1*889:01, DPB1*88:01, DPB1*890:01, DPB1*891:01, DPB1*892:01, DPB1*893:01, DPB1*894:01N, DPB1*895:01, DPB1*896:01, DPB1*897:01, DPB1*898:01, DPB1*899:01, DPB1*89:01, DPB1*900:01, DPB1*901:01, DPB1*902:01, DPB1*903:01, DPB1*904:01, DPB1*905:01, DPB1*906:01, DPB1*907:01, DPB1*908:01, DPB1*909:01, DPB1*90:01:01, DPB1*90:01:02, DPB1*910:01, DPB1*911:01N, DPB1*912:01, DPB1*913:01, DPB1*914:01, DPB1*915:01, DPB1*916:01, DPB1*917:01N, DPB1*918:01, DPB1*919:01N, DPB1*91:01:01:01, DPB1*91:01:01:02, DPB1*920:01, DPB1*921:01, DPB1*922:01, DPB1*923:01, DPB1*924:01, DPB1*925:01N, DPB1*926:01, DPB1*927:01, DPB1*928:01, DPB1*929:01, DPB1*92:01, DPB1*930:01, DPB1*931:01, DPB1*932:01, DPB1*933:01, DPB1*934:01Q, DPB1*935:01Q, DPB1*936:01Q, DPB1*937:01, DPB1*938:01, DPB1*939:01N, DPB1*93:01, DPB1*940:01, DPB1*941:01N, DPB1*942:01, DPB1*943:01, DPB1*944:01, DPB1*945:01, DPB1*946:01, DPB1*947:01, DPB1*948:01, DPB1*949:01, DPB1*94:01, DPB1*950:01N, DPB1*951:01, DPB1*952:01, DPB1*953:01, DPB1*954:01, DPB1*955:01, DPB1*956:01, DPB1*957:01, DPB1*958:01, DPB1*959:01N, DPB1*95:

01, DPB1*960:01N, DPB1*961:01, DPB1*962:01, DPB1*963:01, DPB1*964:01, DPB1*965:01:01:01, DPB1*965:01:01:02, DPB1*96:01, DPB1*97:01, DPB1*98:01, DPB1*99:01, and any combination thereof.

II.D.2. HLA-DQ Class II Molecules

In some aspects, the alpha chain is an HLA-DQ alpha chain. Any HLA-DQ alpha chain allele known in the art can be used in the compositions and methods disclosed herein. In some aspects, the alpha chain is selected from an HLA-DQA1*01, HLA-DQA1*02, HLA-DQA1*03, HLA-DQA1*04, HLA-DQA1*05, and HLA-DQA1*06 allele. In some aspects, the alpha chain is an HLA-DQA1 allele selected from *01:01:01:01, *01:01:01:02, *01:01:01:03, *01:01:01:05, *01:01:01:06, *01:01:02, *01:01:03, *01:01:04, *01:01:05, *01:02:01:01, *01:02:01:02, *01:02:01:03, *01:02:01:04, *01:02:01:05, *01:02:01:06, *01:02:01:07, *01:02:01:08, *01:02:01:09, *01:02:01:10, *01:02:01:11, *01:02:01:12, *01:02:02:01, *01:02:02:02, *01:02:02:03, *01:02:02:04, *01:02:03, *01:02:04, *01:03:01:01, *01:03:01:02, *01:03:01:03, *01:03:01:04, *01:03:01:05, *01:03:01:06, *01:03:01:07, *01:03:01:08, *01:03:01:09, *01:04:01:01, *01:04:01:02, *01:04:01:03, *01:04:01:04, *01:04:02, *01:05:01, *01:05:02, *01:06, *01:07Q, *01:08, *01:09, *01:10, *01:11, *01:12, *01:13, *01:14, *01:15N, *01:16N, *01:17, *01:18, *01:19, *01:20, *01:21, *01:22, *01:23, *01:24, *01:25, *01:26, *02:01:01:01, *02:01:01:02, *02:01:02, *02:02N, *02:03, *03:01:01, *03:01:03, *03:02:01:01, *03:02:01:02, *03:03:01:01, *03:03:01:02, *03:03:01:03, *03:03:01:04, *03:03:01:05, *03:03:01:06, *03:03:01:07, *03:03:02, *03:04, *03:05, *03:06, *03:07, *04:01:01:01, *04:01:01:02, *04:01:01:03, *04:01:01:04, *04:01:01:05, *04:01:01:06, *04:01:01:07, *04:01:01:08, *04:01:02:01, *04:01:02:02, *04:01:03, *04:02, *04:03N, *04:04, *04:05, *05:01:01:01, *05:01:01:02, *05:01:01:03, *05:01:01:04, *05:01:02, *05:01:04, *05:01:05, *05:01:06, *05:02, *05:03:01:01, *05:03:01:02, *05:04, *05:05:01:01, *05:05:01:02, *05:05:01:03, *05:05:01:04, *05:05:01:05, *05:05:01:06, *05:05:01:07, *05:05:01:08, *05:05:01:09, *05:05:01:10, *05:05:01:11, *05:05:01:12, *05:05:01:13, *05:05:01:14, *05:05:01:15, *05:05:01:16, *05:05:01:17, *05:05:01:18, *05:05:01:19, *05:05:01:20, *05:06:01:01, *05:06:01:02, *05:07, *05:08, *05:09, *05:10, *05:11, *05:12, *05:13, *05:14, *05:15N, *06:01:01:01, *06:01:01:02, *06:01:01:03, *06:01:01:04, *06:01:02, *06:02, and any combination thereof.

In some aspects, the beta chain is an HLA-DQ beta chain. Any HLA-DQ beta chain allele known in the art can be used in the compositions and methods disclosed herein. In some aspects the beta chain is selected from an HLA-DQB1*02, HLA-DQB1*03, HLA-DQB1*04, HLA-DQB1*05, and HLA-DQB1*06 allele.

In certain aspects, the DQ beta chain comprises an allele selected from DQB1*02:01:01, DQB1*02:01:02, DQB1*02:01:03, DQB1*02:01:04, DQB1*02:01:05, DQB1*02:01:06, DQB1*02:01:07, DQB1*02:01:08, DQB1*02:01:09, DQB1*02:01:10, DQB1*02:01:11, DQB1*02:01:12, DQB1*02:01:13, DQB1*02:01:14, DQB1*02:01:15, DQB1*02:01:16, DQB1*02:01:17, DQB1*02:01:18, DQB1*02:01:19, DQB1*02:01:20, DQB1*02:01:21, DQB1*02:01:22, DQB1*02:01:23, DQB1*02:01:24, DQB1*02:01:25, DQB1*02:01:26, DQB1*02:01:27, DQB1*02:01:28, DQB1*02:01:29, DQB1*02:01:30, DQB1*02:01:31, DQB1*02:02:01:01, DQB1*02:02:01:02, DQB1*02:02:01:03, DQB1*02:02:01:04, DQB1*02:02:02, DQB1*02:02:03, DQB1*02:02:04, DQB1*02:02:05, DQB1*02:02:06, DQB1*02:02:07, DQB1*02:02:08, DQB1*02:02:09, DQB1*02:03:01, DQB1*02:03:02, DQB1*02:04, DQB1*02:05, DQB1*02:06, DQB1*02:07:01, DQB1*02:07:02, DQB1*02:08, DQB1*02:09, DQB1*02:10, DQB1*02:100, DQB1*02:101, DQB1*02:102, DQB1*02:103, DQB1*02:104, DQB1*02:105, DQB1*02:106, DQB1*02:107, DQB1*02:108, DQB1*02:109, DQB1*02:11, DQB1*02:110, DQB1*02:111, DQB1*02:112, DQB1*02:113, DQB1*02:114, DQB1*02:115, DQB1*02:116, DQB1*02:117, DQB1*02:118, DQB1*02:119, DQB1*02:12, DQB1*02:120, DQB1*02:121, DQB1*02:122, DQB1*02:123, DQB1*02:124, DQB1*02:125, DQB1*02:126, DQB1*02:127, DQB1*02:128, DQB1*02:129N, DQB1*02:13, DQB1*02:130, DQB1*02:131, DQB1*02:132N, DQB1*02:133, DQB1*02:134N, DQB1*02:135, DQB1*02:136, DQB1*02:137, DQB1*02:138, DQB1*02:139, DQB1*02:140, DQB1*02:141, DQB1*02:142, DQB1*02:14:01, DQB1*02:14:02, DQB1*02:15, DQB1*02:16, DQB1*02:17, DQB1*02:18N, DQB1*02:19, DQB1*02:20N, DQB1*02:21, DQB1*02:22, DQB1*02:23, DQB1*02:24, DQB1*02:25, DQB1*02:26, DQB1*02:27, DQB1*02:28, DQB1*02:29, DQB1*02:30, DQB1*02:31, DQB1*02:32, DQB1*02:33, DQB1*02:34, DQB1*02:35, DQB1*02:36, DQB1*02:37, DQB1*02:38, DQB1*02:39, DQB1*02:40, DQB1*02:41, DQB1*02:42, DQB1*02:43, DQB1*02:44, DQB1*02:45, DQB1*02:46, DQB1*02:47, DQB1*02:48, DQB1*02:49, DQB1*02:50, DQB1*02:51, DQB1*02:52, DQB1*02:53Q, DQB1*02:54, DQB1*02:55, DQB1*02:56, DQB1*02:57, DQB1*02:58N, DQB1*02:59, DQB1*02:60, DQB1*02:61, DQB1*02:62, DQB1*02:63, DQB1*02:64, DQB1*02:65, DQB1*02:66, DQB1*02:67NX, DQB1*02:68, DQB1*02:69, DQB1*02:70, DQB1*02:71, DQB1*02:72, DQB1*02:73, DQB1*02:74, DQB1*02:75, DQB1*02:76, DQB1*02:77, DQB1*02:78, DQB1*02:79, DQB1*02:80, DQB1*02:81, DQB1*02:82, DQB1*02:83, DQB1*02:84, DQB1*02:85, DQB1*02:86, DQB1*02:87, DQB1*02:88, DQB1*02:89:01, DQB1*02:89:02, DQB1*02:90, DQB1*02:91, DQB1*02:92, DQB1*02:93, DQB1*02:94, DQB1*02:95, DQB1*02:96N, DQB1*02:97, DQB1*02:98, DQB1*02:99, DQB1*03:01:01, DQB1*03:01:01:02, DQB1*03:01:01:03, DQB1*03:01:01:04, DQB1*03:01:01:05, DQB1*03:01:01:06, DQB1*03:01:01:07, DQB1*03:01:01:08, DQB1*03:01:01:09, DQB1*03:01:01:10, DQB1*03:01:01:11, DQB1*03:01:01:12, DQB1*03:01:01:14, DQB1*03:01:01:15, DQB1*03:01:01:16, DQB1*03:01:01:17, DQB1*03:01:01:18, DQB1*03:01:01:19, DQB1*03:01:01:20, DQB1*03:01:02, DQB1*03:01:03, DQB1*03:01:04, DQB1*03:01:05, DQB1*03:01:06, DQB1*03:01:07, DQB1*03:01:08, DQB1*03:01:09, DQB1*03:01:10, DQB1*03:01:11, DQB1*03:01:12, DQB1*03:01:13, DQB1*03:01:14, DQB1*03:01:15, DQB1*03:01:16, DQB1*03:01:17, DQB1*03:01:18, DQB1*03:01:19, DQB1*03:01:20, DQB1*03:01:21, DQB1*03:01:22, DQB1*03:01:23, DQB1*03:01:24, DQB1*03:01:25, DQB1*03:01:26, DQB1*03:01:27, DQB1*03:01:28, DQB1*03:01:29, DQB1*03:01:30, DQB1*03:01:31, DQB1*03:01:32, DQB1*03:01:33, DQB1*03:01:34, DQB1*03:01:35, DQB1*03:01:36, DQB1*03:01:37, DQB1*03:01:38, DQB1*03:01:39, DQB1*03:01:40, DQB1*03:01:41, DQB1*03:01:42, DQB1*03:01:43, DQB1*03:01:44, DQB1*03:01:45, DQB1*03:01:46, DQB1*03:02:01:01, DQB1*03:02:01:02, DQB1*03:02:01:03, DQB1*03:02:01:04, DQB1*03:02:01:05, DQB1*03:02:01:06, DQB1*03:02:01:07, DQB1*03:02:01:08, DQB1*03:02:02, DQB1*03:02:03, DQB1*03:02:04, DQB1*03:02:05, DQB1*03:02:06, DQB1*03:02:07, DQB1*03:02:08, DQB1*03:02:09, DQB1*03:02:10, DQB1*03:02:11, DQB1*03:02:12, DQB1*03:02:13, DQB1*03:02:14, DQB1*03:02:15, DQB1*03:02:16, DQB1*03:02:17, DQB1*03:02:18, DQB1*03:02:19, DQB1*03:02:20, DQB1*03:02:21, DQB1*03:02:22, DQB1*03:02:23, DQB1*03:02:24, DQB1*03:02:25, DQB1*03:02:26, DQB1*03:02:27, DQB1*03:02:28, DQB1*03:02:29, DQB1*03:02:30, DQB1*03:03:02:01, DQB1*03:03:02:02, DQB1*03:03:02:03, DQB1*03:03:02:04, DQB1*03:03:02:05, DQB1*03:03:03, DQB1*03:03:04, DQB1*03:03:05, DQB1*03:03:06, DQB1*03:03:07, DQB1*03:03:08, DQB1*03:03:09, DQB1*03:03:10, DQB1*03:03:11, DQB1*03:03:12, DQB1*03:03:13, DQB1*03:03:14, DQB1*03:03:15, DQB1*03:03:16, DQB1*03:03:17, DQB1*03:03:18, DQB1*03:03:19, DQB1*03:03:20, DQB1*03:03:21, DQB1*03:04:01, DQB1*03:04:02, DQB1*03:04:03, DQB1*03:04:04, DQB1*03:05:01, DQB1*03:05:02, DQB1*03:05:03, DQB1*03:05:04, DQB1*03:06, DQB1*03:07, DQB1*03:08, DQB1*03:09, DQB1*03:100, DQB1*03:101, DQB1*03:102, DQB1*03:103, DQB1*03:104, DQB1*03:105, DQB1*03:106, DQB1*03:107, DQB1*03:108, DQB1*03:109, DQB1*03:10:01, DQB1*03:10:02:01, DQB1*03:10:02:02, DQB1*03:11, DQB1*03:110, DQB1*03:111, DQB1*03:112, DQB1*03:113, DQB1*03:114, DQB1*03:115, DQB1*03:116, DQB1*03:117, DQB1*03:118N, DQB1*03:119, DQB1*03:12, DQB1*03:120, DQB1*03:121, DQB1*03:122, DQB1*03:123, DQB1*03:124, DQB1*03:125, DQB1*03:126, DQB1*03:127, DQB1*03:128, DQB1*03:129, DQB1*03:13, DQB1*03:130, DQB1*03:131, DQB1*03:132, DQB1*03:133, DQB1*03:134, DQB1*03:135, DQB1*03:136, DQB1*03:137, DQB1*03:138, DQB1*03:139, DQB1*03:140, DQB1*03:141, DQB1*03:142, DQB1*03:143, DQB1*03:144, DQB1*03:145, DQB1*03:146, DQB1*03:147, DQB1*03:148, DQB1*03:149, DQB1*03:14:01, DQB1*03:14:02, DQB1*03:15, DQB1*03:150, DQB1*03:151, DQB1*03:152, DQB1*03:153, DQB1*03:154, DQB1*03:155, DQB1*03:156, DQB1*03:157, DQB1*03:158, DQB1*03:159, DQB1*03:16, DQB1*03:160, DQB1*03:161, DQB1*03:162, DQB1*03:163, DQB1*03:164, DQB1*03:165, DQB1*03:166, DQB1*03:167, DQB1*03:168, DQB1*03:169, DQB1*03:170, DQB1*03:171, DQB1*03:172, DQB1*03:173, DQB1*03:174, DQB1*03:175, DQB1*03:176, DQB1*03:177, DQB1*03:178, DQB1*03:179, DQB1*03:17:01, DQB1*03:17:02, DQB1*03:18, DQB1*03:180, DQB1*03:181, DQB1*03:182, DQB1*03:183, DQB1*03:184, DQB1*03:185, DQB1*03:186, DQB1*03:187, DQB1*03:188, DQB1*03:189, DQB1*03:190, DQB1*03:191, DQB1*03:192, DQB1*03:193, DQB1*03:194, DQB1*03:195, DQB1*03:196, DQB1*03:197Q, DQB1*03:198:01, DQB1*03:198:02, DQB1*03:199, DQB1*03:19:01, DQB1*03:19:02, DQB1*03:19:03, DQB1*03:19:04, DQB1*03:20, DQB1*03:200, DQB1*03:201, DQB1*03:202, DQB1*03:203, DQB1*03:204, DQB1*03:205, DQB1*03:206, DQB1*03:207, DQB1*03:208, DQB1*03:209, DQB1*03:21, DQB1*03:210, DQB1*03:211, DQB1*03:212, DQB1*03:213NX, DQB1*03:214, DQB1*03:215, DQB1*03:216, DQB1*03:217, DQB1*03:218, DQB1*03:219, DQB1*03:220, DQB1*03:221, DQB1*03:222, DQB1*03:223, DQB1*03:224, DQB1*03:225, DQB1*03:226, DQB1*03:227, DQB1*03:228, DQB1*03:229, DQB1*03:22:01, DQB1*03:22:02, DQB1*03:230, DQB1*03:231, DQB1*03:232, DQB1*03:233, DQB1*03:234, DQB1*03:235, DQB1*03:236, DQB1*03:237N, DQB1*03:238, DQB1*03:239, DQB1*03:23:01, DQB1*03:23:02, DQB1*03:23:03, DQB1*03:24, DQB1*03:240, DQB1*03:

241, DQB1*03:242, DQB1*03:243, DQB1*03:244, DQB1*03:245, DQB1*03:246, DQB1*03:247, DQB1*03:248, DQB1*03:249, DQB1*03:250, DQB1*03:251, DQB1*03:252, DQB1*03:253, DQB1*03:254, DQB1*03:255, DQB1*03:256, DQB1*03:257, DQB1*03:258, DQB1*03:259, DQB1*03:25:01, DQB1*03:25:02, DQB1*03:26, DQB1*03:260, DQB1*03:261, DQB1*03:262, DQB1*03:263, DQB1*03:264, DQB1*03:265, DQB1*03:266, DQB1*03:267, DQB1*03:268, DQB1*03:269N, DQB1*03:27, DQB1*03:270, DQB1*03:271, DQB1*03:272, DQB1*03:273, DQB1*03:274, DQB1*03:275, DQB1*03:277, DQB1*03:278, DQB1*03:279, DQB1*03:28, DQB1*03:280, DQB1*03:281, DQB1*03:282N, DQB1*03:283, DQB1*03:284, DQB1*03:285, DQB1*03:286, DQB1*03:287, DQB1*03:288, DQB1*03:289, DQB1*03:29, DQB1*03:290, DQB1*03:291, DQB1*03:292, DQB1*03:293, DQB1*03:294, DQB1*03:295, DQB1*03:296, DQB1*03:297, DQB1*03:298, DQB1*03:299, DQB1*03:30, DQB1*03:300, DQB1*03:301, DQB1*03:302, DQB1*03:303N, DQB1*03:304, DQB1*03:305, DQB1*03:306, DQB1*03:307, DQB1*03:308, DQB1*03:309, DQB1*03:31, DQB1*03:310N, DQB1*03:311, DQB1*03:312, DQB1*03:313, DQB1*03:314, DQB1*03:315, DQB1*03:316, DQB1*03:317:01, DQB1*03:317:02, DQB1*03:318, DQB1*03:319, DQB1*03:32, DQB1*03:320, DQB1*03:321, DQB1*03:322, DQB1*03:323, DQB1*03:324, DQB1*03:326, DQB1*03:327, DQB1*03:328, DQB1*03:329, DQB1*03:33, DQB1*03:330, DQB1*03:331, DQB1*03:332, DQB1*03:333, DQB1*03:334N4bp, DQB1*03:335, DQB1*03:336, DQB1*03:337, DQB1*03:338N, DQB1*03:339N, DQB1*03:34, DQB1*03:340N, DQB1*03:341, DQB1*03:342, DQB1*03:343, DQB1*03:344, DQB1*03:345, DQB1*03:346, DQB1*03:347, DQB1*03:348, DQB1*03:349, DQB1*03:35, DQB1*03:350, DQB1*03:351, DQB1*03:352, DQB1*03:353, DQB1*03:354N, DQB1*03:355, DQB1*03:356NX, DQB1*03:357N, DQB1*03:358N, DQB1*03:36, DQB1*03:37, DQB1*03:38:01, DQB1*03:38:02, DQB1*03:39, DQB1*03:40, DQB1*03:41, DQB1*03:42, DQB1*03:43, DQB1*03:44, DQB1*03:45, DQB1*03:46, DQB1*03:47, DQB1*03:48, DQB1*03:49, DQB1*03:50, DQB1*03:51, DQB1*03:52, DQB1*03:53, DQB1*03:54, DQB1*03:55, DQB1*03:56, DQB1*03:57, DQB1*03:58, DQB1*03:59, DQB1*03:60, DQB1*03:61, DQB1*03:62, DQB1*03:63, DQB1*03:64, DQB1*03:65, DQB1*03:66N, DQB1*03:67, DQB1*03:68, DQB1*03:69, DQB1*03:70, DQB1*03:71, DQB1*03:72, DQB1*03:73, DQB1*03:74, DQB1*03:75, DQB1*03:76, DQB1*03:77, DQB1*03:78, DQB1*03:79, DQB1*03:80, DQB1*03:81, DQB1*03:82, DQB1*03:83, DQB1*03:84N, DQB1*03:85, DQB1*03:86, DQB1*03:87, DQB1*03:88, DQB1*03:89, DQB1*03:90N, DQB1*03:91Q, DQB1*03:92, DQB1*03:93, DQB1*03:94, DQB1*03:95N, DQB1*03:96, DQB1*03:97, DQB1*03:98, DQB1*03:99Q, DQB1*04:01:01:01, DQB1*04:01:01:02, DQB1*04:01:02, DQB1*04:01:03, DQB1*04:01:04, DQB1*04:01:05, DQB1*04:02:01:01, DQB1*04:02:01:04, DQB1*04:02:01:05, DQB1*04:02:01:06, DQB1*04:02:01:07, DQB1*04:02:01:08, DQB1*04:02:01:09, DQB1*04:02:01:10, DQB1*04:02:02, DQB1*04:02:03, DQB1*04:02:04, DQB1*04:02:05, DQB1*04:02:06, DQB1*04:02:07, DQB1*04:02:08, DQB1*04:02:09, DQB1*04:02:10, DQB1*04:02:11, DQB1*04:02:12, DQB1*04:02:13, DQB1*04:02:14, DQB1*04:02:15, DQB1*04:02:16, DQB1*04:02:17, DQB1*04:02:18, DQB1*04:03:01, DQB1*04:03:02, DQB1*04:03:03, DQB1*04:04, DQB1*04:05, DQB1*04:06, DQB1*04:07, DQB1*04:08,

DQB1*04:09, DQB1*04:10, DQB1*04:11, DQB1*04:12, DQB1*04:13, DQB1*04:14, DQB1*04:15, DQB1*04:16, DQB1*04:17, DQB1*04:18, DQB1*04:19, DQB1*04:20, DQB1*04:21, DQB1*04:22, DQB1*04:23, DQB1*04:24, DQB1*04:25N, DQB1*04:26, DQB1*04:27, DQB1*04:28, DQB1*04:29, DQB1*04:30, DQB1*04:31, DQB1*04:32, DQB1*04:33, DQB1*04:34, DQB1*04:35, DQB1*04:36N, DQB1*04:37, DQB1*04:38, DQB1*04:39, DQB1*04:40, DQB1*04:41N, DQB1*04:42, DQB1*04:43, DQB1*04:44, DQB1*04:45, DQB1*04:46N, DQB1*04:47, DQB1*04:48, DQB1*04:49, DQB1*04:50, DQB1*04:51, DQB1*04:52, DQB1*04:53, DQB1*04:54, DQB1*04:55, DQB1*04:56, DQB1*04:57, DQB1*04:58, DQB1*04:59N, DQB1*04:60, DQB1*04:61, DQB1*04:62, DQB1*05:01:01:01, DQB1*05:01:01:02, DQB1*05:01:01:03, DQB1*05:01:01: 04, DQB1*05:01:01:05, DQB1*05:01:02, DQB1*05:01:03, DQB1*05:01:04, DQB1*05:01:05, DQB1*05:01:06, DQB1*05:01:07, DQB1*05:01:08, DQB1*05:01:09, DQB1*05:01:10, DQB1*05:01:11, DQB1*05:01:12, DQB1*05:01:13, DQB1*05:01:14, DQB1*05:01:15, DQB1*05:01:16, DQB1*05:01:17, DQB1*05:01:18, DQB1*05:01:19, DQB1*05:01:20, DQB1*05:01:21, DQB1*05:01:22, DQB1*05:01:23, DQB1*05:01:24:01, DQB1*05:01:24:02, DQB1*05:01:25, DQB1*05:01:26, DQB1*05:01:27, DQB1*05:01:28, DQB1*05:01:29, DQB1*05:01:30, DQB1*05:01:31, DQB1*05:01:32, DQB1*05:01:33, DQB1*05:01:34, DQB1*05:02:01:01, DQB1*05:02:01:02, DQB1*05:02:01:03, DQB1*05:02:01: 04, DQB1*05:02:01:05, DQB1*05:02:01:06, DQB1*05:02: 02, DQB1*05:02:03, DQB1*05:02:04, DQB1*05:02:05, DQB1*05:02:06, DQB1*05:02:07, DQB1*05:02:08, DQB1*05:02:09, DQB1*05:02:10, DQB1*05:02:11, DQB1*05:02:12, DQB1*05:02:13, DQB1*05:02:14, DQB1*05:02:15, DQB1*05:02:16, DQB1*05:02:17, DQB1*05:02:18, DQB1*05:02:19, DQB1*05:03:01:01, DQB1*05:03:01:02, DQB1*05:03:01:03, DQB1*05:03:02, DQB1*05:03:03, DQB1*05:03:04, DQB1*05:03:05, DQB1*05:03:06, DQB1*05:03:07, DQB1*05:03:08, DQB1*05:03:09, DQB1*05:03:10, DQB1*05:03:11, DQB1*05:03:12, DQB1*05:03:13, DQB1*05:03:14, DQB1*05:03:15, DQB1*05:03:16, DQB1*05:03:17, DQB1*05:03:18, DQB1*05:03:19, DQB1*05:03:20, DQB1*05:04, DQB1*05:05:01, DQB1*05:05:02, DQB1*05:06:01, DQB1*05:06:02, DQB1*05:07, DQB1*05:08, DQB1*05:09, DQB1*05:10, DQB1*05:100, DQB1*05:101, DQB1*05:102, DQB1*05:103, DQB1*05: 104, DQB1*05:105, DQB1*05:106, DQB1*05:107, DQB1*05:108, DQB1*05:109, DQB1*05:110N, DQB1*05:111, DQB1*05:112, DQB1*05:113, DQB1*05: 114, DQB1*05:115, DQB1*05:116, DQB1*05:117, DQB1*05:118, DQB1*05:119, DQB1*05:11:01, DQB1*05:11:02, DQB1*05:12, DQB1*05:120, DQB1*05: 121, DQB1*05:122, DQB1*05:123, DQB1*05:124, DQB1*05:125, DQB1*05:126, DQB1*05:127, DQB1*05: 128N, DQB1*05:129, DQB1*05:13, DQB1*05:130, DQB1*05:131, DQB1*05:132Q, DQB1*05:133, DQB1*05:134, DQB1*05:135, DQB1*05:136, DQB1*05: 137, DQB1*05:138, DQB1*05:139, DQB1*05:14, DQB1*05:140, DQB1*05:141, DQB1*05:142, DQB1*05: 143, DQB1*05:144, DQB1*05:145, DQB1*05:146, DQB1*05:147, DQB1*05:148, DQB1*05:149, DQB1*05: 15, DQB1*05:150, DQB1*05:151, DQB1*05:152, DQB1*05:153, DQB1*05:154, DQB1*05:155, DQB1*05: 156, DQB1*05:157, DQB1*05:158, DQB1*05:159, DQB1*05:16, DQB1*05:160, DQB1*05:161, DQB1*05: 162, DQB1*05:163, DQB1*05:164, DQB1*05:165, DQB1*05:166, DQB1*05:167, DQB1*05:168, DQB1*05: 169, DQB1*05:17, DQB1*05:170, DQB1*05:171, DQB1*05:172, DQB1*05:173, DQB1*05:174, DQB1*05: 175, DQB1*05:176, DQB1*05:177, DQB1*05:178, 181, DQB1*05:182, DQB1*05:183, DQB1*05:184, DQB1*05:185N, DQB1*05:186, DQB1*05:187, DQB1*05:188, DQB1*05:189, DQB1*05:19, DQB1*05: 190, DQB1*05:191, DQB1*05:192, DQB1*05:193, DQB1*05:194, DQB1*05:195, DQB1*05:196, DQB1*05: 197, DQB1*05:198, DQB1*05:199, DQB1*05:20, DQB1*05:200, DQB1*05:201, DQB1*05:202, DQB1*05: 203, DQB1*05:204, DQB1*05:205, DQB1*05:206N, DQB1*05:207, DQB1*05:208N5bp, DQB1*05:209, DQB1*05:21, DQB1*05:210, DQB1*05:211, DQB1*05: 212, DQB1*05:213, DQB1*05:214, DQB1*05:215N, DQB1*05:216, DQB1*05:217, DQB1*05:22, DQB1*05: 23, DQB1*05:24, DQB1*05:25, DQB1*05:26, DQB1*05: 27, DQB1*05:28, DQB1*05:29, DQB1*05:30, DQB1*05: 31, DQB1*05:32, DQB1*05:33, DQB1*05:34, DQB1*05: 35, DQB1*05:36, DQB1*05:37, DQB1*05:38, DQB1*05: 39, DQB1*05:40, DQB1*05:41N, DQB1*05:42, DQB1*05:43:01, DQB1*05:43:02, DQB1*05:44, DQB1*05:45, DQB1*05:46, DQB1*05:47, DQB1*05:48, DQB1*05:49, DQB1*05:50, DQB1*05:51, DQB1*05:52, DQB1*05:53, DQB1*05:54, DQB1*05:55, DQB1*05:56, DQB1*05:57, DQB1*05:58, DQB1*05:59, DQB1*05:60, DQB1*05:61, DQB1*05:62, DQB1*05:63, DQB1*05:64, DQB1*05:65, DQB1*05:66:01, DQB1*05:66:02, DQB1*05:67, DQB1*05:68, DQB1*05:69, DQB1*05:70, DQB1*05:71, DQB1*05:72, DQB1*05:73, DQB1*05:74, DQB1*05:75, DQB1*05:76, DQB1*05:77, DQB1*05:78, DQB1*05:79, DQB1*05:80, DQB1*05:81, DQB1*05:82, DQB1*05:83, DQB1*05:84, DQB1*05:85, DQB1*05:86, DQB1*05:87Q, DQB1*05:88, DQB1*05:89:01, DQB1*05: 89:02, DQB1*05:90N, DQB1*05:91, DQB1*05:92, DQB1*05:93, DQB1*05:94, DQB1*05:95, DQB1*05:96, DQB1*05:97, DQB1*05:98, DQB1*05:99, DQB1*06:01: 01:01, DQB1*06:01:01:02, DQB1*06:01:02, DQB1*06:01: 03, DQB1*06:01:04, DQB1*06:01:05, DQB1*06:01:06, DQB1*06:01:07, DQB1*06:01:08, DQB1*06:01:09, DQB1*06:01:10, DQB1*06:01:11, DQB1*06:01:12, DQB1*06:01:13, DQB1*06:01:14, DQB1*06:01:15, DQB1*06:01:16, DQB1*06:01:17, DQB1*06:01:18, DQB1*06:01:19, DQB1*06:01:20, DQB1*06:01:21, DQB1*06:02:01:01, DQB1*06:02:01:02, DQB1*06:02:01: 03, DQB1*06:02:01:04, DQB1*06:02:02, DQB1*06:02:03, DQB1*06:02:04, DQB1*06:02:05, DQB1*06:02:06, DQB1*06:02:07, DQB1*06:02:08, DQB1*06:02:09, DQB1*06:02:10, DQB1*06:02:11, DQB1*06:02:12, DQB1*06:02:13, DQB1*06:02:14, DQB1*06:02:15, DQB1*06:02:16, DQB1*06:02:17, DQB1*06:02:18, DQB1*06:02:19, DQB1*06:02:20, DQB1*06:02:21, DQB1*06:02:22, DQB1*06:02:23, DQB1*06:02:24, DQB1*06:02:25, DQB1*06:02:26, DQB1*06:02:27, DQB1*06:02:28, DQB1*06:02:29, DQB1*06:02:30, DQB1*06:02:31, DQB1*06:02:32, DQB1*06:02:33, DQB1*06:02:34, DQB1*06:02:35, DQB1*06:02:36, DQB1*06:02:37, DQB1*06:02:38, DQB1*06:03:01:01, DQB1*06:03:01:02, DQB1*06:03:01:03, DQB1*06:03:02, DQB1*06:03:03, DQB1*06:03:04, DQB1*06:03:05, DQB1*06:03:06, DQB1*06:03:07, DQB1*06:03:08, DQB1*06:03:09, DQB1*06:03:10, DQB1*06:03:11, DQB1*06:03:12, DQB1*06:03:13, DQB1*06:03:14, DQB1*06:03:15, DQB1*06:03:16, DQB1*06:03:17, DQB1*06:03:18, DQB1*06:03:19, DQB1*06:03:20, DQB1*06:03:21, DQB1*06:03:22, DQB1*06:03:23, DQB1*06:03:24, DQB1*06:03:25, DQB1*06:03:26,

DQB1*06:03:27, DQB1*06:03:28, DQB1*06:03:29, DQB1*06:03:30, DQB1*06:03:31, DQB1*06:03:32, DQB1*06:03:33, DQB1*06:03:34, DQB1*06:03:35, DQB1*06:04:01, DQB1*06:04:02, DQB1*06:04:03, DQB1*06:04:04, DQB1*06:04:05, DQB1*06:04:06, DQB1*06:04:07, DQB1*06:04:08, DQB1*06:04:09, DQB1*06:04:10, DQB1*06:04:11, DQB1*06:04:12, DQB1*06:05:01, DQB1*06:05:02, DQB1*06:06, DQB1*06:07:01, DQB1*06:07:02, DQB1*06:08:01, DQB1*06:08:02, DQB1*06:08:03, DQB1*06:09:01:01, DQB1*06:09:01:02, DQB1*06:09:02, DQB1*06:09:03, DQB1*06:09:04, DQB1*06:09:05, DQB1*06:09:06, DQB1*06:09:07, DQB1*06:09:08, DQB1*06:09:09, DQB1*06:09:10, DQB1*06:10, DQB1*06:100, DQB1*06:101, DQB1*06:102N, DQB1*06:103, DQB1*06:104, DQB1*06:105, DQB1*06:106, DQB1*06:107, DQB1*06:108, DQB1*06:109, DQB1*06:110, DQB1*06:111, DQB1*06:112N, DQB1*06:113, DQB1*06:114, DQB1*06:115, DQB1*06:116, DQB1*06:117, DQB1*06:118:01, DQB1*06:118:02, DQB1*06:118:03, DQB1*06:119, DQB1*06:11:01, DQB1*06:1:02, DQB1*06:11:03, DQB1*06:11:04, DQB1*06:12, DQB1*06:120, DQB1*06:121, DQB1*06:122, DQB1*06:123, DQB1*06:124, DQB1*06:125, DQB1*06:126, DQB1*06:127, DQB1*06:128, DQB1*06:129, DQB1*06:130, DQB1*06:131, DQB1*06:132, DQB1*06:133, DQB1*06:134, DQB1*06:135, DQB1*06:136, DQB1*06:137, DQB1*06:138, DQB1*06:139, DQB1*06:13:01, DQB1*06:13:02, DQB1*06:13:03, DQB1*06:140, DQB1*06:141, DQB1*06:142, DQB1*06:143, DQB1*06:144N, DQB1*06:145, DQB1*06:146:01, DQB1*06:146:02, DQB1*06:147, DQB1*06:148, DQB1*06:149, DQB1*06:14:01, DQB1*06:14:02, DQB1*06:14:03, DQB1*06:150, DQB1*06:151, DQB1*06:152, DQB1*06:153:01, DQB1*06:153:02, DQB1*06:154, DQB1*06:155, DQB1*06:156, DQB1*06:157, DQB1*06:158N, DQB1*06:159, DQB1*06:15:01, DQB1*06:15:02, DQB1*06:16, DQB1*06:160, DQB1*06:161, DQB1*06:162, DQB1*06:163, DQB1*06:164, DQB1*06:165, DQB1*06:166, DQB1*06:167, DQB1*06:168, DQB1*06:169, DQB1*06:17, DQB1*06:170, DQB1*06:171, DQB1*06:172, DQB1*06:173, DQB1*06:174, DQB1*06:175, DQB1*06:176, DQB1*06:177, DQB1*06:178, DQB1*06:179N, DQB1*06:180, DQB1*06:181, DQB1*06:182, DQB1*06:183, DQB1*06:184, DQB1*06:185, DQB1*06:186, DQB1*06:187, DQB1*06:188, DQB1*06:189, DQB1*06:18:01, DQB1*06:18:02, DQB1*06:190:01, DQB1*06:190:02, DQB1*06:191, DQB1*06:192, DQB1*06:193N, DQB1*06:194, DQB1*06:195, DQB1*06:196, DQB1*06:197, DQB1*06:198, DQB1*06:199, DQB1*06:19:01, DQB1*06:19:02, DQB1*06:20, DQB1*06:200, DQB1*06:201, DQB1*06:202, DQB1*06:203, DQB1*06:204, DQB1*06:205, DQB1*06:206:01, DQB1*06:206:02, DQB1*06:207, DQB1*06:208, DQB1*06:209, DQB1*06:21, DQB1*06:210, DQB1*06:211, DQB1*06:212, DQB1*06:213, DQB1*06:214, DQB1*06:215, DQB1*06:216N, DQB1*06:217, DQB1*06:218, DQB1*06:219, DQB1*06:221, DQB1*06:222, DQB1*06:223, DQB1*06:224, DQB1*06:225, DQB1*06:226, DQB1*06:227, DQB1*06:228, DQB1*06:229, DQB1*06:22:01, DQB1*06:22:02, DQB1*06:22:03, DQB1*06:23, DQB1*06:230, DQB1*06:231, DQB1*06:232, DQB1*06:233, DQB1*06:234, DQB1*06:235, DQB1*06:236, DQB1*06:237, DQB1*06:238, DQB1*06:239, DQB1*06:24, DQB1*06:240, DQB1*06:241, DQB1*06:242, DQB1*06:243, DQB1*06:244, DQB1*06:245, DQB1*06:246, DQB1*06:247,

DQB1*06:248, DQB1*06:249, DQB1*06:25, DQB1*06:250, DQB1*06:251, DQB1*06:252N, DQB1*06:253, DQB1*06:254, DQB1*06:255, DQB1*06:256, DQB1*06:257, DQB1*06:258, DQB1*06:259, DQB1*06:260, DQB1*06:261, DQB1*06:262, DQB1*06:263, DQB1*06:264, DQB1*06:265, DQB1*06:266, DQB1*06:267, DQB1*06:268, DQB1*06:269, DQB1*06:26N, DQB1*06:270:01, DQB1*06:270:02, DQB1*06:271, DQB1*06:272, DQB1*06:273, DQB1*06:274, DQB1*06:275, DQB1*06:276, DQB1*06:277, DQB1*06:278, DQB1*06:279, DQB1*06:27:01, DQB1*06:27:02, DQB1*06:28, DQB1*06:280, DQB1*06:281, DQB1*06:282, DQB1*06:283, DQB1*06:284, DQB1*06:285, DQB1*06:286, DQB1*06:287, DQB1*06:288, DQB1*06:289, DQB1*06:29, DQB1*06:290, DQB1*06:291, DQB1*06:292, DQB1*06:293, DQB1*06:294, DQB1*06:295, DQB1*06:296, DQB1*06:297, DQB1*06:298, DQB1*06:299, DQB1*06:30, DQB1*06:300, DQB1*06:301, DQB1*06:302, DQB1*06:303N, DQB1*06:304N, DQB1*06:305, DQB1*06:306N, DQB1*06:307, DQB1*06:308N, DQB1*06:309, DQB1*06:31, DQB1*06:310, DQB1*06:311, DQB1*06:312, DQB1*06:313, DQB1*06:314, DQB1*06:315, DQB1*06:316, DQB1*06:317N, DQB1*06:318, DQB1*06:319, DQB1*06:320, DQB1*06:321, DQB1*06:322, DQB1*06:323, DQB1*06:324, DQB1*06:325, DQB1*06:326, DQB1*06:32:01, DQB1*06:32:02, DQB1*06:33, DQB1*06:34, DQB1*06:35, DQB1*06:36, DQB1*06:37, DQB1*06:38, DQB1*06:39, DQB1*06:40, DQB1*06:41, DQB1*06:42, DQB1*06:43, DQB1*06:44, DQB1*06:45, DQB1*06:46, DQB1*06:47, DQB1*06:48:01, DQB1*06:48:02, DQB1*06:49, DQB1*06:50, DQB1*06:51:01, DQB1*06:51:02, DQB1*06:52, DQB1*06:53:01, DQB1*06:53:02, DQB1*06:54N, DQB1*06:55, DQB1*06:56, DQB1*06:57, DQB1*06:58, DQB1*06:59, DQB1*06:60, DQB1*06:61, DQB1*06:62, DQB1*06:63, DQB1*06:64, DQB1*06:65, DQB1*06:66, DQB1*06:67, DQB1*06:68, DQB1*06:69:01, DQB1*06:69:02, DQB1*06:70, DQB1*06:71, DQB1*06:72, DQB1*06:73, DQB1*06:74, DQB1*06:75NX, DQB1*06:76, DQB1*06:77N, DQB1*06:78, DQB1*06:79:01, DQB1*06:79:02, DQB1*06:80, DQB1*06:81, DQB1*06:82, DQB1*06:83, DQB1*06:84, DQB1*06:85, DQB1*06:86, DQB1*06:87, DQB1*06:88, DQB1*06:89, DQB1*06:90, DQB1*06:91, DQB1*06:92:01, DQB1*06:92:02, DQB1*06:93, DQB1*06:94, DQB1*06:95, DQB1*06:96:01, DQB1*06:96:02, DQB1*06:97, DQB1*06:98, DQB1*06:99:01, DQB1*06:99:02, and any combination thereof.

II.D.3. HLA-DR Class II Molecules

In some aspects, the alpha chain is an HLA-DR alpha chain. Any HLA-DR alpha chain allele known in the art can be used in the compositions and methods disclosed herein. In some aspects, the alpha chain is an HLA-DRA*01 allele. In some aspects, the alpha chain is an HLA-DRA1 allele selected from *01:01:01:01, *01:01:01:02, *01:01:01:03, *01:01:02, *01:02:01, *01:02:02, *01:02:03, and any combination thereof.

In some aspects, the beta chain is an HLA-DR beta chain. Any HLA-DR beta chain allele known in the art can be used in the compositions and methods disclosed herein. In some aspects the beta chain is selected from an HLA-DRB1*01, HLA-DRB1*03, HLA-DRB1*04, HLA-DRB1*07, HLA-DRB1*08, HLA-DRB1*09, HLA-DRB1*10, HLA-DRB1*11, HLA-DRB1*12, HLA-DRB1*13, HLA-DRB1*14, HLA-DRB1*15, and HLA-DRB1*16 allele. In some aspects, the beta chain is a DRB3 allele. In some aspects, the beta chain is a DRB4 allele. In some aspects, the beta chain is a DRB5 allele.

In some aspects the beta chain is selected from DRB1*01: 01:01, DRB1*01:01:02, DRB1*01:01:03, DRB1*01:01:04, DRB1*01:01:05, DRB1*01:01:06, DRB1*01:01:07, DRB1*01:01:08, DRB1*01:01:09, DRB1*01:01:10, DRB1*01:01:11, DRB1*01:01:12, DRB1*01:01:13, DRB1*01:01:14, DRB1*01:01:15, DRB1*01:01:16, DRB1*01:01:17, DRB1*01:01:18, DRB1*01:01:19, DRB1*01:01:20, DRB1*01:01:21, DRB1*01:01:22, DRB1*01:01:23, DRB1*01:01:24, DRB1*01:01:25, DRB1*01:01:26, DRB1*01:01:27, DRB1*01:01:28, DRB1*01:01:29, DRB1*01:01:30, DRB1*01:01:31, DRB1*01:01:32, DRB1*01:01:33, DRB1*01:02:01:01, DRB1*01:02:01:02, DRB1*01:02:02, DRB1*01:02:03, DRB1*01:02:04, DRB1*01:02:05, DRB1*01:02:06, DRB1*01:02:07, DRB1*01:02:08, DRB1*01:02:09, DRB1*01:02:10, DRB1*01:02:11, DRB1*01:02:12, DRB1*01:02:13, DRB1*01:03:01, DRB1*01:03:02, DRB1*01:03:03, DRB1*01:03:04, DRB1*01:04, DRB1*01:05, DRB1*01:06, DRB1*01:07, DRB1*01:08, DRB1*01:09, DRB1*01:10, DRB1*01:100, DRB1*01:11: 01, DRB1*01:11:02, DRB1*01:12, DRB1*01:13, DRB1*01:14, DRB1*01:15, DRB1*01:16, DRB1*01:17, DRB1*01:18:01, DRB1*01:18:02, DRB1*01:19, DRB1*01:20:01, DRB1*01:20:02, DRB1*01:21, DRB1*01:22, DRB1*01:23, DRB1*01:24:01, DRB1*01: 24:02, DRB1*01:25, DRB1*01:26, DRB1*01:27, DRB1*01:28, DRB1*01:29:01, DRB1*01:29:02, DRB1*01:30, DRB1*01:31, DRB1*01:32, DRB1*01:33N, DRB1*01:34, DRB1*01:35, DRB1*01:36, DRB1*01:37, DRB1*01:38, DRB1*01:39N, DRB1*01:40N, DRB1*01: 41, DRB1*01:42, DRB1*01:43, DRB1*01:44:01, DRB1*01:44:02, DRB1*01:45, DRB1*01:46, DRB1*01: 47, DRB1*01:48, DRB1*01:49, DRB1*01:50, DRB1*01: 51, DRB1*01:52N, DRB1*01:53, DRB1*01:54, DRB1*01: 55, DRB1*01:56, DRB1*01:57, DRB1*01:58, DRB1*01: 59, DRB1*01:60, DRB1*01:61, DRB1*01:62N, DRB1*01: 63, DRB1*01:64, DRB1*01:65:01, DRB1*01:65:02, DRB1*01:66, DRB1*01:67, DRB1*01:68N, DRB1*01:69, DRB1*01:70, DRB1*01:71, DRB1*01:72, DRB1*01:73, DRB1*01:74, DRB1*01:75, DRB1*01:76, DRB1*01:77, DRB1*01:78, DRB1*01:79, DRB1*01:80, DRB1*01:81, DRB1*01:82, DRB1*01:83, DRB1*01:84, DRB1*01:85, DRB1*01:86, DRB5*01:87, DRB1*01:88, DRB1*01:89, DRB1*01:90, DRB1*01:91Q, DRB1*01:92, DRB1*01:93, DRB1*01:94, DRB1*01:95, DRB1*01:96, DRB1*01:97, DRB1*01:98, DRB1*01:99, DRB1*03:01:01:01, DRB1*03:01:01:02, DRB1*03:01:01:03, DRB1*03:01:02, DRB1*03:01:03, DRB1*03:01:04, DRB1*03:01:05, DRB1*03:01:06, DRB1*03:01:07, DRB1*03:01:08, DRB1*03:01:09, DRB1*03:01:10, DRB1*03:01:11, DRB1*03:01:12, DRB1*03:01:13, DRB1*03:01:14, DRB1*03:01:15, DRB1*03:01:16, DRB1*03:01:17, DRB1*03:01:18, DRB1*03:01:19, DRB1*03:01:20, DRB1*03:01:21, DRB1*03:01:22, DRB1*03:01:23, DRB1*03:01:24, DRB1*03:01:25, DRB1*03:01:26, DRB1*03:01:27, DRB1*03:01:28, DRB1*03:02:01, DRB1*03:02:02, DRB1*03:02:03, DRB1*03:03, DRB1*03:04:01, DRB1*03:04:02, DRB1*03:05:01, DRB1*03:05:02, DRB1*03:05:03, DRB1*03:06, DRB1*03:07:01, DRB1*03:07:02, DRB1*03:08, DRB1*03:09, DRB1*03:10, DRB1*03:100:01, DRB1*03: 100:02, DRB1*03:101, DRB1*03:102, DRB1*03:103, DRB1*03:104, DRB1*03:105, DRB1*03:106, DRB1*03: 107, DRB1*03:108, DRB1*03:109, DRB1*03:110, DRB1*03:111, DRB1*03:112, DRB1*03:113, DRB1*03: 114, DRB1*03:115, DRB1*03:116, DRB1*03:117, DRB1*03:118, DRB1*03:119, DRB1*03:11:01, DRB1*03: 12, DRB1*03:120, DRB1*03:121, DRB1*03:122, DRB1*03:123, DRB1*03:124, DRB1*03:125, DRB1*03: 126, DRB1*03:127, DRB1*03:128, DRB1*03:129, DRB1*03:130, DRB1*03:131, DRB1*03:132, DRB1*03: 133, DRB1*03:134, DRB1*03:135, DRB1*03:136, DRB1*03:137, DRB1*03:138, DRB1*03:139, DRB1*03: 13:01, DRB1*03:13:02, DRB1*03:14, DRB1*03:140, DRB1*03:141, DRB1*03:142, DRB1*03:143, DRB1*03: 144, DRB1*03:145, DRB1*03:146, DRB1*03:147, DRB1*03:148, DRB1*03:149, DRB1*03:150, DRB1*03: 151, DRB1*03:152, DRB1*03:153, DRB1*03:154, DRB1*03:155, DRB1*03:156N, DRB1*03:157, DRB1*03: 158, DRB1*03:15:01, DRB1*03:15:02, DRB1*03:16, DRB1*03:17, DRB1*03:18, DRB1*03:19, DRB1*03:20, DRB1*03:21, DRB1*03:22, DRB1*03:23, DRB1*03:24, DRB1*03:25:01, DRB1*03:25:02, DRB1*03:26, DRB1*03:27, DRB1*03:28, DRB1*03:29, DRB1*03:30, DRB1*03:31, DRB1*03:32, DRB1*03:33, DRB1*03:34, DRB1*03:35, DRB1*03:36, DRB1*03:37, DRB1*03:38, DRB1*03:39, DRB1*03:40, DRB1*03:41:01, DRB1*03: 41:02, DRB1*03:42, DRB1*03:43, DRB1*03:44, DRB1*03:45, DRB1*03:46, DRB1*03:47, DRB1*03:48, DRB1*03:49, DRB1*03:50, DRB1*03:51, DRB1*03:52, DRB1*03:53, DRB1*03:54, DRB1*03:55, DRB1*03:56, DRB1*03:57, DRB1*03:58, DRB1*03:59, DRB1*03:60, DRB1*03:61, DRB1*03:62, DRB1*03:63, DRB1*03:64, DRB1*03:65, DRB1*03:66, DRB1*03:67N, DRB1*03: 68N, DRB1*03:69, DRB1*03:70, DRB1*03:71:01, DRB1*03:71:02, DRB1*03:72, DRB1*03:73, DRB1*03: 74, DRB1*03:75, DRB1*03:76, DRB1*03:77, DRB1*03: 78, DRB1*03:79, DRB1*03:80, DRB1*03:81, DRB1*03: 82, DRB1*03:83, DRB1*03:84, DRB1*03:85, DRB1*03: 86, DRB1*03:87, DRB1*03:88, DRB1*03:89, DRB1*03: 90, DRB1*03:91, DRB1*03:92, DRB1*03:93, DRB1*03: 94, DRB1*03:95, DRB1*03:96, DRB1*03:97, DRB1*03: 98, DRB1*03:99, DRB1*04:01:01:01, DRB1*04:01:01:02, DRB1*04:01:01:03, DRB1*04:01:02, DRB1*04:01:03, DRB1*04:01:04, DRB1*04:01:05, DRB1*04:01:06, DRB1*04:01:07, DRB1*04:01:08, DRB1*04:01:09, DRB1*04:01:10, DRB1*04:01:11, DRB1*04:01:12, DRB1*04:01:13, DRB1*04:01:14, DRB1*04:01:15, DRB1*04:01:16, DRB1*04:01:17, DRB1*04:01:18, DRB1*04:01:19, DRB1*04:01:20, DRB1*04:01:21, DRB1*04:02:01, DRB1*04:02:02, DRB1*04:02:03, DRB1*04:02:04, DRB1*04:02:05, DRB1*04:02:06, DRB1*04:03:01:01, DRB1*04:03:01:02, DRB1*04:03:02, DRB1*04:03:03, DRB1*04:03:04, DRB1*04:03:05, DRB1*04:03:06, DRB1*04:03:07, DRB1*04:03:08, DRB1*04:03:09, DRB1*04:03:10, DRB1*04:03:11, DRB1*04:03:12, DRB1*04:03:13, DRB1*04:03:14, DRB1*04:03:15, DRB1*04:04:01, DRB1*04:04:02, DRB1*04:04:03, DRB1*04:04:04, DRB1*04:04:05, DRB1*04:04:06, DRB1*04:04:07, DRB1*04:04:08, DRB1*04:04:09, DRB1*04:04:10, DRB1*04:04:11, DRB1*04:04:12, DRB1*04:04:13, DRB1*04:04:14, DRB1*04:04:15, DRB1*04:05:01:01, DRB1*04:05:01:02, DRB1*04:05:01:03, DRB1*04:05:02, DRB1*04:05:03, DRB1*04:05:04, DRB1*04:05:05, DRB1*04:05:06, DRB1*04:05:07, DRB1*04:05:08, DRB1*04:05:09, DRB1*04:05:10, DRB1*04:05:11, DRB1*04:05:13, DRB1*04:05:14, DRB1*04:05:15, DRB1*04:05:16, DRB1*04:05:17, DRB1*04:05:18, DRB1*04:05:19, DRB1*04:05:20, DRB1*04:06:01, DRB1*04:06:02, DRB1*04:06:03, DRB1*04:06:04, DRB1*04:06:05, DRB1*04:06:06, DRB1*04:06:07, DRB1*04:07:01:01, DRB1*04:07:01:02, DRB1*04:07:02, DRB1*04:07:03, DRB1*04:07:04, DRB1*04:07:05, DRB1*04:07:06, DRB1*04:08:01, DRB1*04:08:02, DRB1*04:08:03, DRB1*04:08:04, DRB1*04:09, DRB1*04:100, DRB1*04: 101, DRB1*04:102, DRB1*04:103, DRB1*04:104, DRB1*04:105:01, DRB1*04:105:02, DRB1*04:106, DRB1*04:107, DRB1*04:108, DRB1*04:109, DRB1*04: 10:01, DRB1*04:10:02, DRB1*04:10:03, DRB1*04:110, DRB1*04:111, DRB1*04:112, DRB1*04:113, DRB1*04: 114, DRB1*04:115, DRB1*04:116, DRB1*04:117, DRB1*04:118, DRB1*04:119N, DRB1*04:11:01, DRB1*04:11:02, DRB1*04:11:03, DRB1*04:11:04, DRB1*04:11:05, DRB1*04:12, DRB1*04:120N, DRB1*04:121, DRB1*04:122, DRB1*04:123, DRB1*04: 124, DRB1*04:125, DRB1*04:126, DRB1*04:127, DRB1*04:128, DRB1*04:129, DRB1*04:13, DRB1*04: 130, DRB1*04:131:01, DRB1*04:131:02, DRB1*04:132, DRB1*04:133, DRB1*04:134, DRB1*04:135, DRB1*04: 136, DRB1*04:137, DRB1*04:138, DRB1*04:139, DRB1*04:14, DRB1*04:140, DRB1*04:141, DRB1*04: 142N, DRB1*04:143, DRB1*04:144, DRB1*04:145, DRB1*04:146, DRB1*04:147, DRB1*04:148, DRB1*04: 149, DRB1*04:15, DRB1*04:150, DRB1*04:151, DRB1*04:152, DRB1*04:153, DRB1*04:154, DRB1*04: 155, DRB1*04:156, DRB1*04:157N, DRB1*04:158N, DRB1*04:159, DRB1*04:16, DRB1*04:160, DRB1*04: 161, DRB1*04:162, DRB1*04:163, DRB1*04:164, DRB1*04:165, DRB1*04:166, DRB1*04:167, DRB1*04: 168, DRB1*04:169, DRB1*04:170, DRB1*04:171, DRB1*04:172, DRB1*04:173, DRB1*04:174, DRB1*04: 175, DRB1*04:176, DRB1*04:177, DRB1*04:178N, DRB1*04:179, DRB1*04:17:01, DRB1*04:17:02, DRB1*04:18, DRB1*04:180, DRB1*04:181, DRB1*04: 182, DRB1*04:183, DRB1*04:184, DRB1*04:185, DRB1*04:186N, DRB1*04:187, DRB1*04:188, DRB1*04: 189, DRB1*04:19, DRB1*04:190, DRB1*04:191, DRB1*04:192, DRB1*04:193, DRB1*04:194, DRB1 04:195, DRB1*04:196, DRB1*04:197, DRB1*04:198, DRB1*04:199, DRB1*04:20, DRB1*04:200, DRB1*04: 201, DRB1*04:202, DRB1*04:203, DRB1*04:204, DRB1*04:205, DRB1*04:206, DRB1*04:207, DRB1*04: 208, DRB1*04:209, DRB1*04:21, DRB1*04:210, DRB1*04:211, DRB1*04:212N, DRB1*04:213, DRB1*04: 214N, DRB1*04:215, DRB1*04:216, DRB1*04:217, DRB1*04:218, DRB1*04:219, DRB1*04:22, DRB1*04: 220, DRB1*04:221, DRB1*04:222, DRB1*04:223, DRB1*04:224, DRB1*04:225, DRB1*04:226:01, DRB1*04:226:02, DRB1*04:227, DRB1*04:228, DRB1*04:229, DRB1*04:23, DRB1*04:230, DRB1*04: 231, DRB1*04:232, DRB1*04:233, DRB1*04:234, DRB1*04:235, DRB1*04:236, DRB1*04:237, DRB1*04: 238, DRB1*04:239, DRB1*04:24, DRB1*04:240, DRB1*04:241, DRB1*04:242, DRB1*04:243, DRB1*04: 244, DRB1*04:245, DRB1*04:246, DRB1*04:247N, DRB1*04:248, DRB1*04:249, DRB1*04:25, DRB1*04: 250, DRB1*04:251, DRB1*04:252, DRB1*04:253, DRB1*04:254, DRB1*04:255, DRB1*04:256, DRB1*04: 257, DRB1*04:258, DRB1*04:259, DRB1*04:26, DRB1*04:260, DRB1*04:261, DRB1*04:262, DRB1*04: 263, DRB1*04:264N, DRB1*04:265, DRB1*04:266N, DRB1*04:267N, DRB1*04:268, DRB1*04:269, DRB1*04: 27, DRB1*04:270, DRB1*04:271, DRB1*04:272, DRB1*04:28, DRB1*04:29, DRB1*04:30, DRB1*04:31, DRB1*04:32, DRB1*04:33, DRB1*04:34, DRB1*04:35, DRB1*04:36, DRB1*04:37, DRB1*04:38, DRB1*04:39, DRB1*04:40, DRB1*04:41, DRB1*04:42, DRB1*04:43, DRB1*04:44:01, DRB1*04:44:02, DRB1*04:45, DRB1*04:46, DRB1*04:47, DRB1*04:48, DRB1*04:49, DRB1*04:50, DRB1*04:51, DRB1*04:52, DRB1*04:53: 01, DRB1*04:53:02, DRB1*04:54, DRB1*04:55, DRB1*04:56:01, DRB1*04:56:02, DRB1*04:57, DRB1*04:58, DRB1*04:59, DRB1*04:60, DRB1*04:61, DRB1*04:62, DRB1*04:63, DRB1*04:64, DRB1*04:65, DRB1*04:66, DRB1*04:67, DRB1*04:68, DRB1*04:69, DRB1*04:70, DRB1*04:71, DRB1*04:72:01, DRB1*04: 72:02, DRB1*04:73:01, DRB1*04:73:02, DRB1*04:74, DRB1*04:75, DRB1*04:76, DRB1*04:77, DRB1*04:78, DRB1*04:79, DRB1*04:80, DRB1*04:81N, DRB1*04:82, DRB1*04:83, DRB1*04:84, DRB1*04:85, DRB1*04:86, DRB1*04:87, DRB1*04:88, DRB1*04:89, DRB1*04:90, DRB1*04:91, DRB1*04:92, DRB1*04:93, DRB1*04:94: 01N, DRB1*04:95:01, DRB1*04:95:02, DRB1*04:96, DRB1*04:97, DRB1*04:98:01, DRB1*04:98:02, DRB1*04:99, DRB1*07:01:01:01, DRB1*07:01:01:02, DRB1*07:01:01:03, DRB1*07:01:01:04, DRB1*07:01:02, DRB1*07:01:03, DRB1*07:01:04, DRB1*07:01:05, DRB1*07:01:06, DRB1*07:01:07, DRB1*07:01:08, DRB1*07:01:09, DRB1*07:01:10, DRB1*07:01:11, DRB1*07:01:12, DRB1*07:01:13, DRB1*07:01:14, DRB1*07:01:15, DRB1*07:01:16 DRB1*07:01:17 DRB1*07:01:18, DRB1*07:01:19, DRB1*07:01:20, DRB1*07:01:21, DRB1*07:01:22, DRB1*07:03, DRB1*07:04, DRB1*07:05, DRB1*07:06, DRB1*07:07, DRB1*07:08, DRB1*07:09, DRB1*07:100, DRB1*07: 101N, DRB1*07:10N, DRB1*07:11, DRB1*07:12, DRB1*07:13, DRB1*07:14, DRB1*07:15, DRB1*07:16, DRB1*07:17, DRB1*07:18, DRB1*07:19, DRB1*07:20, DRB1*07:21, DRB1*07:22, DRB1*07:23, DRB1*07:24, DRB1*07:25, DRB1*07:26N, DRB1*07:27, DRB1*07:28, DRB1*07:29, DRB1*07:30, DRB1*07:31, DRB1*07:32, DRB1*07:33, DRB1*07:34, DRB1*07:35, DRB1*07:36, DRB1*07:37, DRB1*07:38, DRB1*07:39, DRB1*07:40, DRB1*07:41, DRB1*07:42, DRB1*07:43, DRB1*07:44, DRB1*07:45, DRB1*07:46, DRB1*07:47, DRB1*07:48, DRB1*07:49, DRB1*07:50, DRB1*07:51, DRB1*07:52, DRB1*07:53, DRB1*07:54, DRB1*07:55, DRB1*07:56, DRB1*07:57, DRB1*07:58N, DRB1*07:59, DRB1*07:60, DRB1*07:61, DRB1*07:62, DRB1*07:63, DRB1*07:64, DRB1*07:65, DRB1*07:66, DRB1*07:67, DRB1*07:68N, DRB1*07:69, DRB1*07:70, DRB1*07:71, DRB1*07:72, DRB1*07:73, DRB1*07:74, DRB1*07:75, DRB1*07:76, DRB1*07:77, DRB1*07:78, DRB1*07:79, DRB1*07:80, DRB1*07:81, DRB1*07:82, DRB1*07:83, DRB1*07:84, DRB1*07:85, DRB1*07:86, DRB1*07:87N, DRB1*07:88, DRB1*07:89, DRB1*07:90, DRB1*07:91, DRB1*07:92, DRB1*07:93, DRB1*07:94, DRB1*07:95, DRB1*07:96, DRB1*07:97, DRB1*07:98, DRB1*07:99, DRB1*08:01: 01, DRB1*08:01:02, DRB1*08:01:04, DRB1*08:01:05, DRB1*08:01:06, DRB1*08:01:07, DRB1*08:02:01:01, DRB1*08:02:01:02, DRB1*08:02:02, DRB1*08:02:03, DRB1*08:02:04, DRB1*08:03:02:01, DRB1*08:03:02:02, DRB1*08:03:03, DRB1*08:03:04, DRB1*08:03:05, DRB1*08:03:06, DRB1*08:03:07, DRB1*08:03:08, DRB1*08:03:09, DRB1*08:04:01, DRB1*08:04:02, DRB1*08:04:03, DRB1*08:04:04, DRB1*08:04:05, DRB1*08:04:06, DRB1*08:04:07, DRB1*08:05, DRB1*08:06, DRB1*08:07, DRB1*08:08, DRB1*08:09, DRB1*08:10, DRB1*08:11, DRB1*08:12, DRB1*08:13, DRB1*08:14, DRB1*08:15, DRB1*08:16, DRB1*08:17, DRB1*08:18, DRB1*08:19, DRB1*08:20, DRB1*08:21, DRB1*08:22, DRB1*08:23, DRB1*08:24:01, DRB1*08: 24:02, DRB1*08:25, DRB1*08:26, DRB1*08:27, DRB1*08:28, DRB1*08:29, DRB1*08:30:01, DRB1*08:

30:02, DRB1*08:30:03, DRB1*08:31, DRB1*08:32, DRB1*08:33, DRB1*08:34, DRB1*08:35, DRB1*08:36: 01, DRB1*08:36:02, DRB1*08:37, DRB1*08:38, DRB1*08:39, DRB1*08:40, DRB1*08:41, DRB1*08:42, DRB1*08:43, DRB1*08:44, DRB1*08:45:01, DRB1*08: 45:02, DRB1*08:46, DRB1*08:47, DRB1*08:48, DRB1*08:49, DRB1*08:50, DRB1*08:51, DRB1*08:52, DRB1*08:53, DRB1*08:54, DRB1*08:55, DRB1*08:56, DRB1*08:57, DRB1*08:58, DRB1*08:59, DRB1*08:60N, DRB1*08:61, DRB1*08:62, DRB1*08:63, DRB1*08:64, DRB1*08:65, DRB1*08:66, DRB1*08:67, DRB1*08:68: 01, DRB1*08:68:02, DRB1*08:69, DRB1*08:70, DRB1*08:71, DRB1*08:72, DRB1*08:73, DRB1*08:74, DRB1*08:75, DRB1*08:76, DRB1*08:77, DRB1*08:78N, DRB1*08:79, DRB1*08:80, DRB1*08:81, DRB1*08:82, DRB1*08:83, DRB1*08:84, DRB1*08:85, DRB1*08:86, DRB1*08:87, DRB1*08:88, DRB1*08:89N, DRB1*08:90, DRB1*09:01:02:01, DRB1*09:01:02:02, DRB1*09:01:03, DRB1*09:01:04, DRB1*09:01:05, DRB1*09:01:06, DRB1*09:01:07, DRB1*09:01:08, DRB1*09:01:09, DRB1*09:01:10, DRB1*09:01:11, DRB1*09:02:01, DRB1*09:02:02, DRB1*09:03, DRB1*09:04, DRB1*09: 05, DRB1*09:06, DRB1*09:07, DRB1*09:08, DRB1*09: 09, DRB1*09:10, DRB1*09:11, DRB1*09:12, DRB1*09: 13, DRB1*09:14, DRB1*09:15, DRB1*09:16, DRB1*09: 17, DRB1*09:18, DRB1*09:19, DRB1*09:20, DRB1*09: 21, DRB1*09:22, DRB1*09:23, DRB1*09:24, DRB1*09: 25, DRB1*09:26, DRB1*09:27, DRB1*09:28, DRB1*09: 29, DRB1*09:30, DRB1*09:31, DRB1*09:32, DRB1*09: 33, DRB1*09:34, DRB1*09:35, DRB1*09:36, DRB1*09: 37N, DRB1*09:38, DRB1*09:39, DRB1*09:40, DRB1*10: 01:01:01, DRB1*10:01:01:02, DRB1*10:01:01:03, DRB1*10:01:02, DRB1*10:01:03, DRB1*10:01:04, DRB1*10:01:05, DRB1*10:01:06, DRB1*10:01:07, DRB1*10:01:08, DRB1*10:01:09, DRB1*10:01:10, DRB1*10:01:11, DRB1*10:01:12, DRB1*10:02, DRB1*10:03, DRB1*10:04, DRB1*10:05, DRB1*10:06, DRB1*10:07, DRB1*10:08, DRB1*10:09, DRB1*10:10, DRB1*10:11, DRB1*10:12, DRB1*10:13, DRB1*10:14, DRB1*10:15, DRB1*10:16, DRB1*10:17, DRB1*10:18, DRB1*10:19, DRB1*10:20, DRB1*10:21, DRB1*10:22, DRB1*10:23, DRB1*10:24, DRB1*10:25, DRB1*10:26, DRB1*10:27, DRB1*10:28, DRB1*10:29, DRB1*10:30, DRB1*10:31, DRB1*10:32, DRB1*10:33, DRB1*11: 01:01, DRB1*11:01:01:02, DRB1*11:01:01:03, DRB1*11: 01:01:04, DRB1*11:01:02, DRB1*11:01:03, DRB1*11:01: 04, DRB1*11:01:05, DRB1*11:01:06, DRB1*11:01:07, DRB1*11:01:08, DRB1*11:01:09, DRB1*11:01:10, DRB1*11:01:11, DRB1*11:01:12, DRB1*11:01:13, DRB1*11:01:14, DRB1*11:01:15, DRB1*11:01:16, DRB1*11:01:17, DRB1*11:01:18, DRB1*11:01:19, DRB1*11:01:20, DRB1*11:01:21, DRB1*11:01:22, DRB1*11:01:23, DRB1*11:01:24, DRB1*11:01:25, DRB1*11:01:26, DRB1*11:01:27, DRB1*11:01:28, DRB1*11:01:29, DRB1*11:01:30, DRB1*11:01:31, DRB1*11:01:32, DRB1*11:01:33, DRB1*11:02:01, DRB1*11:02:02, DRB1*11:02:03, DRB1*11:02:04, DRB1*11:02:05, DRB1*11:03:01, DRB1*11:03:02, DRB1*11:03:03, DRB1*11:03:04, DRB1*11:04:01, DRB1*11:04:02, DRB1*11:04:03, DRB1*11:04:04, DRB1*11:04:05, DRB1*11:04:06, DRB1*11:04:07, DRB1*11:04:08, DRB1*11:04:09, DRB1*11:04:10, DRB1*11:04:11, DRB1*11:04:12, DRB1*11:04:13, DRB1*11:04:14, DRB1*11:04:15, DRB1*11:04:16, DRB1*11:04:17, DRB1*11:04:18, DRB1*11:05, DRB1*11:06:01, DRB1*11:06:02, DRB1*11:06:03, DRB1*11:07:01, DRB1*11:07:02, DRB1*11:08:01,

DRB1*11:08:02, DRB1*11:08:03, DRB1*11:09, DRB1*11:100, DRB1*11:101:01, DRB1*11:101:02, DRB1*11:102:01, DRB1*11:102:02, DRB1*11:103:01, DRB1*11:103:02, DRB1*11:104, DRB1*11:105, DRB1*11:106, DRB1*11:107, DRB1*11:108, DRB1*11: 109, DRB1*11:10:01, DRB1*11:10:02, DRB1*11:110, DRB1*11:111, DRB1*11:112, DRB1*11:113, DRB1*11: 114, DRB1*11:115, DRB1*11:116, DRB1*11:117:01, DRB1*11:117:02, DRB1*11:118, DRB1*11:119, DRB1*11:11:01, DRB1*11:11:03, DRB1*11:120, DRB1*11:121, DRB1*11:122, DRB1*11:123, DRB1*11: 124:01, DRB1*11:124:02, DRB1*11:125, DRB1*11:126, DRB1*11:127, DRB1*11:128, DRB1*11:129, DRB1*11: 12:01, DRB1*11:12:02, DRB1*11:12:03, DRB1*11:130, DRB1*11:131, DRB1*11:132, DRB1*11:133, DRB1*11: 134, DRB1*11:135, DRB1*11:136, DRB1*11:137, DRB1*11:138, DRB1*11:139, DRB1*11:13:01, DRB1*11: 13:02, DRB1*11:140, DRB1*11:141, DRB1*11:142, DRB1*11:143, DRB1*11:144, DRB1*11:145, DRB1*11: 146, DRB1*11:147:01, DRB1*11:147:02, DRB1*11:148, DRB1*11:149, DRB1*11:14:01, DRB1*11:14:02, DRB1*11:15, DRB1*11:150, DRB1*11:151, DRB1*11: 152, DRB1*11:153, DRB1*11:154, DRB1*11:155, DRB1*11:156, DRB1*11:157, DRB1*11:158, DRB1*11: 159, DRB1*11:16, DRB1*11:160, DRB1*11:161, DRB1*11:162, DRB1*11:163, DRB1*11:164, DRB1*11: 165:01, DRB1*11:165:02, DRB1*11:166, DRB1*11:167, DRB1*11:168, DRB1*11:169N, DRB1*11:17, DRB1*11: 170, DRB1*11:171, DRB1*11:172, DRB1*11:173, DRB1*11:174, DRB1*11:175, DRB1*11:176, DRB1*11: 177, DRB1*11:178, DRB1*11:179, DRB1*11:18, DRB1*11:180, DRB1*11:181, DRB1*11:182, DRB1*11: 183, DRB1*11:184, DRB1*11:185, DRB1*11:186, DRB1*11:187, DRB1*11:188, DRB1*11:189, DRB1*11: 190, DRB1*11:191, DRB1*11:192, DRB1*11:193:01, DRB1*11:193:02, DRB1*11:194, DRB1*11:195, DRB1*11:196, DRB1*11:197, DRB1*11:198, DRB1*11: 199, DRB1*11:19:01, DRB1*11:19:02, DRB1*11:19:03, DRB1*11:20, DRB1*11:200, DRB1*11:201, DRB1*11: 202, DRB1*11:203, DRB1*11:204, DRB1*11:205, DRB1*11:206, DRB1*11:207, DRB1*11:208, DRB1*11: 209, DRB1*11:21, DRB1*11:210, DRB1*11:211, DRB1*11:212, DRB1*11:213, DRB1*11:214, DRB1*11: 215, DRB1*11:216, DRB1*11:217N, DRB1*11:218, DRB1*11:219, DRB1*11:22, DRB1*11:220, DRB1*11: 221, DRB1*11:222, DRB1*11:223, DRB1*11:224, DRB1*11:225, DRB1*11:226, DRB1*11:227, DRB1*11: 228, DRB1*11:229, DRB1*11:230, DRB1*11:231, DRB1*11:232, DRB1*11:233, DRB1*11:234, DRB1*11: 235, DRB1*11:236, DRB1*11:237, DRB1*11:238, DRB1*11:239, DRB1*11:23:01, DRB1*11:23:02, DRB1*11:240, DRB1*11:241, DRB1*11:242, DRB1*11: 243, DRB1*11:244, DRB1*11:245, DRB1*11:246N, DRB1*11:247, DRB1*11:248Q, DRB1*11:249, DRB1*11: 24:01, DRB1*11:24:02, DRB1*11:25, DRB1*11:250N, DRB1*11:251, DRB1*11:252, DRB1*11:253, DRB1*11: 254, DRB1*11:26, DRB1*11:27:01, DRB1*11:27:02, DRB1*11:27:03, DRB1*11:28:01, DRB1*11:28:02, DRB1*11:29:01, DRB1*11:29:02, DRB1*11:30, DRB1*11:31, DRB1*11:32, DRB1*11:33, DRB1*11:34, DRB1*11:35, DRB1*11:36, DRB1*11:37:01, DRB1*11: 37:02, DRB1*11:38, DRB1*11:39, DRB1*11:40, DRB1*11:41, DRB1*11:42:01, DRB1*11:42:02, DRB1*11:43, DRB1*11:44, DRB1*11:45, DRB1*11:46: 01, DRB1*11:46:02, DRB1*11:47, DRB1*11:48, DRB1*11:49:01, DRB1*11:49:02, DRB1*11:50, DRB1*11:51, DRB1*11:52, DRB1*11:53, DRB1*11:54:

01, DRB1*11:54:02, DRB1*11:55, DRB1*11:56, DRB1*11:57, DRB1*11:58:01, DRB1*11:58:02, DRB1*11:59, DRB1*11:60, DRB1*11:61, DRB1*11:62: 01, DRB1*11:62:02, DRB1*11:63:01, DRB1*11:63:02, DRB1*11:64, DRB1*11:65:01, DRB1*11:65:02, DRB1*11:66:01, DRB1*11:66:02, DRB1*11:67, DRB1*11:68, DRB1*11:69, DRB1*11:70, DRB1*11:72, DRB1*11:73, DRB1*11:74:01, DRB1*11:74:02, DRB1*11:75, DRB1*11:76, DRB1*11:77, DRB1*11:78, DRB1*11:79, DRB1*11:80, DRB1*11:81, DRB1*11:82, DRB1*11:83, DRB1*11:84:01, DRB1*11:84:02, DRB1*11:84:03, DRB1*11:85, DRB1*11:86, DRB1*11: 87, DRB1*11:88, DRB1*11:89, DRB1*11:90, DRB1*11: 91, DRB1*11:92, DRB1*11:93, DRB1*11:94, DRB1*11: 95, DRB1*11:96, DRB1*11:97, DRB1*11:98, DRB1*11: 99, DRB1*12:01:01:01, DRB1*12:01:01:02, DRB1*12:01: 01:03, DRB1*12:01:01:04, DRB1*12:01:01:05, DRB1*12: 01:01:06, DRB1*12:01:02, DRB1*12:01:03, DRB1*12:01: 04, DRB1*12:01:05, DRB1*12:01:06, DRB1*12:01:07, DRB1*12:01:08, DRB1*12:01:09, DRB1*12:02:01:01, DRB1*12:02:01:02, DRB1*12:02:01:03, DRB1*12:02:01: 04, DRB1*12:02:02, DRB1*12:02:03, DRB1*12:02:04, DRB1*12:02:05, DRB1*12:02:06, DRB1*12:02:07, DRB1*12:02:08, DRB1*12:02:09, DRB1*12:03:02, DRB1*12:03:03, DRB1*12:04, DRB1*12:05, DRB1*12: 06, DRB1*12:07, DRB1*12:08, DRB1*12:09, DRB1*12: 10, DRB1*12:11, DRB1*12:12, DRB1*12:13, DRB1*12: 14, DRB1*12:15, DRB1*12:16:01, DRB1*12:16:02, DRB1*12:16:03, DRB1*12:17, DRB1*12:18, DRB1*12: 19, DRB1*12:20, DRB1*12:21, DRB1*12:22, DRB1*12: 23, DRB1*12:24N, DRB1*12:25, DRB1*12:26, DRB1*12: 27, DRB1*12:28, DRB1*12:29, DRB1*12:30, DRB1*12: 31N, DRB1*12:32, DRB1*12:33, DRB1*12:34, DRB1*12: 35, DRB1*12:36, DRB1*12:37, DRB1*12:38, DRB1*12: 39, DRB1*12:40, DRB1*12:41, DRB1*12:42, DRB1*12: 43, DRB1*12:44, DRB1*12:45, DRB1*12:46, DRB1*12: 47, DRB1*12:48, DRB1*12:49, DRB1*12:50, DRB1*12: 51, DRB1*12:52, DRB1*12:53, DRB1*12:54, DRB1*12: 55, DRB1*12:56, DRB1*12:57, DRB1*12:58, DRB1*12: 59, DRB1*12:60N, DRB1*12:61, DRB1*12:62, DRB1*12: 63, DRB1*12:64, DRB1*12:65, DRB1*12:66, DRB1*12: 67, DRB1*12:68, DRB1*12:69, DRB1*12:70, DRB1*12: 71, DRB1*12:72N, DRB1*12:73, DRB1*12:74N, DRB1*12:75, DRB1*13:01:01:01, DRB1*13:01:01:02, DRB1*13:01:02, DRB1*13:01:03, DRB1*13:01:04, DRB1*13:01:05, DRB1*13:01:06, DRB1*13:01:07, DRB1*13:01:08, DRB1*13:01:09, DRB1*13:01:10, DRB1*13:01:11, DRB1*13:01:12, DRB1*13:01:13, DRB1*13:01:14, DRB1*13:01:15, DRB1*13:01:16, DRB1*13:01:17, DRB1*13:01:18, DRB1*13:01:19, DRB1*13:01:20, DRB1*13:01:21, DRB1*13:01:22, DRB1*13:01:23, DRB1*13:01:24, DRB1*13:01:25, DRB1*13:01:26, DRB1*13:02:01:01, DRB1*13:02:01:02, DRB1*13:02:01:03, DRB1*13:02:02, DRB1*13:02:03, DRB1*13:02:04, DRB1*13:02:05, DRB1*13:02:06, DRB1*13:02:07, DRB1*13:02:08, DRB1*13:02:09, DRB1*13:02:10, DRB1*13:02:11, DRB1*13:02:12, DRB1*13:02:13, DRB1*13:02:14, DRB1*13:02:15, DRB1*13:02:16, DRB1*13:02:17, DRB1*13:03:01, DRB1*13:03:02, DRB1*13:03:03, DRB1*13:03:04, DRB1*13:03:05, DRB1*13:03:06, DRB1*13:03:07, DRB1*13:03:08, DRB1*13:03:09, DRB1*13:04, DRB1*13:05:01, DRB1*13:05:02, DRB1*13:05:03, DRB1*13:06, DRB1*13:07:01, DRB1*13:07:02, DRB1*13:08, DRB1*13:09, DRB1*13:10, DRB1*13:100, DRB1*13:101, DRB1*13:102, DRB1*13:103, DRB1*13: 104, DRB1*13:105, DRB1*13:106, DRB1*13:107,

DRB1*13:108, DRB1*13:109, DRB1*13:110, DRB1*13: 111, DRB1*13:112, DRB1*13:113N, DRB1*13:114, DRB1*13:115, DRB1*13:116, DRB1*13:117, DRB1*13: 118, DRB1*13:119, DRB1*13:11:01, DRB1*13:11:02, DRB1*13:120, DRB1*13:121, DRB1*13:122, DRB1*13: 123, DRB1*13:124, DRB1*13:125, DRB1*13:126, DRB1*13:127, DRB1*13:128, DRB1*13:129, DRB1*13: 12:01, DRB1*13:12:02, DRB1*13:12:03, DRB1*13:12:04, DRB1*13:13, DRB1*13:130, DRB1*13:131, DRB1*13: 132, DRB1*13:133, DRB1*13:134, DRB1*13:135, DRB1*13:136, DRB1*13:137N, DRB1*13:138, DRB1*13: 139, DRB1*13:140, DRB1*13:141, DRB1*13:142N, DRB1*13:143, DRB1*13:144, DRB1*13:145, DRB1*13: 146, DRB1*13:147, DRB1*13:148, DRB1*13:149, DRB1*13:14:01, DRB1*13:14:02, DRB1*13:14:03, DRB1*13:15, DRB1*13:150, DRB1*13:151, DRB1*13: 152, DRB1*13:153, DRB1*13:154, DRB1*13:155, DRB1*13:156, DRB1*13:157, DRB1*13:158, DRB1*13: 159, DRB1*13:16, DRB1*13:160, DRB1*13:161, DRB1*13:162, DRB1*13:163, DRB1*13:164, DRB1*13: 165, DRB1*13:166, DRB1*13:167, DRB1*13:168, DRB1*13:169, DRB1*13:17, DRB1*13:170, DRB1*13: 171:01, DRB1*13:171:02, DRB1*13:172, DRB1*13:173, DRB1*13:174, DRB1*13:175, DRB1*13:176, DRB1*13: 177, DRB1*13:178, DRB1*13:179, DRB1*13:18, DRB1*13:180, DRB1*13:181, DRB1*13:182, DRB1*13: 183, DRB1*13:184, DRB1*13:185N, DRB1*13:186, DRB1*13:187, DRB1*13:188, DRB1*13:189, DRB1*13: 19, DRB1*13:190, DRB1*13:191, DRB1*13:192, DRB1*13:193, DRB1*13:194, DRB1*13:195, DRB1*13: 196, DRB1*13:197, DRB1*13:198, DRB1*13:199, DRB1*13:20, DRB1*13:200N, DRB1*13:201, DRB1*13: 202, DRB1*13:203, DRB1*13:204, DRB1*13:205, DRB1*13:206, DRB1*13:207, DRB1*13:208, DRB1*13: 209, DRB1*13:210, DRB1*13:211, DRB1*13:212, DRB1*13:213, DRB1*13:214, DRB1*13:215, DRB1*13: 216, DRB1*13:217, DRB1*13:218, DRB1*13:219, DRB1*13:21:01, DRB1*13:21:02, DRB1*13:220, DRB1*13:221, DRB1*13:222, DRB1*13:223, DRB1*13: 224, DRB1*13:225, DRB1*13:226, DRB1*13:227, DRB1*13:228, DRB1*13:229, DRB1*13:22:01, DRB1*13: 22:02, DRB1*13:230, DRB1*13:231, DRB1*13:232, DRB1*13:233, DRB1*13:234, DRB1*13:235, DRB1*13: 236, DRB1*13:237, DRB1*13:238, DRB1*13:239, DRB1*13:23:01, DRB1*13:23:02, DRB1*13:24, DRB1*13:240, DRB1*13:241, DRB1*13:242:01, DRB1*13:242:02, DRB1*13:243, DRB1*13:244, DRB1*13:245, DRB1*13:246, DRB1*13:247, DRB1*13: 248, DRB1*13:249N, DRB1*13:25, DRB1*13:250, DRB1*13:251, DRB1*13:252N, DRB1*13:253, DRB1*13: 254, DRB1*13:255N, DRB1*13:256, DRB1*13:257, DRB1*13:258, DRB1*13:259, DRB1*13:260, DRB1*13: 261, DRB1*13:262, DRB1*13:263, DRB1*13:264, DRB1*13:265, DRB1*13:266, DRB1*13:267, DRB1*13: 268N, DRB1*13:269, DRB1*13:26:01, DRB1*13:26:02, DRB1*13:27, DRB1*13:270, DRB1*13:271, DRB1*13: 272, DRB1*13:273, DRB1*13:274, DRB1*13:275, DRB1*13:276, DRB1*13:277, DRB1*13:278Q, DRB1*13: 279, DRB1*13:28:01, DRB1*13:28:02, DRB1*13:29, DRB1*13:30, DRB1*13:31, DRB1*13:32, DRB1*13:33: 01, DRB1*13:33:02, DRB1*13:33:03, DRB1*13:34, DRB1*13:35, DRB1*13:36, DRB1*13:37, DRB1*13:38, DRB1*13:39, DRB1*13:40, DRB1*13:41, DRB1*13:42, DRB1*13:43, DRB1*13:44, DRB1*13:45, DRB1*13:46, DRB1*13:47, DRB1*13:48, DRB1*13:49, DRB1*13:50: 01, DRB1*13:50:02, DRB1*13:50:03, DRB1*13:51, DRB1*13:52, DRB1*13:53, DRB1*13:54, DRB1*13:55,

DRB1*13:56, DRB1*13:57, DRB1*13:58, DRB1*13:59, DRB1*13:60, DRB1*13:61:01, DRB1*13:61:02, DRB1*13:62, DRB1*13:63, DRB1*13:64, DRB1*13:65, DRB1*13:66:01, DRB1*13:66:02, DRB1*13:67, DRB1*13:68, DRB1*13:69, DRB1*13:70, DRB1*13:71, DRB1*13:72, DRB1*13:73, DRB1*13:74, DRB1*13:75, DRB1*13:76, DRB1*13:77, DRB1*13:78, DRB1*13:79, DRB1*13:80, DRB1*13:81, DRB1*13:82, DRB1*13:83, DRB1*13:84, DRB1*13:85, DRB1*13:86, DRB1*13:87, DRB1*13:88, DRB1*13:89:01, DRB1*13:89:02, DRB1*13:90, DRB1*13:91, DRB1*13:92, DRB1*13:93, DRB1*13:94:01, DRB1*13:94:02, DRB1*13:95, DRB1*13:96:01, DRB1*13:96:02, DRB1*13:97:01, DRB1*13:97:02, DRB1*13:98, DRB1*13:99, DRB1*14: 01:01, DRB1*14:01:02, DRB1*14:01:03, DRB1*14:01:04, DRB1*14:02:01:01, DRB1*14:02:01:02, DRB1*14:02:02, DRB1*14:02:03, DRB1*14:02:04, DRB1*14:02:05, DRB1*14:02:06, DRB1*14:02:07, DRB1*14:03:01, DRB1*14:03:02, DRB1*14:04:01, DRB1*14:04:02, DRB1*14:04:03, DRB1*14:04:04, DRB1*14:04:05, DRB1*14:04:06, DRB1*14:05:01:01, DRB1*14:05:01:02, DRB1*14:05:02, DRB1*14:05:03, DRB1*14:05:04, DRB1*14:06:01, DRB1*14:06:02, DRB1*14:06:03, DRB1*14:06:04, DRB1*14:07:01, DRB1*14:07:02, DRB1*14:08, DRB1*14:09, DRB1*14:10, DRB1*14:100, DRB1*14:101, DRB1*14:102, DRB1*14:103, DRB1*14: 104, DRB1*14:105, DRB1*14:106, DRB1*14:107, DRB1*14:108, DRB1*14:109, DRB1*14:11, DRB1*14: 110, DRB1*14:111, DRB1*14:112, DRB1*14:113, DRB1*14:114, DRB1*14:115, DRB1*14:116, DRB1*14: 117, DRB1*14:118, DRB1*14:119, DRB1*14:120, DRB1*14:121, DRB1*14:122, DRB1*14:123, DRB1*14: 124, DRB1*14:125, DRB1*14:126:01, DRB1*14:126:02, DRB1*14:127:01, DRB1*14:127:02, DRB1*14:128, DRB1*14:129, DRB1*14:12:01, DRB1*14:12:02, DRB1*14:13, DRB1*14:130, DRB1*14:131, DRB1*14: 132, DRB1*14:133, DRB1*14:134, DRB1*14:135, DRB1*14:136, DRB1*14:137N, DRB1*14:138, DRB1*14: 139, DRB1*14:14, DRB1*14:140, DRB1*14:141, DRB1*14:142, DRB1*14:143, DRB1*14:144, DRB1*14: 145, DRB1*14:146, DRB1*14:147, DRB1*14:148, DRB1*14:149, DRB1*14:15, DRB1*14:150, DRB1*14: 151, DRB1*14:152N, DRB1*14:153, DRB1*14:154, DRB1*14:155, DRB1*14:156, DRB1*14:157, DRB1*14: 158, DRB1*14:159, DRB1*14:16, DRB1*14:160, DRB1*14:161, DRB1*14:162, DRB1*14:163, DRB1*14: 164, DRB1*14:165, DRB1*14:166N, DRB1*14:167, DRB1*14:168, DRB1*14:169, DRB1*14:17, DRB1*14: 170, DRB1*14:171, DRB1*14:172, DRB1*14:173, DRB1*14:174, DRB1*14:175, DRB1*14:176, DRB1*14: 177, DRB1*14:178, DRB1*14:179, DRB1*14:18, DRB1*14:180, DRB1*14:181, DRB1*14:182, DRB1*14: 183, DRB1*14:184, DRB1*14:185, DRB1*14:186, DRB1*14:187, DRB1*14:188N, DRB1*14:189, DRB1*14: 19, DRB1*14:190, DRB1*14:191, DRB1*14:192, DRB1*14:193, DRB1*14:194, DRB1*14:195N, DRB1*14: 196, DRB1*14:197N, DRB1*14:198, DRB1*14:199, DRB1*14:20, DRB1*14:200, DRB1*14:201, DRB1*14: 202, DRB1*14:203, DRB1*14:204, DRB1*14:205, DRB1*14:206, DRB1*14:207, DRB1*14:208, DRB1*14: 209, DRB1*14:21, DRB1*14:210Q, DRB1*14:211, DRB1*14:22, DRB1*14:23:01, DRB1*14:23:02, DRB1*14:23:03, DRB1*14:23:04, DRB1*14:24, DRB1*14:25:01, DRB1*14:25:02, DRB1*14:26, DRB1*14:27:01, DRB1*14:27:02, DRB1*14:28, DRB1*14:29, DRB1*14:30, DRB1*14:31, DRB1*14:32: 01, DRB1*14:32:02, DRB1*14:32:03, DRB1*14:33,

DRB1*14:34, DRB1*14:35, DRB1*14:36, DRB1*14:37, DRB1*14:38:01, DRB1*14:38:02, DRB1*14:39, DRB1*14:40, DRB1*14:41, DRB1*14:42, DRB1*14:43, DRB1*14:44:01, DRB1*14:44:02, DRB1*14:44:03, DRB1*14:45, DRB1*14:46, DRB1*14:47, DRB1*14:48, DRB1*14:49, DRB1*14:50, DRB1*14:51, DRB1*14:52, DRB1*14:53, DRB1*14:54:01:01, DRB1*14:54:01:02, DRB1*14:54:01:03, DRB1*14:54:01:04, DRB1*14:54:02, DRB1*14:54:03, DRB1*14:54:04, DRB1*14:54:05, DRB1*14:54:06, DRB1*14:54:07, DRB1*14:55, DRB1*14:56, DRB1*14:57, DRB1*14:58, DRB1*14:59, DRB1*14:60, DRB1*14:61, DRB1*14:62, DRB1*14:63, DRB1*14:64, DRB1*14:65, DRB1*14:67, DRB1*14:68: 01, DRB1*14:68:02, DRB1*14:69, DRB1*14:70, DRB1*14:71, DRB1*14:72, DRB1*14:73, DRB1*14:74, DRB1*14:75, DRB1*14:76, DRB1*14:77, DRB1*14:78, DRB1*14:79, DRB1*14:80, DRB1*14:81, DRB1*14:82, DRB1*14:83, DRB1*14:84, DRB1*14:85, DRB1*14:86, DRB1*14:87, DRB1*14:88, DRB1*14:89, DRB1*14:90, DRB1*14:91, DRB1*14:92N, DRB1*14:93, DRB1*14:94, DRB1*14:95, DRB1*14:96, DRB1*14:97, DRB1*14:98, DRB1*14:99, DRB1*15:01:01:01, DRB1*15:01:01:02, DRB1*15:01:01:03, DRB1*15:01:01:04, DRB1*15:01:01: 05, DRB1*15:01:02, DRB1*15:01:03, DRB1*15:01:04, DRB1*15:01:05, DRB1*15:01:06, DRB1*15:01:07, DRB1*15:01:08, DRB1*15:01:09, DRB1*15:01:10, DRB1*15:01:11, DRB1*15:01:12, DRB1*15:01:13, DRB1*15:01:14, DRB1*15:01:15, DRB1*15:01:16, DRB1*15:01:17, DRB1*15:01:18, DRB1*15:01:19, DRB1*15:01:20, DRB1*15:01:21, DRB1*15:01:22, DRB1*15:01:23, DRB1*15:01:24, DRB1*15:01:25, DRB1*15:01:26, DRB1*15:01:27, DRB1*15:01:28, DRB1*15:01:29, DRB1*15:01:30, DRB1*15:01:31, DRB1*15:01:32, DRB1*15:01:33, DRB1*15:01:34, DRB1*15:01:35, DRB1*15:01:36, DRB1*15:01:37, DRB1*15:01:38, DRB1*15:01:39, DRB1*15:01:40, DRB1*15:01:41, DRB1*15:02:01:01, DRB1*15:02:01:02, DRB1*15:02:01:03, DRB1*15:02:02, DRB1*15:02:03, DRB1*15:02:04, DRB1*15:02:05, DRB1*15:02:06, DRB1*15:02:07, DRB1*15:02:08, DRB1*15:02:09, DRB1*15:02:10, DRB1*15:02:11, DRB1*15:02:12, DRB1*15:02:13, DRB1*15:02:14, DRB1*15:02:15, DRB1*15:02:16, DRB1*15:02:17, DRB1*15:02:18, DRB1*15:02:19, DRB1*15:03:01:01, DRB1*15:03:01:02, DRB1*15:03:01:03, DRB1*15:03:02, DRB1*15:03:03, DRB1*15:03:04, DRB1*15:04, DRB1*15:05, DRB1*15: 06:01, DRB1*15:06:02, DRB1*15:06:03, DRB1*15:06:04, DRB1*15:07:01, DRB1*15:07:02, DRB1*15:07:03, DRB1*15:08, DRB1*15:09, DRB1*15:10, DRB1*15:100, DRB1*15:101, DRB1*15:102, DRB1*15:103, DRB1*15: 104:01, DRB1*15:104:02, DRB1*15:104:03, DRB1*15: 105:01, DRB1*15:105:02, DRB1*15:106, DRB1*15:107, DRB1*15:108, DRB1*15:109, DRB1*15:110, DRB1*15: 111, DRB1*15:112, DRB1*15:113N, DRB1*15:114, DRB1*15:115N, DRB1*15:116, DRB1*15:117, DRB1*15: 118, DRB1*15:119, DRB1*15:11:01, DRB1*15:11:02, DRB1*15:12, DRB1*15:120, DRB1*15:121, DRB1*15: 122, DRB1*15:123, DRB1*15:124, DRB1*15:125, DRB1*15:126, DRB1*15:127, DRB1*15:128, DRB1*15: 129N, DRB1*15:13, DRB1*15:130, DRB1*15:131, DRB1*15:132, DRB1*15:133, DRB1*15:134N, DRB1*15: 135, DRB1*15:136, DRB1*15:137N, DRB1*15:138N, DRB1*15:139, DRB1*15:14, DRB1*15:140, DRB1*15: 141, DRB1*15:142, DRB1*15:143, DRB1*15:144, DRB1*15:145, DRB1*15:146, DRB1*15:147, DRB1*15: 148N, DRB1*15:149, DRB1*15:150, DRB1*15:151, DRB1*15:152, DRB1*15:153, DRB1*15:154N, DRB1*15:

155, DRB1*15:156, DRB1*15:157, DRB1*15:158, DRB1*15:159N, DRB1*15:15:01, DRB1*15:15:02, DRB1*15:15:03, DRB1*15:16, DRB1*15:160, DRB1*15:161, DRB1*15:162, DRB1*15:163N, DRB1*15:164Q, DRB1*15:165, DRB1*15:166, DRB1*15:167, DRB1*15:168, DRB1*15:169, DRB1*15:170, DRB1*15:17N, DRB1*15:18, DRB1*15:19, DRB1*15:20, DRB1*15:21, DRB1*15:22, DRB1*15:23, DRB1*15:24, DRB1*15:25, DRB1*15:26, DRB1*15:27, DRB1*15:28, DRB1*15:29, DRB1*15:30, DRB1*15:31:01, DRB1*15:31:02, DRB1*15:32, DRB1*15:33, DRB1*15:34, DRB1*15:35, DRB1*15:36, DRB1*15:37:01, DRB1*15:37:02, DRB1*15:38, DRB1*15:39, DRB1*15:40, DRB1*15:41, DRB1*15:42, DRB1*15:43, DRB1*15:44, DRB1*15:45, DRB1*15:46, DRB1*15:47, DRB1*15:48, DRB1*15:49, DRB1*15:50N, DRB1*15:51, DRB1*15:52, DRB1*15:53, DRB1*15:54, DRB1*15:55, DRB1*15:56, DRB1*15:57, DRB1*15:58, DRB1*15:59, DRB1*15:60, DRB1*15:61, DRB1*15:62, DRB1*15:63, DRB1*15:64, DRB1*15:65, DRB1*15:66:01, DRB1*15:66:02, DRB1*15:67, DRB1*15:68, DRB1*15:69, DRB1*15:70, DRB1*15:71, DRB1*15:72, DRB1*15:73, DRB1*15:74, DRB1*15:75, DRB1*15:76, DRB1*15:77, DRB1*15:78, DRB1*15:79, DRB1*15:80N, DRB1*15:81, DRB1*15:82, DRB1*15:83, DRB1*15:84, DRB1*15:85, DRB1*15:86, DRB1*15:87, DRB1*15:88, DRB1*15:89, DRB1*15:90, DRB1*15:91, DRB1*15:92, DRB1*15:93, DRB1*15:94, DRB1*15:95, DRB1*15:96, DRB1*15:97, DRB1*15:98, DRB1*15:99, DRB1*16:01:01, DRB1*16:01:02, DRB1*16:01:03, DRB1*16:01:04, DRB1*16:01:05, DRB1*16:01:06, DRB1*16:01:07, DRB1*16:01:08, DRB1*16:01:09, DRB1*16:01:10, DRB1*16:01:11, DRB1*16:01:12, DRB1*16:01:13, DRB1*16:01:14, DRB1*16:01:15, DRB1*16:01:16, DRB1*16:02:01:01, DRB1*16:02:01:02, DRB1*16:02:01:03, DRB1*16:02:02, DRB1*16:02:03, DRB1*16:02:04, DRB1*16:02:05, DRB1*16:02:06, DRB1*16:02:07, DRB1*16:02:08, DRB1*16:03, DRB1*16:04:01, DRB1*16:04:02, DRB1*16:05:01, DRB1*16:05:02, DRB1*16:07, DRB1*16:08, DRB1*16:09:01, DRB1*16:09:02, DRB1*16:10:01, DRB1*16:10:02, DRB1*16:11, DRB1*16:12, DRB1*16:13N, DRB1*16:14, DRB1*16:15, DRB1*16:16, DRB1*16:17, DRB1*16:18, DRB1*16:19, DRB1*16:20, DRB1*16:21N, DRB1*16:22, DRB1*16:23, DRB1*16:24, DRB1*16:25, DRB1*16:26, DRB1*16:27, DRB1*16:28, DRB1*16:29, DRB1*16:30, DRB1*16:31, DRB1*16:32, DRB1*16:33, DRB1*16:34, DRB1*16:35, DRB1*16:36, DRB1*16:37, DRB1*16:38:01, DRB1*16:38:02, DRB1*16:39, DRB1*16:40, DRB1*16:41N, DRB1*16:42, DRB1*16:43, DRB1*16:44, DRB1*16:45, DRB1*16:46, DRB1*16:47, DRB1*16:48, DRB1*16:49, DRB1*16:50, DRB1*16:51, DRB1*16:52, DRB1*16:53, DRB1*16:54, DRB1*16:55N, DRB1*16:56, DRB3*01:01:02:01, DRB3*01:01:02:02, DRB3*01:01:02:03, DRB3*01:01:03, DRB3*01:01:04, DRB3*01:01:05, DRB3*01:01:06, DRB3*01:01:07, DRB3*01:01:08, DRB3*01:01:09, DRB3*01:01:10, DRB3*01:02, DRB3*01:03, DRB3*01:04, DRB3*01:05, DRB3*01:06, DRB3*01:07, DRB3*01:08, DRB3*01:09, DRB3*01:10, DRB3*01:11, DRB3*01:12, DRB3*01:13, DRB3*01:14, DRB3*01:15, DRB3*01:16, DRB3*01:17, DRB3*01:18, DRB3*01:19, DRB3*01:20, DRB3*01:21, DRB3*01:22, DRB3*01:23, DRB3*01:24, DRB3*01:25, DRB3*01:26N, DRB3*01:27, DRB3*01:28, DRB3*01:29, DRB3*01:30, DRB3*01:31, DRB3*01:32, DRB3*01:33, DRB3*01:34, DRB3*01:35, DRB3*01:36, DRB3*01:37, DRB3*01:38, DRB3*01:39, DRB3*01:40:01N, DRB3*01:40:02N, DRB3*01:41, DRB3*01:42, DRB3*01:43, DRB3*01:44,

DRB3*01:45, DRB3*01:46, DRB3*01:47, DRB3*01:48, DRB3*01:49, DRB3*01:50, DRB3*01:51, DRB3*01:52, DRB3*01:53, DRB3*01:54, DRB3*01:55, DRB3*01:56, DRB3*01:57, DRB3*01:58, DRB3*01:59, DRB3*01:60, DRB3*01:61, DRB3*01:62, DRB3*02:01, DRB3*02:02:01:01, DRB3*02:02:01:02, DRB3*02:02:01:03, DRB3*02:02:01:04, DRB3*02:02:02, DRB3*02:02:03, DRB3*02:02:04, DRB3*02:02:05, DRB3*02:02:06, DRB3*02:02:07, DRB3*02:02:08, DRB3*02:02:09, DRB3*02:02:10, DRB3*02:02:11, DRB3*02:02:12, DRB3*02:02:13, DRB3*02:02:14, DRB3*02:02:15, DRB3*02:02:16, DRB3*02:02:17, DRB3*02:02:18, DRB3*02:02:19, DRB3*02:02:20, DRB3*02:02:21, DRB3*02:03, DRB3*02:04, DRB3*02:05, DRB3*02:06, DRB3*02:07, DRB3*02:08, DRB3*02:09, DRB3*02:10, DRB3*02:11, DRB3*02:12, DRB3*02:13, DRB3*02:14, DRB3*02:15, DRB3*02:16, DRB3*02:17, DRB3*02:18, DRB3*02:19, DRB3*02:20, DRB3*02:21, DRB3*02:22:01, DRB3*02:22:02, DRB3*02:23, DRB3*02:24, DRB3*02:25, DRB3*02:26, DRB3*02:27, DRB3*02:28, DRB3*02:29N, DRB3*02:30, DRB3*02:31:01, DRB3*02:31:02, DRB3*02:32, DRB3*02:33, DRB3*02:34, DRB3*02:35, DRB3*02:36, DRB3*02:37, DRB3*02:38, DRB3*02:39, DRB3*02:40, DRB3*02:41, DRB3*02:42, DRB3*02:43, DRB3*02:44, DRB3*02:45, DRB3*02:46, DRB3*02:47, DRB3*02:48, DRB3*02:49, DRB3*02:50, DRB3*02:51, DRB3*02:52, DRB3*02:53, DRB3*02:54, DRB3*02:55N, DRB3*02:56, DRB3*02:57, DRB3*02:58, DRB3*02:59, DRB3*02:60, DRB3*02:61Q, DRB3*02:62, DRB3*02:63, DRB3*02:64, DRB3*02:65, DRB3*02:66, DRB3*02:67N, DRB3*02:68, DRB3*02:69, DRB3*02:70, DRB3*02:71, DRB3*02:72, DRB3*02:73, DRB3*02:74, DRB3*02:75, DRB3*02:76, DRB3*02:77, DRB3*02:78, DRB3*02:79, DRB3*02:80N, DRB3*02:81, DRB3*02:82, DRB3*02:83, DRB3*02:84, DRB3*02:85, DRB3*02:86, DRB3*02:87, DRB3*02:88, DRB3*02:89, DRB3*02:90, DRB3*02:91, DRB3*02:92, DRB3*02:93, DRB3*02:94, DRB3*02:95N, DRB3*03:01:01:01, DRB3*03:01:01:02, DRB3*03:01:02, DRB3*03:01:03, DRB3*03:01:04, DRB3*03:01:05, DRB3*03:01:06, DRB3*03:01:07, DRB3*03:02, DRB3*03:03, DRB3*03:04, DRB3*03:05, DRB3*03:06, DRB3*03:07, DRB3*03:08, DRB3*03:09, DRB3*03:10, DRB3*03:11, DRB3*03:12, DRB3*03:13, DRB3*03:14, DRB3*03:15, DRB3*03:16, DRB3*03:17, DRB3*03:18, DRB3*03:19, DRB3*03:20, DRB3*03:21, DRB3*03:22, DRB3*03:23, DRB3*03:24, DRB3*03:25, DRB4*01:01:01, DRB4*01:01:02, DRB4*01:01:03, DRB4*01:01:04, DRB4*01:01:05, DRB4*01:01:06, DRB4*01:02, DRB4*01:03:01:01, DRB4*01:03:01:02N, DRB4*01:03:01:03, DRB4*01:03:01:04, DRB4*01:03:01:05, DRB4*01:03:01:06, DRB4*01:03:01:07, DRB4*01:03:01:08, DRB4*01:03:01:09, DRB4*01:03:01:10, DRB4*01:03:01:11, DRB4*01:03:02, DRB4*01:03:03, DRB4*01:03:04, DRB4*01:03:05, DRB4*01:03:06, DRB4*01:03:07, DRB4*01:03:08, DRB4*01:03:09, DRB4*01:03:10, DRB4*01:03:11, DRB4*01:04, DRB4*01:05, DRB4*01:06, DRB4*01:07:01, DRB4*01:07:02, DRB4*01:08, DRB4*01:09, DRB4*01:10, DRB4*01:11, DRB4*01:12, DRB4*01:13, DRB4*01:14, DRB4*01:15, DRB4*01:16N, DRB4*01:17, DRB4*01:18, DRB4*01:19, DRB4*01:20, DRB4*01:21, DRB4*01:22, DRB4*01:23, DRB4*01:24, DRB4*01:25, DRB4*01:26, DRB4*01:27, DRB4*01:28, DRB4*01:29, DRB4*01:30, DRB4*01:31, DRB4*01:32, DRB4*01:33, DRB4*01:34, DRB4*01:35, DRB4*01:36, DRB4*01:37, DRB4*01:38N, DRB4*01:39, DRB4*01:40, DRB4*01:41, DRB4*01:42, DRB4*01:43, DRB4*01:44, DRB4*01:45, DRB4*01:46, DRB4*01:47, DRB4*01:48,

DRB4*01:49, DRB4*01:50, DRB4*01:51, DRB4*01:52, DRB4*01:53, DRB4*01:54N, DRB4*01:55, DRB4*01: 56N, DRB4*01:57N, DRB4*01:58, DRB4*01:59, DRB4*01:60, DRB4*01:61N, DRB4*01:62, DRB4*01:63, DRB4*01:64, DRB4*01:65N, DRB4*01:66, DRB4*01:67, DRB4*01:68, DRB4*01:69, DRB4*01:70, DRB4*01:71N, DRB4*01:72, DRB4*01:73, DRB4*01:74, DRB4*01:75, DRB4*01:76, DRB4*01:77, DRB4*01:78, DRB4*01:79, DRB4*01:80N, DRB4*01:81, DRB4*01:82, DRB4*01:83, DRB4*01:84N, DRB4*01:85, DRB4*01:86, DRB4*01:87, DRB4*01:88, DRB4*01:89, DRB4*01:90, DRB4*01:91, DRB4*01:92, DRB4*01:93, DRB4*02:01N, DRB5*01:01: 01:01, DRB5*01:01:01:02, DRB5*01:01:02, DRB5*01:01: 03, DRB5*01:01:04, DRB5*01:02, DRB5*01:03, DRB5*01:04, DRB5*01:05, DRB5*01:06, DRB5*01:07, DRB5*01:08N, DRB5*01:09, DRB5*01:10N, DRB5*01: 11, DRB5*01:12, DRB5*01:13, DRB5*01:14, DRB5*01: 15, DRB5*01:16, DRB5*01:17, DRB5*01:18, DRB5*01: 19, DRB5*01:20, DRB5*01:21, DRB5*01:22:01, DRB5*01:22:02, DRB5*01:23, DRB5*01:24, DRB5*01: 25, DRB5*01:26, DRB5*01:27N, DRB5*01:28, DRB5*01: 29, DRB5*01:30, DRB5*01:31, DRB5*01:32, DRB5*01: 33, DRB5*01:34, DRB5*01:35, DRB5*01:36, DRB5*01: 37, DRB5*01:38, DRB5*01:39, DRB5*01:40, DRB5*01: 41, DRB5*01:42, DRB5*01:43, DRB5*01:44, DRB5*01: 45, DRB5*01:46, DRB5*01:47, DRB5*01:48N, DRB5*01: 49N, DRB5*01:50, DRB5*01:51, DRB5*01:52N, DRB5*01:53N, DRB5*01:54, DRB5*01:55, DRB5*02:02: 01, DRB5*02:02:02, DRB5*02:02:03, DRB5*02:03, DRB5*02:04, DRB5*02:05, DRB5*02:06, DRB5*02:07, DRB5*02:08, DRB5*02:09, DRB5*02:10, DRB5*02:11, DRB5*02:12, DRB5*02:13, DRB5*02:14, DRB5*02:15, DRB5*02:16, DRB5*02:17, DRB5*02:18, DRB5*02:19N, DRB5*02:20, DRB5*02:21, DRB5*02:22, DRB5*02:23, DRB5*02:24 and any combination thereof.

In some aspects, the HLA class II molecule is a monomer. In some aspects, the HLA class II molecule is a dimer. In some aspects, the HLA class II molecule is a multimer. In some aspects, the HLA class II molecule is a trimer. In some aspects, the HLA class II molecule is a tetramer. In some aspects, the HLA class II molecule is a pentamer.

Certain aspects of the present disclosure are directed to antigen presenting cells (APCs) comprising any HLA class II molecule disclosed herein. In certain aspects, the APC expressed the HLA class II molecule on the surface of the APC. In certain aspects, the APC comprises more than one HLA class II molecule disclosed herein.

II.E. Vaccines

Certain aspects of the present disclosure a cancer vaccine comprising a peptide comprising an amino acid sequence as set forth in SEQ ID NO: 13. In some aspects, the cancer vaccine comprises a peptide that consists of the amino acid sequence set forth in SEQ ID NO: 13. In some aspects, the vaccine further comprises one or more excipient. In some aspects, the vaccine further comprises one or more additional peptides. In some aspects, the one or more additional peptides comprise one or more additional epitopes.

III. Methods of the Disclosure

Certain aspects of the present disclosure are directed to methods of treating a cancer in a subject in need thereof. Other aspects of the present disclosure are directed to methods of engineering an antigen-targeting cell. Other aspects of the present disclosure are directed to methods of enriching a target population of T cells obtained from a human subject.

III.A. Methods of Treating Cancer

Certain aspects of the present disclosure are directed to methods of treating a cancer in a subject in need thereof, comprising administering to the subject a nucleic acid molecule disclosed herein, a recombinant TCR disclosed herein, a bispecific TCR disclosed herein, an epitope disclosed herein, or an HLA class II molecule disclosed herein, or a vector or cell comprising any of the above.

In some aspects, the cancer is selected from melanoma, bone cancer, renal cancer, prostate cancer, breast cancer, colon cancer, lung cancer, cutaneous or intraocular malignant melanoma, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia (AML), chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In some aspects, the cancer melanoma.

In some aspects, the cancer is relapsed. In some aspects, the cancer is refractory. In some aspects, the cancer is advanced. In some aspects, the cancer is metastatic.

In some aspects, the methods disclosed herein treat a cancer in a subject. In some aspects, the methods disclosed herein reduce the severity of one or more symptom of the cancer. In some aspects, the methods disclosed herein reduce the size or number of a tumor derived from the cancer. In some aspects, the methods disclosed herein increase the overall survival of the subject, relative to a subject not provided the methods disclosed herein. In some aspects, the methods disclosed herein increase the progressive-free survival of the subject, relative to a subject not provided the methods disclosed herein. In some aspects, the methods disclosed herein lead to a partial response in the subject. In some aspects, the methods disclosed herein lead to a complete response in the subject.

In some aspects, the methods disclosed herein comprise treating a cancer in a subject in need thereof, comprising administering to the subject a cell described herein, wherein the cell comprises a nucleic acid molecule disclosed herein, a vector disclosed herein, a recombinant TCR disclosed herein, and/or a bispecific antibody disclosed herein. In some aspects, the cell is a T cell. In some aspects, the cell is a cell that is modified to express CD4.

In some aspects, the cell, e.g., a T cell, is obtained from the subject. In some aspects, the cell, e.g., a T cell, is obtained from a donor other than the subject.

In some aspects, the subject is preconditioned prior to administering the cells. The preconditioning can comprise any substance that promotes T cell function and/or survival. In some aspects, the preconditioning comprises administering to the subject a chemotherapy, a cytokine, a protein, a small molecule, or any combination thereof. In some aspects, the preconditioning comprises administering an interleukin. In some aspects, the preconditioning comprises administering IL-2, IL-4, IL-7, IL-9, IL-15, IL-21, or any combination thereof. In some aspects, the preconditioning comprises administering cyclophosphamide, fludarabine, or both. In some aspects, the preconditioning comprises administering vitamin C, an AKT inhibitor, ATRA (vesanoid, tretinoin), rapamycin, or any combination thereof.

III.B. Methods of Engineering an Antigen-Targeting Cell

Certain aspects of the present disclosure are directed to methods of engineering an antigen-targeting cell. In some aspects, the antigen is a CCND1 antigen. In some aspects, the method comprises transducing a cell with a nucleic acid molecule disclosed herein or a vector disclosed herein. The cell can be any cell described herein. In some aspects, the cell is a T cell described herein. In some aspects, the cell is a cell that is modified to express CD4, as described herein. In some aspects, the cell, e.g., the T cell, is obtained from a subject in need of a T cell therapy. In some aspects, the cell is obtained from a donor other than the subject in need of the T cell therapy. In some aspects, the cell is a T cell or a natural killer cell.

III.C. Methods of Enriching a Target Population of T Cells

Certain aspects of the present disclosure are directed to methods of enriching a target population of T cells obtained from a human subject. In some aspects, the method comprises contacting the T cells with an HLA class II molecule disclosed herein. In some aspects, the method comprises contacting the T cells with an APC disclosed herein. In some aspects, following the contacting, the enriched population of T cells comprises a higher number of T cells capable of binding the HLA class II molecule relative to the number of T cells capable of binding the HLA class II molecule prior to the contacting.

In some aspects, the method comprises contacting the T cells in vitro with a peptide, wherein the peptide comprises the amino acid sequence set forth in SEQ ID NO: 13. In some aspects, the method comprises contacting the T cells in vitro with a peptide, wherein the peptide consists of the amino acid sequence set forth in SEQ ID NO: 13. In some aspects, following the contacting, the enriched population of T cells comprises a higher number of T cells capable of binding the HLA class II molecule relative to the number of T cells capable of binding the HLA class II molecule prior to the contacting.

Some aspects of the present disclosure are directed to a method of selecting a T cell capable of targeting a tumor cell. In some aspects, the method comprises contacting a population of isolated T cells in vitro with a peptide, wherein the peptide consists of an amino acid sequence as set forth in SEQ ID NO: 13. In some aspects, the T cells are obtained from a human subject.

The T cells obtained from the human subject can be any T cells disclosed herein. In some aspects, the T cells obtained from the human subject are tumor infiltrating lymphocytes (TIL).

In some aspects, the method further comprises administering to the human subject the enriched T cells. In some aspects, the subject is preconditioned prior to receiving the T cells, as described herein.

All of the various aspects, aspects, and options described herein can be combined in any and all variations.

All publications, patents, and patent applications mentioned in this specification are herein incorporated by reference to the same extent as if each individual publication, patent, or patent application was specifically and individually indicated to be incorporated by reference.

Having generally described this disclosure, a further understanding can be obtained by reference to the examples provided herein. These examples are for purposes of illustration only and are not intended to be limiting.

EXAMPLES

Example 1—Methods

Cells

Peripheral mononuclear cells were obtained via density gradient centrifugation (Ficoll-Paque PLUS, GE Healthcare Life Sciences, Marlborough, MA). The K562 cell line is an erythroleukemic cell line with defective HLA class I/II expression. K562-based artificial APCs (aAPCs) individually expressing various HLA class II genes as a single HLA allele in conjunction with CD80 and CD83 have been reported previously (Butler et al., *PloS One* 7, e30229 (2012). The Jurkat 76 cell line is a T cell leukemic cell line lacking endogenous TCR, CD4, and CD8 expression. Jurkat 76/CD4 cells were generated by retrovirally transducing the human CD4 gene. HEK293T cells and melanoma cell lines were grown in DMEM supplemented with 10% FBS and 50 μg/ml gentamicin (Thermo Fisher Scientific, Waltham, MA). The K562 and Jurkat 76 cell lines were cultured in RPMI 1640 supplemented with 10% FBS and 50 μg/ml gentamicin.

Peptides

The $CCND_{1219-238}$ synthetic peptide was purchased from Genscript (Piscataway, NJ) and dissolved at 50 μg/ml in DMSO.

Genes

Novel TCR genes were cloned via 5'-rapid amplification of cDNA ends (RACE) PCR using SMARTer RACE 5'/3' Kit (Takara Bio, Shiga, Japan) and sequenced as previously described. All genes were cloned into the pMX retroviral vector and transduced into cell lines using the 293GPG and PG13 cell-based retrovirus system.

Antibodies

The following antibodies were used for flow cytometry analysis: APC-Cy7-conjugated anti-CD4 (RPA-T4, Biolegend, San Diego, CA)[44], and PE-conjugated anti-His tag (AD1.1.10, Abcam, Cambridge, MA). Dead cells were distinguished with the LIVE/DEAD Fixable Near-IR Dead Cell Stain Kit 465 (Thermo Fisher Scientific, Waltham, MA). Stained cells were analyzed with Canto II or LSRFortessa X-20 (BD Biosciences, Franklin Lakes, NJ). Cell sorting was conducted using a FACS Aria II (BD Biosciences, Franklin Lakes, NJ). Data analysis was performed using FlowJo software (Tree Star, Ashland, OR).

The following antibodies were used for immunoblot analysis: anti-β-actin (C4, Santa Cruz Biotechnology, Santa Cruz, CA), anti-CCND1 (EPR2241, Abeam, Cambridge, MA), HRP-conjugated goat anti-mouse IgG (H+L) secondary antibody (Promega, Fitchburg, WI), and HRP-conjugated anti-rabbit IgG (H+L) secondary antibody (Promega, Fitchburg, WI), as applicable.

TCR Transduction into Primary T Cells $CD3^+$ and $CD4^+$ T cells were purified using the Pan T Cell Isolation Kit (Miltenyi Biotec, Bergisch Gladbach, Germany) and CD4$^+$ T Cell Isolation Kit (Miltenyi Biotec, Bergisch Gladbach, Germany), respectively. Purified T cells were stimulated with aAPC/mOKT3 irradiated with 200 Gy at an E:T ratio of 20:1. Starting the following day, activated T cells were retrovirally transduced with the cloned. TCR genes via centrifugation for 1 hour at 1,000×g at 32° C. for 3 consecutive days or using a Retronectin-coated plate (Takara Bio, Shiga, Japan). On the following day, 100 IU/ml IL-2 and 10 ng/ml IL-15 were added to the TCR-transduced T cells. The culture medium was replenished every 2-3 days.

Generation of the HLA Class II Monomer and Dimer

The extracellular domain of the wild-type class II α gene was fused with an acidic leucine zipper via a GGGS linker followed by a 6× His tag via a GS linker (see SEQ ID NO: 15; Table 5). The ectodomain of the class gene carrying mutations (see SEQ ID NO: 14) was similarly linked with a basic leucine zipper via a GGGS linker (see SEQ ID NO: 14). HEK293T cells and A375 cells were transfected with the α and β genes using the 293GPG cell-based retrovirus system and cultured in DMEM supplemented with 10% FBS and 50 μg/ml gentatnicin. For DP4 dimer staining, HEK293T cells stably secreting soluble DP4$^{L112W/V141M}$ protein were grown until confluent, and the medium was changed to serum-free 293 SFM II medium (Thermo Fisher Scientific, Waltham, MA). After forty-eight hours, the conditioned medium was harvested and concentrated using Amicon Ultra filters (molecular weight cut-off (MWCO) 10 kDa) (MilliporeSigma, Burlington, MA). The soluble HLA class II-containing supernatant was then mixed with 100 μg/ml peptide of interest for 20-24 hours at 37° C. for in vitro peptide exchange. Monomer that was not subjected to peptide exchange was used as a control. The concentration of the monomer was measured by specific ELISA using a nickel-coated plate (XPressBio, Frederick, MD) and an anti-His tag biotinylated mAb (AD1.1.10, R&D Systems, Minneapolis, MN). Soluble HLA class II monomer was dimerized using PE-conjugated anti-His mAb (AD1.1.10, Abeam, Cambridge, MA) at a 2:1 molar ratio for 1.5 hours at 4° C. for staining.

days. After 2 weeks of stimulation, the T cells were subjected to DP4$^{L112W/V141M}$ dimer staining.

HLA Class II Dimer Staining

Primary T cells and Jurkat 76/CD4 T cells transduced with exogenous TCR gene were pretreated with 50 nM dasatinib (LC Laboratories, Woburn, MA) for 30 min at 37° C.[46] and stained with 5-15 μg/ml class II dimer for 4-5 hours at room temperature. After washing, cell surface molecules were counterstained with an APC-Cy7-conjugated anti-CD4 mAb.

ELISPOT Assay

Cytokine ELISPOT assays were performed as previously reported (see, e.g., Yamashita et al., Nat. Commun. 8:15244 (2017); and Anczurowski et al., Sci. Rep. 8:4804 (2018)).

Immunoblotting

Immunoblot analysis was performed as previously reported (see, e.g., Yamashita et al., Nat. Commun. 8:15244 (2017); and Anczurowski et al., Sci. Rep. 8:4804 (2018)).

Statistical Analysis

Statistical analysis was performed using GraphPad Prism 6.0 software (GraphPad Software, San Diego, CA). Unpaired two-tailed Student's t-tests were used for two-sample comparisons. No statistical method was used to predetermine sample size. The investigators were not blinded to allocation during the experiments or outcome assessment. The experiments were not randomized.

Example 2—Characterization of CCND1$_{219-238}$ TCR

Primary CD4$^+$ T cells isolated from six DP4$^+$ melanoma patients were stimulated only once with DP4-aAPCs individually pulsed with a peptide fragment of CCND1 (219-238) and stained with cognate DP4$^{L112W/V141M}$ dimers. To avoid potential in vitro priming, weak stimulatory conditions were utilized. The CCND1$_{219-238}$ was found to be immunogenic by dimer staining (data not shown).

TABLE 5

| HLA-DP Class II Molecules |
| --- |

Signal Peptide; DPB1*04:01 L112W/V141M Extracellular Domain; Gly/Ser Linker; Zip Sequences and His tag sequences) (SEQ ID NO: 14)
MMRPIVLVILFATSALARATPENYLFQGRQECYAFNGTQRFLERYIYNREEFARFDSDVGEFRAVTELGRPAAE
YWNSQKDILEEKRAVTDRMCRHNYELGGPMTLQRRVQPRVNVSPSKKGPLQHHNWLVCHVTDFYPGSIQVRWFL
NGQEETAGVMSTNLIRNGDWTFQILVMLEMTPQQGDVYTCQVEHTSLDSPVTVEWKAQSDSARSKGGGGSLEIE
AAFLERENTALETRVAELPQRVQRLRNRVSQYRTRYGPLGGGK Signal Peptide; DPA1*01:03 Extracellular Domain; Gly/Ser Linker, Zip Sequences and His tag sequences) (SEQ ID NO: 15)
MMRPIVLVLLFATSALAIKADHVSTYAAFVQTHRPTGEFMFEFDEDEMFYVDLDKKETVWHLEEFGQAFSFEAQ
GGLANIAILNNNLNTLIQRSNHTQATNDPPEVTVFPKEPVELGQPNTLICHIDKFFPPVLNVTWLCNGELVTEG
VAESLFLPRTDYSFHFHKYLTFVPSAEDFYDCRVEHWGLDQPLLKHWEAQEPIQMPETTETGGGGSLEIRAAFL
RQRNTALRIEVAELEQEVQRLENEVSQYETRYGPLGGGEGSHHHHHH Stimulation of DP4-Restricted Antigen-Specific CD4$^+$ T Cells CD4$^+$ T cells were purified using a CD4$^+$ T Cell Isolation Kit (Miltenyi Biotec, Bergisch Gladbach, Germany). Purified T cells were stimulated with DP4-expressing aAPCs pulsed with DP4-restricted peptides at 10 μg/ml and irradiated at 200 Gy at an E:T ratio of 20:1. After forty-eight hours, 10 IU/ml IL-2 and 10 ng/ml IL-15 were added to the CD4$^+$ T cells. The culture medium supplemented with IL-2 (10 IU/ml) and IL-15 (10 ng/ml) was replenished every 2-3

Figure 1A:
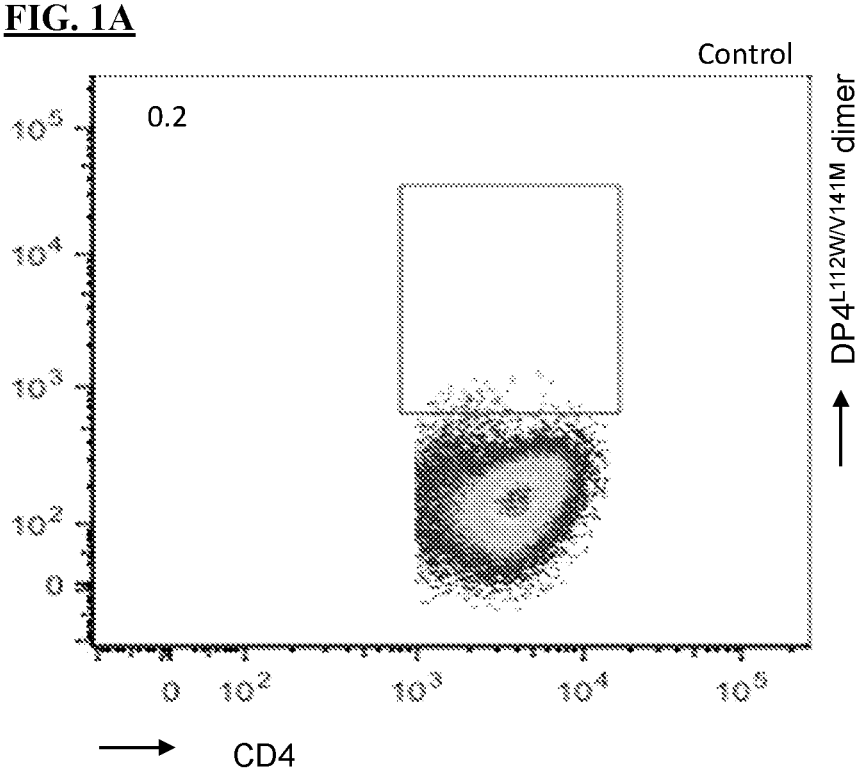
FIGS. 1A-1B are graphical representations of $DP4^{L112W/V141M}$ dimer staining of peptide-specific CD4$^+$ T cells from melanoma patients. Primary CD4$^+$ T cells were purified from six DP4$^+$ melanoma patients and stimulated with DP4-expressing aAPCs individually pulsed with $CCND1_{219-238}$ peptides and stained with cognate $DP4^{L112W/V141M}$ dimers. Examples of $DP4^{L112W/V141M}$ dimer staining are shown.
Figure 1B:
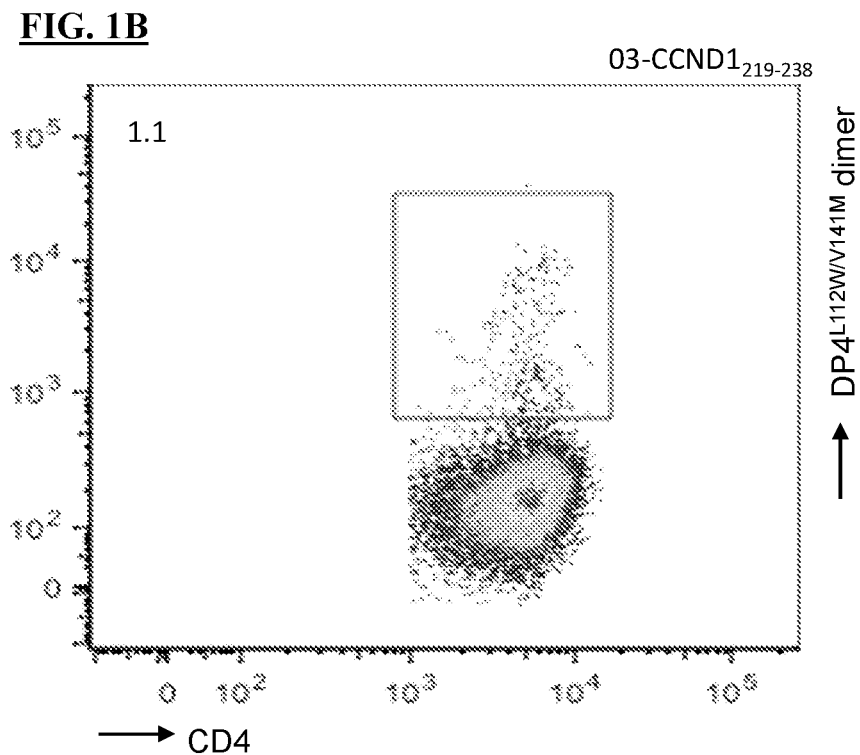
Figures 2A, 2B, 2C, 2D:
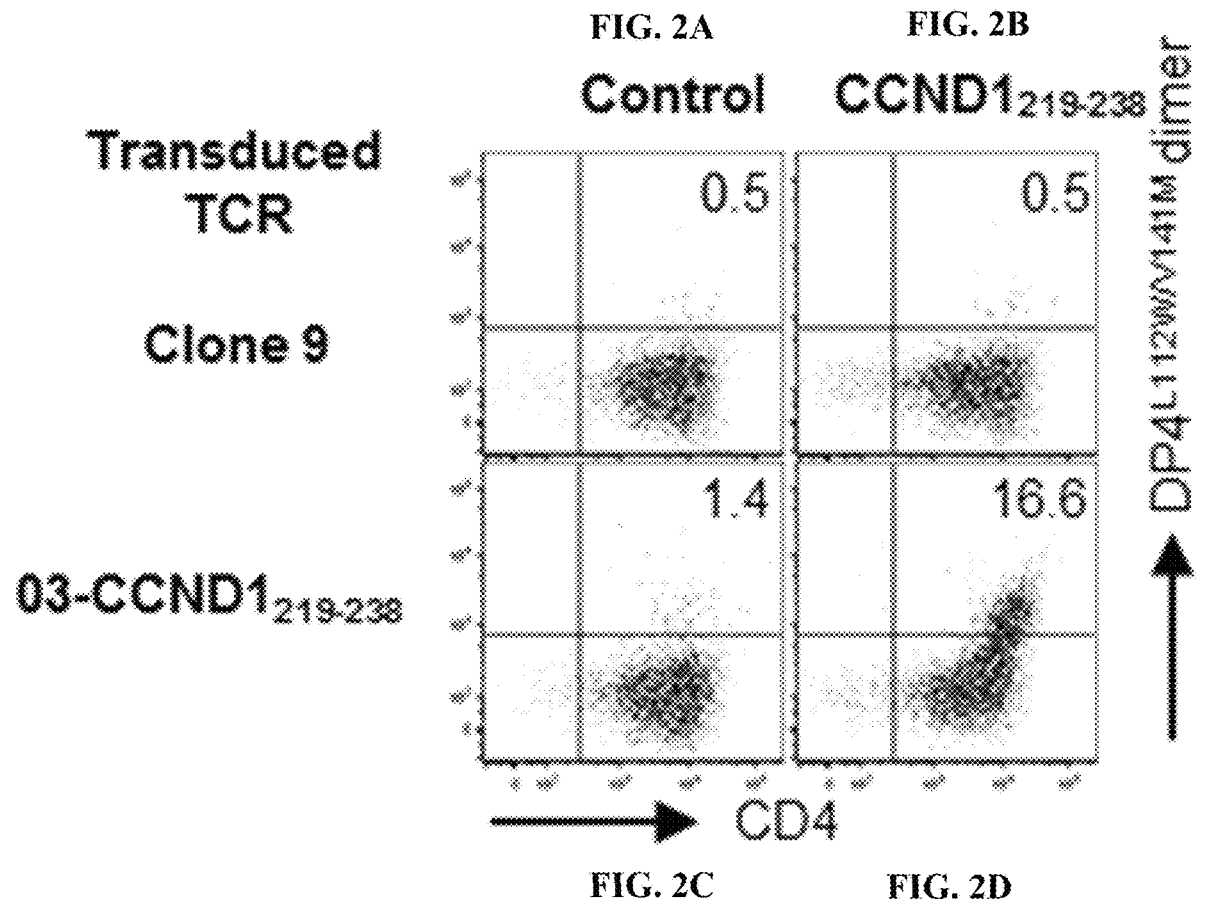
FIGS. 2A-2D are graphical representations of data illustrating that DP4-restricted (03-CCND1$_{219-238}$) TCRs isolated from $DP4^{L112W/V141M}$ dimer-positive cells and reconstituted in human TCR-defective CD4$^+$ T cells were functional in a DP4-restricted and antigen-specific manner.

To validate the dimer staining results, we cloned a DP4-restricted TCR gene specific for CCND1$_{219-238}$ (FIGS. 1A-1B and Table 6) from the dimer-positive T cells. When clonotypically reconstituted in human CD4$^+$ TCR-deficient T cells, the CCND1$_{219-238}$ TCR was successfully stained by the cognate DP4$^{L112W/V141M}$ dimers (FIGS. 2A-2D) and were functional in a DP4-restricted and antigen-specific manner (FIG. 3).

The TCR 03-CCND1$_{219-238}$ was able to recognize a cognate peptide that was endogenously processed and presented by DP4 (FIGS. 4A-4E and 5A-5B).

TABLE 6

| | | | | DP4-Restricted TCR | | | | |
|---|---|---|---|---|---|---|---|---|
| No. | Peptide | TRAV | TRAJ | TCR-alpha CDR 3 | TRBV | TRBJ | TCR-beta CDR 3 | |
| 03 | CCND1$_{219-238}$ | 2*01 | 21*01 | CAVCTLYNFNKFYF (SEQ ID NO: 7) | 6-5*01 | 2-1*01 | CASLTDNNEQFF (SEQ ID NO: 10) | |

The invention claimed is:

1. A nucleic acid molecule comprising (i) a first nucleotide sequence encoding a recombinant T cell receptor (TCR) or an antigen binding portion thereof that specifically binds human G1/S-specific cyclin-D1 (CCND1) ("anti-CCND1 TCR"); wherein the anti-CCND1 TCR comprises an alpha chain variable domain comprising an alpha chain CDR1, an alpha chain CDR2, and an alpha chain CDR3; and a beta chain variable domain comprising a beta chain CDR1, a beta chain CDR2, and a beta chain CDR3; and wherein:

(a) the beta chain CDR3 of the anti-CCND1 TCR comprises the amino acid sequence as set forth in SEQ ID NO: 10;

(b) the beta chain CDR2 of the anti-CCND1 TCR comprises the amino acid sequence as set forth in SEQ ID NO: 9;

(c) the beta chain CDR1 of the anti-CCND1 TCR comprises the amino acid sequence as set forth in SEQ ID NO: 8;

(d) the alpha chain CDR3 of the anti-CCND1 TCR comprises the amino acid sequence as set forth in SEQ ID NO: 7;

(e) the alpha chain CDR2 of the anti-CCND1 TCR comprises the amino acid sequence as set forth in SEQ ID NO: 6; and (f) the alpha chain CDR1 of the anti-CCND1 TCR comprises the amino acid sequence as set forth in SEQ ID NO: 5; and (ii) a second nucleotide sequence, wherein the second nucleotide sequence or the polypeptide encoded by the second nucleotide sequence inhibits the expression of an endogenous TCR.

2. The nucleic acid molecule of claim 1, wherein (i) the alpha chain variable domain of the anti-CCND1 TCR comprises the amino acid sequence of the variable domain present in the amino acid sequence set forth in SEQ ID NO: 1;

(ii) the beta chain variable domain of the anti-CCND1 TCR comprises the amino acid sequence of the variable domain present in the amino acid sequence set forth in SEQ ID NO: 2; or (iii) both (i) and (ii).

3. The nucleic acid molecule of claim 1, wherein:

(a) the anti-CCND1 TCR further comprises an alpha chain constant region, wherein the alpha chain constant region of the anti-CCND1 TCR is different from a constant region of an endogenous alpha chain, and wherein (i) the alpha chain constant region of the anti-CCND1 TCR comprises an amino acid sequence having at least about 85% sequence identity to a constant region present in the amino acid sequence set forth in SEQ ID NO: 1; or (ii) the alpha chain constant region of the anti-CCND1 TCR comprises an amino acid sequence comprising at least 1 amino acid substitution relative to a constant region present in the amino acid sequence set forth in SEQ ID NO: 1;

(b) the anti-CCND1 TCR further comprises a beta chain constant region, wherein the beta chain constant region of the anti-CCND1 TCR is different from a constant region of an endogenous beta chain, and wherein (i) the beta chain constant region of the anti-CCND1 TCR comprises an amino acid sequence having at least about 85% sequence identity to the constant region present in the amino acid sequence set forth in SEQ ID NO: 2; or (ii) the beta chain constant region comprises an amino acid sequence comprising at least 1, amino acid substitution relative to the constant region present in the amino acid sequence set forth in SEQ ID NO: 2; or (c) both (a) and (b).

4. The nucleic acid molecule of claim 1, wherein the second nucleotide sequence comprises one or more siRNAs that reduce the expression of endogenous TCRs, wherein the one or more siRNAs are complementary to a target sequence within a nucleotide sequence encoding a constant region of the endogenous TCRs.

5. The nucleic acid molecule of claim 1, wherein the anti-CCND1 TCR comprises an alpha chain comprising the amino acid sequence set forth in SEQ ID NO: 1, and a beta chain comprising the amino acid sequence set forth in SEQ ID NO: 2.

6. A cell comprising the nucleic acid molecule of claim 5.

7. The cell of claim 6, which further expresses CD3.

8. The cell of claim 6, which is a T cell.

9. The cell of claim 6, which is an NK cell, a natural killer T (NKT) cell, or an ILC cell.

10. A vector comprising the nucleic acid molecule of claim 1.

11. A cell comprising the nucleic acid molecule of claim 1.

12. The cell of claim 11, which further expresses CD3.

13. The cell of claim 11, which is a T cell.

14. The cell of claim 11, which is a natural killer (NK) cell, a natural killer T (NKT) cell, or an ILC cell.

15. A method of treating a cancer in a subject in need thereof, comprising administering to the subject the cell of claim 11, wherein the cell is a T cell or an NK cell.

16. The method of claim 15, wherein the cancer comprises melanoma, bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, or combinations of said cancers.

17. The method of claim 15, wherein the cancer is locally advanced, advanced, or metastatic.

18. The method of claim 15, wherein the cancer is relapsed or refractory.

19. The method of claim 15, wherein the cells are obtained from the subject.

* * * * *

SEQUENCE LISTING

<160> NUMBER OF SEQ ID NOS: 28

<210> SEQ ID NO 1
<211> LENGTH: 248
<212> TYPE: PRT
<213> ORGANISM: Artificial Sequence
<220> FEATURE:
<223> OTHER INFORMATION: synthetic construct

<400> SEQUENCE: 1

Lys Asp Gln Val Phe Gln Pro Ser Thr Val Ala Ser Ser Glu Gly Ala
1               5                   10                  15

Val Val Glu Ile Phe Cys Asn His Ser Val Ser Asn Ala Tyr Asn Phe
            20                  25                  30

Phe Trp Tyr Leu His Phe Pro Gly Cys Ala Pro Arg Leu Leu Val Lys
        35                  40                  45

Gly Ser Lys Pro Ser Gln Gln Gly Arg Tyr Asn Met Thr Tyr Glu Arg
    50                  55                  60

Phe Ser Ser Ser Leu Leu Ile Leu Gln Val Arg Glu Ala Asp Ala Ala
65                  70                  75                  80

Val Tyr Tyr Cys Ala Val Cys Thr Leu Tyr Asn Phe Asn Lys Phe Tyr
                85                  90                  95

Phe Gly Ser Gly Thr Lys Leu Asn Val Lys Pro Asn Ile Gln Asn Pro
            100                 105                 110

Asp Pro Ala Val Tyr Gln Leu Arg Asp Ser Lys Ser Ser Asp Lys Ser
        115                 120                 125

Val Cys Leu Phe Thr Asp Phe Asp Ser Gln Thr Asn Val Ser Gln Ser
        130                 135                 140

Lys Asp Ser Asp Val Tyr Ile Thr Asp Lys Thr Val Leu Asp Met Arg
145                 150                 155                 160

Ser Met Asp Phe Lys Ser Asn Ser Ala Val Ala Trp Ser Asn Lys Ser
            165                 170                 175

Asp Phe Ala Cys Ala Asn Ala Phe Asn Asn Ser Ile Ile Pro Glu Asp
            180                 185                 190

Thr Phe Phe Pro Ser Pro Glu Ser Ser Cys Asp Val Lys Leu Val Glu
            195                 200                 205

Lys Ser Phe Glu Thr Asp Thr Asn Leu Asn Phe Gln Asn Leu Ser Val
        210                 215                 220

Ile Gly Phe Arg Ile Leu Leu Leu Lys Val Ala Gly Phe Asn Leu Leu
225                 230                 235                 240

Met Thr Leu Arg Leu Trp Ser Ser
                245

<210> SEQ ID NO 2
<211> LENGTH: 288
<212> TYPE: PRT
<213> ORGANISM: Artificial Sequence
<220> FEATURE:
<223> OTHER INFORMATION: synthetic construct

```
<400> SEQUENCE: 2

Gly Val Thr Gln Thr Pro Lys Phe Gln Val Leu Lys Thr Gly Gln Ser
1               5                   10                  15

Met Thr Leu Gln Cys Ala Gln Asp Met Asn His Glu Tyr Met Ser Trp
                20                  25                  30

Tyr Arg Gln Asp Pro Gly Met Gly Leu Arg Leu Ile His Tyr Ser Val
        35                  40                  45

Gly Ala Gly Ile Thr Asp Gln Gly Glu Val Pro Asn Gly Tyr Asn Val
    50                  55                  60

Ser Arg Ser Thr Thr Glu Asp Phe Pro Leu Arg Leu Leu Ser Ala Ala
65                  70                  75                  80

Pro Ser Gln Thr Ser Val Tyr Phe Cys Ala Ser Leu Thr Asp Asn Asn
                85                  90                  95

Glu Gln Phe Phe Gly Pro Gly Thr Arg Leu Thr Val Leu Glu Asp Leu
                100                 105                 110

Lys Asn Val Phe Pro Pro Glu Val Ala Val Phe Glu Pro Ser Glu Ala
        115                 120                 125

Glu Ile Ser His Thr Gln Lys Ala Thr Leu Val Cys Leu Ala Thr Gly
    130                 135                 140

Phe Tyr Pro Asp His Val Glu Leu Ser Trp Trp Val Asn Gly Lys Glu
145                 150                 155                 160

Val His Ser Gly Val Ser Thr Asp Pro Gln Pro Leu Lys Glu Gln Pro
                165                 170                 175

Ala Leu Asn Asp Ser Arg Tyr Cys Leu Ser Ser Arg Leu Arg Val Ser
                180                 185                 190

Ala Thr Phe Trp Gln Asn Pro Arg Asn His Phe Arg Cys Gln Val Gln
                195                 200                 205

Phe Tyr Gly Leu Ser Glu Asn Asp Glu Trp Thr Gln Asp Arg Ala Lys
    210                 215                 220

Pro Val Thr Gln Ile Val Ser Ala Glu Ala Trp Gly Arg Ala Asp Cys
225                 230                 235                 240

Gly Phe Thr Ser Glu Ser Tyr Gln Gln Gly Val Leu Ser Ala Thr Ile
                245                 250                 255

Leu Tyr Glu Ile Leu Leu Gly Lys Ala Thr Leu Tyr Ala Val Leu Val
                260                 265                 270

Ser Ala Leu Val Leu Met Ala Met Val Lys Arg Lys Asp Ser Arg Gly
                275                 280                 285

<210> SEQ ID NO 3

<400> SEQUENCE: 3

000

<210> SEQ ID NO 4

<400> SEQUENCE: 4

000

<210> SEQ ID NO 5
<211> LENGTH: 6
<212> TYPE: PRT
<213> ORGANISM: Artificial Sequence
<220> FEATURE:
<223> OTHER INFORMATION: synthetic construct
```

```
<400> SEQUENCE: 5

Val Ser Asn Ala Tyr Asn
1               5

<210> SEQ ID NO 6
<211> LENGTH: 4
<212> TYPE: PRT
<213> ORGANISM: Artificial Sequence
<220> FEATURE:
<223> OTHER INFORMATION: synthetic construct

<400> SEQUENCE: 6

Gly Ser Lys Pro
1

<210> SEQ ID NO 7
<211> LENGTH: 14
<212> TYPE: PRT
<213> ORGANISM: Artificial Sequence
<220> FEATURE:
<223> OTHER INFORMATION: synthetic construct

<400> SEQUENCE: 7

Cys Ala Val Cys Thr Leu Tyr Asn Phe Asn Lys Phe Tyr Phe
1               5                   10

<210> SEQ ID NO 8
<211> LENGTH: 5
<212> TYPE: PRT
<213> ORGANISM: Artificial Sequence
<220> FEATURE:
<223> OTHER INFORMATION: synthetic construct

<400> SEQUENCE: 8

Met Asn His Glu Tyr
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic construct

<400> SEQUENCE: 9

Ser Val Gly Ala Gly Ile
1               5

<210> SEQ ID NO 10
<211> LENGTH: 12
<212> TYPE: PRT
<213> ORGANISM: Artificial Sequence
<220> FEATURE:
<223> OTHER INFORMATION: synthetic construct

<400> SEQUENCE: 10

Cys Ala Ser Leu Thr Asp Asn Asn Glu Gln Phe Phe
1               5                   10

<210> SEQ ID NO 11

<400> SEQUENCE: 11

000

<210> SEQ ID NO 12
```

-continued

<400> SEQUENCE: 12

000

<210> SEQ ID NO 13
<211> LENGTH: 20
<212> TYPE: PRT
<213> ORGANISM: Artificial Sequence
<220> FEATURE:
<223> OTHER INFORMATION: synthetic construct

<400> SEQUENCE: 13

Ser Pro Asn Asn Phe Leu Ser Tyr Tyr Arg Leu Thr Arg Phe Leu Ser
1               5                   10                  15

Arg Val Ile Lys
            20

<210> SEQ ID NO 14
<211> LENGTH: 265
<212> TYPE: PRT
<213> ORGANISM: Artificial Sequence
<220> FEATURE:
<223> OTHER INFORMATION: synthetic construct

<400> SEQUENCE: 14

Met Met Arg Pro Ile Val Leu Val Leu Leu Phe Ala Thr Ser Ala Leu
1               5                   10                  15

Ala Arg Ala Thr Pro Glu Asn Tyr Leu Phe Gln Gly Arg Gln Glu Cys
                20                  25                  30

Tyr Ala Phe Asn Gly Thr Gln Arg Phe Leu Glu Arg Tyr Ile Tyr Asn
            35                  40                  45

Arg Glu Glu Phe Ala Arg Phe Asp Ser Asp Val Gly Glu Phe Arg Ala
        50                  55                  60

Val Thr Glu Leu Gly Arg Pro Ala Ala Glu Tyr Trp Asn Ser Gln Lys
65                  70                  75                  80

Asp Ile Leu Glu Glu Lys Arg Ala Val Pro Asp Arg Met Cys Arg His
                85                  90                  95

Asn Tyr Glu Leu Gly Gly Pro Met Thr Leu Gln Arg Arg Val Gln Pro
            100                 105                 110

Arg Val Asn Val Ser Pro Ser Lys Lys Gly Pro Leu Gln His His Asn
        115                 120                 125

Trp Leu Val Cys His Val Thr Asp Phe Tyr Pro Gly Ser Ile Gln Val
    130                 135                 140

Arg Trp Phe Leu Asn Gly Gln Glu Glu Thr Ala Gly Val Met Ser Thr
145                 150                 155                 160

Asn Leu Ile Arg Asn Gly Asp Trp Thr Phe Gln Ile Leu Val Met Leu
                165                 170                 175

Glu Met Thr Pro Gln Gln Gly Asp Val Tyr Thr Cys Gln Val Glu His
            180                 185                 190

Thr Ser Leu Asp Ser Pro Val Thr Val Glu Trp Lys Ala Gln Ser Asp
        195                 200                 205

Ser Ala Arg Ser Lys Gly Gly Gly Gly Ser Leu Glu Ile Glu Ala Ala
    210                 215                 220

Phe Leu Glu Arg Glu Asn Thr Ala Leu Glu Thr Arg Val Ala Glu Leu
225                 230                 235                 240

Arg Gln Arg Val Gln Arg Leu Arg Asn Arg Val Ser Gln Tyr Arg Thr
                245                 250                 255

```
Arg Tyr Gly Pro Leu Gly Gly Gly Lys
            260             265

<210> SEQ ID NO 15
<211> LENGTH: 269
<212> TYPE: PRT
<213> ORGANISM: Artificial Sequence
<220> FEATURE:
<223> OTHER INFORMATION: synthetic construct

<400> SEQUENCE: 15

Met Met Arg Pro Ile Val Leu Val Leu Leu Phe Ala Thr Ser Ala Leu
1               5                   10                  15

Ala Ile Lys Ala Asp His Val Ser Thr Tyr Ala Ala Phe Val Gln Thr
                20                  25                  30

His Arg Pro Thr Gly Glu Phe Met Phe Glu Phe Asp Glu Asp Glu Met
            35                  40                  45

Phe Tyr Val Asp Leu Asp Lys Lys Glu Thr Val Trp His Leu Glu Glu
        50                  55                  60

Phe Gly Gln Ala Phe Ser Phe Glu Ala Gln Gly Gly Leu Ala Asn Ile
65                  70                  75                  80

Ala Ile Leu Asn Asn Asn Leu Asn Thr Leu Ile Gln Arg Ser Asn His
                85                  90                  95

Thr Gln Ala Thr Asn Asp Pro Pro Glu Val Thr Val Phe Pro Lys Glu
                100                 105                 110

Pro Val Glu Leu Gly Gln Pro Asn Thr Leu Ile Cys His Ile Asp Lys
            115                 120                 125

Phe Phe Pro Pro Val Leu Asn Val Thr Trp Leu Cys Asn Gly Glu Leu
            130                 135                 140

Val Thr Glu Gly Val Ala Glu Ser Leu Phe Leu Pro Arg Thr Asp Tyr
145                 150                 155                 160

Ser Phe His Lys Phe His Tyr Leu Thr Phe Val Pro Ser Ala Glu Asp
                165                 170                 175

Phe Tyr Asp Cys Arg Val Glu His Trp Gly Leu Asp Gln Pro Leu Leu
                180                 185                 190

Lys His Trp Glu Ala Gln Glu Pro Ile Gln Met Pro Glu Thr Thr Glu
            195                 200                 205

Thr Gly Gly Gly Gly Ser Leu Glu Ile Arg Ala Ala Phe Leu Arg Gln
            210                 215                 220

Arg Asn Thr Ala Leu Arg Thr Glu Val Ala Glu Leu Glu Gln Glu Val
225                 230                 235                 240

Gln Arg Leu Glu Asn Glu Val Ser Gln Tyr Glu Thr Arg Tyr Gly Pro
                245                 250                 255

Leu Gly Gly Gly Lys Gly Ser His His His His His
            260                 265

<210> SEQ ID NO 16
<211> LENGTH: 295
<212> TYPE: PRT
<213> ORGANISM: Artificial Sequence
<220> FEATURE:
<223> OTHER INFORMATION: synthetic construct

<400> SEQUENCE: 16

Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
                20                  25                  30
```

-continued

```
Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Glu Val Phe Pro Leu
65                  70                  75                  80

Ala Met Asn Tyr Leu Asp Arg Phe Leu Ser Leu Glu Pro Val Lys Lys
                85                  90                  95

Ser Arg Leu Gln Leu Leu Gly Ala Thr Cys Met Phe Val Ala Ser Lys
                100                 105                 110

Met Lys Glu Thr Ile Pro Leu Thr Ala Glu Lys Leu Cys Ile Tyr Thr
                115                 120                 125

Asp Asn Ser Ile Arg Pro Glu Glu Leu Leu Gln Met Glu Leu Leu Leu
        130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295
```

```
<210> SEQ ID NO 17
<211> LENGTH: 458
<212> TYPE: PRT
<213> ORGANISM: Artificial Sequence
<220> FEATURE:
<223> OTHER INFORMATION: synthetic construct

<400> SEQUENCE: 17
```

```
Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95
```

-continued

```
Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
            130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
            165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205

Ser Ile Val Tyr Lys Lys Glu Gly Glu Gln Val Glu Phe Ser Phe Pro
            210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
            245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
            290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
            325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
            355                 360                 365

Gln Cys Leu Leu Ser Asp Ser Gly Gln Val Leu Leu Glu Ser Asn Ile
            370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
            405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
            435                 440                 445

His Arg Phe Gln Lys Thr Cys Ser Pro Ile
    450                 455
```

<210> SEQ ID NO 18
<211> LENGTH: 744
<212> TYPE: DNA
<213> ORGANISM: Artificial Sequence
<220> FEATURE:
<223> OTHER INFORMATION: synthetic construct

<400> SEQUENCE: 18

-continued

```
aaggaccaag tgtttcagcc ttccacagtg gcatcttcag agggagctgt ggtggaaatc      60
ttctgtaatc actctgtgtc caatgcttac aacttcttct ggtaccttca cttcccggga     120
tgtgcaccaa gactccttgt taaaggctca aagccttctc agcagggacg atacaacatg     180
acctatgaac ggttctcttc atcgctgctc atcctccagg tgcgggaggc agatgctgct     240
gtttactact gtgctgtctg caccttatac aacttcaaca aattttactt tggatctggg     300
accaaactca atgtaaaacc aaatatccag aaccctgacc ctgccgtgta ccagctgaga     360
gactctaaat ccagtgacaa gtctgtctgc ctattcaccg attttgattc tcaaacaaat     420
gtgtcacaaa gtaaggattc tgatgtgtat atcacagaca aaactgtgct agacatgagg     480
tctatggact tcaagagcaa cagtgctgtg gcctggagca caaatctga ctttgcatgt      540 gcaaacgcct tcaacaacag cattattcca gaagacacct tcttccccag cccagaaagt     600
tcctgtgatg tcaagctggt cgagaaaagc tttgaaacag atacgaacct aaactttcaa     660
aacctgtcag tgattgggtt ccgaatcctc ctcctgaaag tggccgggtt taatctgctc     720
atgacgctgc ggctgtggtc cagc                                            744
```

<210> SEQ ID NO 19
<211> LENGTH: 864
<212> TYPE: DNA
<213> ORGANISM: Artificial Sequence
<220> FEATURE:
<223> OTHER INFORMATION: synthetic construct

<400> SEQUENCE: 19

```
ggtgtcactc agaccccaaa attccaggtc ctgaagacag gacagagcat gacactgcag      60
tgtgcccagg atatgaacca tgaatacatg tcctggtatc gacaagaccc aggcatgggg     120
ctgaggctga ttcattactc agttggtgct ggtatcactg accaaggaga agtccccaat     180
ggctacaatg tctccagatc aaccacagag gatttcccgc tcaggctgct gtcggctgct     240
ccctcccaga catctgtgta cttctgtgcc agcctgacag ataacaatga gcagttcttc     300
gggccaggga cacggctcac cgtgctagag gacctgaaga acgtgttccc cccagaggtg     360
gccgtgttcg agccttctga ggccgagatc agccacaccc agaaagccac cctcgtgtgt     420
ctggccaccg gcttctaccc cgaccatgtg gaactgtctt ggtgggtcaa cggcaaagag     480
gtgcacagcg gagtgtccac cgacccccag cctctgaaag aacagcccgc cctgaacgac     540
agccggtact gcctgagcag cagactgaga gtgtccgcca ccttctggca gaaccccgg      600 aaccacttca gatgccaggt gcagttctac ggcctgagcg agaacgacga gtggacccag     660
gacagagcca gcccgtgac ccagatcgtg tctgccgaag cctggggcag agccgattgc      720
ggctttacca gcgagagcta ccagcagggc gtgctgagcg ccaccatcct gtacgagatt     780
ctgctgggca aggccaccct gtacgctgtg ctggtgtcag ccctggtgct gatggccatg     840
gtcaagcgga aggacagcag aggc                                            864
```

<210> SEQ ID NO 20
<211> LENGTH: 17
<212> TYPE: PRT
<213> ORGANISM: Artificial Sequence
<220> FEATURE:
<223> OTHER INFORMATION: synthetic construct

<400> SEQUENCE: 20

```
Met Met Arg Pro Ile Val Leu Val Leu Leu Phe Ala Thr Ser Ala Leu
1               5                   10                  15
```

-continued

Ala

<210> SEQ ID NO 21
<211> LENGTH: 25
<212> TYPE: PRT
<213> ORGANISM: Artificial Sequence
<220> FEATURE:
<223> OTHER INFORMATION: synthetic construct

<400> SEQUENCE: 21

Met Ala Leu Gln Ser Thr Leu Gly Ala Val Trp Leu Gly Leu Leu Leu
1               5                   10                  15

Asn Ser Leu Trp Lys Val Ala Glu Ser
            20                  25

<210> SEQ ID NO 22
<211> LENGTH: 21
<212> TYPE: PRT
<213> ORGANISM: Artificial Sequence
<220> FEATURE:
<223> OTHER INFORMATION: synthetic construct

<400> SEQUENCE: 22

Met Ser Ile Gly Leu Leu Cys Cys Ala Ala Leu Ser Leu Leu Trp Ala
1               5                   10                  15

Gly Pro Val Asn Ala
            20

<210> SEQ ID NO 23
<211> LENGTH: 75
<212> TYPE: DNA
<213> ORGANISM: Artificial Sequence
<220> FEATURE:
<223> OTHER INFORMATION: synthetic construct

<400> SEQUENCE: 23
atggctttgc agagcactct gggggcggtg tggctagggc ttctcctcaa ctctctctgg      60
aaggttgcag aaagc                                                       75

<210> SEQ ID NO 24
<211> LENGTH: 63
<212> TYPE: DNA
<213> ORGANISM: Artificial Sequence
<220> FEATURE:
<223> OTHER INFORMATION: synthetic construct

<400> SEQUENCE: 24
atgagcatcg gcctcctgtg ctgtgcagcc ttgtctctcc tgtgggcagg tccagtgaat      60
gct                                                                    63

<210> SEQ ID NO 25
<211> LENGTH: 21
<212> TYPE: DNA
<213> ORGANISM: Artificial Sequence
<220> FEATURE:
<223> OTHER INFORMATION: synthetic construct

<400> SEQUENCE: 25
guaaggauuc ugauguguat t                                                21

<210> SEQ ID NO 26
<211> LENGTH: 21
<212> TYPE: DNA

-continued

```
<213> ORGANISM: Artificial Sequence
<220> FEATURE:
<223> OTHER INFORMATION: synthetic construct

<400> SEQUENCE: 26
uacacaucag aauccuuact t                                    21

<210> SEQ ID NO 27
<211> LENGTH: 21
<212> TYPE: DNA
<213> ORGANISM: Artificial Sequence
<220> FEATURE:
<223> OTHER INFORMATION: synthetic construct

<400> SEQUENCE: 27
ccaccauccu cuaugagaut t                                    21

<210> SEQ ID NO 28
<211> LENGTH: 21
<212> TYPE: DNA
<213> ORGANISM: Artificial Sequence
<220> FEATURE:
<223> OTHER INFORMATION: synthetic construct

<400> SEQUENCE: 28
aucucauaga ggaugguggt t                                    21
```